(12) United States Patent
Palli et al.

(10) Patent No.: US 7,091,038 B2
(45) Date of Patent: Aug. 15, 2006

(54) ECDYSONE RECEPTOR-BASED INDUCIBLE GENE EXPRESSION SYSTEM

(75) Inventors: Subba Reddy Palli, Lansdale, PA (US); Marrianna Zinovjevna Kapitskaya, North Wales, PA (US); Dean Ervin Cress, Souderton, PA (US)

(73) Assignee: RheoGene, Inc., Norristown, PA (US)

( * ) Notice: Subject to any disclaimer, the term of this patent is extended or adjusted under 35 U.S.C. 154(b) by 508 days.

(21) Appl. No.: 09/965,703

(22) Filed: Sep. 26, 2001

(65) Prior Publication Data

US 2002/0119521 A1 Aug. 29, 2002

Related U.S. Application Data

(63) Continuation-in-part of application No. PCT/US01/09050, filed on Mar. 21, 2001.

(60) Provisional application No. 60/191,355, filed on Mar. 22, 2000, provisional application No. 60/269,799, filed on Feb. 20, 2001.

(51) Int. Cl.
*C12P 21/06* (2006.01)

(52) U.S. Cl. ............... 435/320.1; 435/7.8; 435/69.1; 536/23.5; 530/350

(58) Field of Classification Search ........... 435/69.1, 435/320.1, 7.8; 530/350; 536/23.5
See application file for complete search history.

(56) References Cited

U.S. PATENT DOCUMENTS

| 5,283,173 | A | 2/1994 | Fields et al. | |
|---|---|---|---|---|
| 5,880,333 | A | 3/1999 | Goff et al. | |
| 5,919,667 | A | * | 7/1999 | Gage et al. ............ 439/91.4 |
| 6,265,173 | B1 | 7/2001 | Evans et al. | |
| 6,300,488 | B1 | 10/2001 | Gage et al. | |

FOREIGN PATENT DOCUMENTS

| EP | 0798378 | 10/1997 |
|---|---|---|
| EP | 0965644 | 12/1999 |
| WO | WO 96/27673 | 9/1996 |
| WO | WO9738117 | 10/1997 |
| WO | WO9902683 | 1/1999 |
| WO | WO 99/10510 | 3/1999 |
| WO | WO9958155 | 11/1999 |

OTHER PUBLICATIONS

Martinez A et al. Creation of ecdysone receptor chimeras in plants for controlled regulation of gene expression. Mol. Gen Genet. Apr. 1999;261(3):546-52.*

Leonhardt SA et al. Agonist and antagonists induce homodimerization and mixed ligand heterodimerization of human progesterone receptors in vivo by a mammalian two-hybrid assay. Mol Endocrinol. Dec. 1998;12(12):1914-30.*

Licitra et al. Proc. Natl. Acad. Sci. USA vol. 93; 12817-12821, 1996.*

Riddiford et al., 2000, Vitam Horn., 60:1-73.

(Continued)

*Primary Examiner*—Elizabeth Kemmerer
*Assistant Examiner*—Shulamith H. Shafer
(74) *Attorney, Agent, or Firm*—Camille Jolly-Tornetta

(57) ABSTRACT

This invention relates to the field of biotechnology or genetic engineering. Specifically, this invention relates to the field of gene expression. More specifically, this invention relates to a novel inducible gene expression system and methods of modulating gene expression in a host cell for applications such as gene therapy, large-scale production of proteins and antibodies, cell-based high throughput screetng assays, functional genomics and regulation of traits in transgenic plants and animals.

10 Claims, 8 Drawing Sheets

OTHER PUBLICATIONS

Christopherson et al., 1992, PNAS, 89:6314-6318.
Suhr et al., 1996, PNAS, 95:7999-8004.
Yao, et al., 1993, Nature, 366:476-479.
Yao, et al., 1992, Cell, 71:63-72.
No et al., 1996, PNAS, 93:3346-3351.
Kakizawa, Tomoko et al., 1997, Ligand-dependent heterodimerization of thyroid hormone receptor and retinoid X receptor, Journal of Biological Chemistry 272: 23799-23804.
Perera, Srini et al., 1999, An analysis of ecdysone receptor domains required for heterodimerization with ultraspiracle, Archives of Insect Biochemistry and Physiology 41: 61-70.
Leid M et al., 1992, Purification, cloning, and RXR identity of the Hela cell factor with which RAR or TR heterodimerizes to bind target sequences efficiently, Cell 68: 377-395.
Perera Srini et al., 1999, Studies on two ecdysone receptor isoforms of the spruce budworm, Choristoneura fumiferana, Molecular and Cellular Endocrinology 152: 73-84.
Koelle MR et al., The Drosophila EcR gene encodes an ecdysone receptor, a new member of the steroid receptor superfamily, Cell 67: 59-77.

* cited by examiner

GAL4CfEcR

VP16RXR pGAL4RELuc GAL4RE TATA

GAL4CfEcR

VP16USP    CfUSPDEF pGAL4RELuc GAL4RE TATA

GAL4RXR

VP16CfEcR pGAL4RELuc GAL4RE TATA

GAL4RXR

VP16DmEcR pGAL4RELu GAL4RE TATA          Luciferase

GAL4USP

VP16CfEcR pGAL4RELuc GAL4RE TATA

GAL4CfEcRVP16 pGAL4RELuc GAL4RE TATA

VP16CfEcR pEcREctRELuc EcRE SV40       Luciferase

VP16DmEcR

RXR pE/GRELacZ E/GRE TATA        LacZ

VP16CfEcR

RXR pE/GRELacZ E/GRE TATA        LacZ

VP16CfEcR pE/GRELacZ E/GRE TATA        LacZ

ECDYSONE RECEPTOR-BASED INDUCIBLE GENE EXPRESSION SYSTEM

This application is a Continuation-In-Part application and claims priority to co-pending International PCT application Serial number PCT/JUS01/09050, filed Mar. 21, 2001, which claims priority to both co-pending U.S. provisional application Ser. No. 60/191,355, filed Mar. 22, 2000 and co-pending U.S. provisional application Ser. No. 60/269,799, filed Feb. 20, 2001.

FIELD OF THE INVENTION

This invention relates to the field of biotechnology or genetic engineering. Specifically, this invention relates to the field of gene expression. More specifically, this invention relates to a novel ecdysone receptor-based inducible gene expression system and methods of modulating the expression of a gene within a host cell using this inducible gene expression system.

BACKGROUND OF THE INVENTION

Various publications are cited herein, the disclosures of which are incorporated by reference in their entireties. However, the citation of any reference herein should not be construed as an admission that such reference is available as "Prior Art" to the instant application.

In the field of genetic engineering, precise control of gene expression is a valuable tool for studying, manipulating, and controlling development and other physiological processes. Gene expression is a complex biological process involving a number of specific protein-protein interactions. In order for gene expression to be triggered, such that it produces the RNA necessary as the first step in protein synthesis, a transcriptional activator must be brought into proximity of a promoter that controls gene transcription. Typically, the transcriptional activator itself is associated with a protein that has at least one DNA binding domain that binds to DNA binding sites present in the promoter regions of genes. Thus, for gene expression to occur, a protein comprising a DNA binding domain and a transactivation domain located at an appropriate distance from the DNA binding domain must be brought into the correct position in the promoter region of the gene.

The traditional transgenic approach utilizes a cell-type specific promoter to drive the expression of a designed transgene. A DNA construct containing the transgene is first incorporated into a host genome. When triggered by a transcriptional activator, expression of the transgene occurs in a given cell type.

Another means to regulate expression of foreign genes in cells is through inducible promoters. Examples of the use of such inducible promoters include the PR 1-a promoter, prokaryotic repressor-operator systems, immunosuppressive-immunophilin systems, and higher eukaryotic transcription activation systems such as steroid hormone receptor systems and are described below.

The PR1-a promoter from tobacco is induced during the systemic acquired resistance response following pathogen attack. The use of PR1-a may be limited because it often responds to endogenous materials and external factors such as pathogens, UV-B radiation, and pollutants. Gene regulation systems based on promoters induced by heat shock, interferon and heavy metals have been described (Wurn et al., 1986, Proc. Natl. Acad. Sci. USA 83:5414–5418; Amheiter et al., 1990 Cell 62:51–61; Filmus et al., 1992 Nucleic Acids Research 20:27550–27560). However, these systems have limitations due to their effect on expression of non-target genes. These systems are also leaky.

Prokaryotic repressor-operator systems utilize bacterial repressor proteins and the unique operator DNA sequences to which they bind. Both the tetracycline ("Tet") and lactose ("Lac") repressor-operator systems from the bacterium *Escherichia coli* have been used in plants and animals to control gene expression. In the Tet system, tetracycline binds to the TetR repressor protein, resulting in a conformational change which releases the repressor protein from the operator which as a result allows transcription to occur. In the Lac system, a lac operon is activated in response to the presence of lactose, or synthetic analogs such as isopropyl-b-D-thiogalactoside. Unfortunately, the use of such systems is restricted by unstable chemistry of the ligands, i.e. tetracycline and lactose, their toxicity, their natural presence, or the relatively high levels required for induction or repression. For similar reasons, utility of such systems in animals is limited.

Immunosuppressive molecules such as FK506, rapamycin and cyclosporine A can bind to immunophilins FKBP12, cyclophilin, etc. Using this information, a general strategy has been devised to bring together any two proteins simply by placing FK506 on each of the two proteins or by placing FK506 on one and cyclosporine A on another one. A synthetic homodimer of FK506 (FK1012) or a compound resulted from fusion of FK506-cyclosporine (FKCsA) can then be used to induce dimerization of these molecules (Spencer et al., 1993, Science 262:1019–24; Belshaw et al., 1996 *Proc Natl Acad Sci USA* 93:4604–7). Gal4 DNA binding domain fused to FKBP12 and VP16 activator domain fused to cyclophilin, and FKCsA compound were used to show heterodimerization and activation of a reporter gene under the control of a promoter containing Gal4 binding sites. Unfortunately, this system includes immunosuppressants that can have unwanted side effects and therefore, limits its use for various mammalian gene switch applications.

Higher eukaryotic transcription activation systems such as steroid hormone receptor systems have also been employed. Steroid hormone receptors are members of the nuclear receptor superfamily and are found in vertebrate and invertebrate cells. Unfortunately, use of steroidal compounds that activate the receptors for the regulation of gene expression, particularly in plants and mammals, is limited due to their involvement in many other natural biological pathways in such organisms. In order to overcome such difficulties, an alternative system has been developed using insect ecdysone receptors (EcR).

Growth, molting, and development in insects are regulated by the ecdysone steroid hormone (molting hormone) and the juvenile hormones (Dhadialla, et al., 1998. Annu. Rev. Entomol. 43: 545–569). The molecular target for ecdysone in insects consists of at least ecdysone receptor (EcR) and ultraspiracle protein (USP). EcR is a member of the nuclear steroid receptor super family that is characterized by signature DNA and ligand binding domains, and an activation domain (Koelle et al. 1991, Cell, 67:59–77). EcR receptors are responsive to a number of steroidal compounds such as ponasterone A and muristerone A. Recently, non-steroidal compounds with ecdysteroid agonist activity have been described, including the commercially available insecticides tebufenozide and methoxyfenozide that are marketed world wide by Rohm and Haas Company (see International Patent Application No. PCT/EP96/00686 and U.S. Pat. No. 5,530,028). Both analogs have exceptional safety profiles to other organisms.

The insect ecdysone receptor (EcR) heterodimerizes with Ultraspiracle (USP), the insect homologue of the mammalian RXR, and binds ecdysteroids and ecdysone receptor response elements and activate transcription of ecdysone responsive genes (Riddiford et al., 2000, Vitam Horm., 60:1–73). The EcR/USP/ligand complexes play important roles during insect development and reproduction. The EcR is a member of the steroid hormone receptor superfamily and has five modular domains, A/B (transactivation), C (DNA binding, heterodimerization), D (Hinge, heterodimerization), E (ligand binding, heterodimerization and transactivation and F (transactivation) domains. Some of these domains such as A/B, C and E retain their function when they are fused to other proteins.

Tightly regulated inducible gene expression systems or "gene switches" are useful for various applications such as gene therapy, large scale production of proteins in cells, cell based high throughput screening assays, functional genomics and regulation of traits in transgenic plants and animals.

The first version of EcR-based gene switch used *Drosophila melanogaster* EcR (DmEcR) and *Mus musculus* RXR (MmRXR) and showed that these receptors in the presence of steroid, ponasteroneA, transactivate reporter genes in mammalian cell lines and transgenic mice (Christopherson et al., 1992, PNAS, 89:6314–6318; No et al., 1996, PNAS, 93:3346–3351). Later, Suhr et al. (1998, PNAS, 95:7999–8004) showed that non-steroidal ecdysone agonist, tebufenozide, induced high level of transactivation of reporter genes in mammalian cells through *Bombyx mori* EcR (BmEcR) in the absence of exogenous heterodimer partner.

International Patent Applications No. PCT/US97/05330 (WO 97/38117) and PCT/US99/08381 (WO99/58155) disclose methods for modulating the expression of an exogenous gene in which a DNA construct comprising the exogenous gene and an ecdysone response element is activated by a second DNA construct comprising an ecdysone receptor that, in the presence of a ligand therefor, and optionally in the presence of a receptor capable of acting as a silent partner, binds to the ecdysone response element to induce gene expression. The ecdysone receptor of choice was isolated from *Drosophila melanogaster*. Typically, such systems require the presence of the silent partner, preferably retinoid X receptor (RXR), in order to provide optimum activation. In mammalian cells, insect ecdysone receptor (EcR) heterodimerizes with retinoid X receptor (RXR) and regulates expression of target genes in a ligand dependent manner. International Patent Application No. PCT/US98/14215 (WO 99/02683) discloses that the ecdysone receptor isolated from the silk moth *Bombyx mori* is functional in mammalian systems without the need for an exogenous dimer partner.

U.S. Pat. No. 6,265,173 B 1 discloses that various members of the steroid/thyroid superfamily of receptors can combine with *Drosophila melanogaster* ultraspiracle receptor (USP) or fragments thereof comprising at least the dimerization domain of USP for use in a gene expression system. U.S. Pat. No. 5,880,333 discloses a *Drosophila melanogaster* EcR and ultraspiracle (USP) heterodimer system used in plants in which the transactivation domain and the DNA binding domain are positioned on two different hybrid proteins. Unfortunately, these USP-based systems are constitutive in animal cells and therefore, are not effective for regulating reporter gene expression, particularly, in animal cells (for comparison, see Example 1.2, below).

In each of these cases, the transactivation domain and the DNA binding domain (either as native EcR as in International Patent Application No. PCT/US98/14215 or as modified EcR as in International Patent Application No. PCT/US97/05330) were incorporated into a single molecule and the other heterodimeric partners, either USP or RXR, were used in their native state.

Drawbacks of the above described EcR-based gene regulation systems include a considerable background activity in the absence of ligands and the non-applicability of these systems for use in both plants and animals (see U.S. Pat. No. 5,880,333). Therefore, a need exists in the art for improved EcR-based systems to precisely modulate the expression of exogenous genes in both plants and animals. Such improved systems would be useful for applications such as gene therapy, large scale production of proteins and antibodies, cell-based high throughput screening assays, functional genomics and regulation of traits in transgenic animals. Improved systems that are simple, compact, and dependent on ligands that are relatively inexpensive, readily available, and of low toxicity to the host would prove useful for regulating biological systems.

For certain applications such as gene therapy, it may be desirable to have an inducible gene expression system that responds well to synthetic non-steroid ligands and at the same is insensitive to the natural steroids. Thus, improved systems that are simple, compact, and dependent on ligands that are relatively inexpensive, readily available, and of low toxicity to the host would prove useful for regulating biological systems.

Herein, Applicants describe an improved ecdysone receptor-based inducible gene expression system in which the transactivation and DNA binding domains are separated from each other by placing them on two different proteins results in greatly reduced background activity in the absence of a ligand and significantly increased activity over background in the presence of a ligand. This two-hybrid system is a significantly improved inducible gene expression modulation system compared to the two systems disclosed in applications PCT/US97/05330 and PCT/US98/14215. The two-hybrid system exploits the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). Since the DNA binding and transactivation domains reside on two different molecules, the background activity in the absence of ligand is greatly reduced.

A two-hybrid system also provides improved sensitivity to non-steroidal ligands for example, diacylhydrazines, when compared to steroidal ligands for example, ponasterone A ("PonA") or muristerone A ("MurA"). In addition, since transactivation based on EcR gene switches is often cell-line dependent, it is easier to tailor switching systems to obtain maximum transactivation capability for each application. Furthermore, the two-hybrid system avoids some side effects due to overexpression of RXR that often occur when unmodified RXR is used as a switching partner.

Thus Applicants' invention provides an improved ecdysone receptor-based inducible gene expression system for use in both prokaryotic and eukaryotic host cells in which ligand sensitivity and magnitude of transactivation may be selected as desired, depending upon the application.

The EcR is a member of the nuclear receptor superfamily and classified into subfamily 1, group H (referred to herein as "Group H nuclear receptors"). The members of each group share 40–60% amino acid identity in the E (ligand binding) domain (Laudet et al., A Unified Nomenclature System for the Nuclear Receptor Subfamily, 1999; Cell 97:161–163). In addition to the ecdysone receptor, other members of this nuclear receptor subfamily 1, group H include: ubiquitous receptor (UR), Orphan receptor 1 (OR-1), steroid hormone nuclear receptor 1 (NER-1), RXR interacting protein-15 (RIP-15), liver x receptor β (LXRβ), steroid hormone receptor like protein (RLD-1), liver x receptor (LXR), liver x receptor α (LXRα), farnesoid x receptor (FXR), receptor interacting protein 14 (RIP-14), and farnesol receptor (HRR-1).

Given the close relatedness of ecdysone receptor to other Group H nuclear receptors, Applicants' invention also provides a two-hybrid Group H nuclear receptor-based gene expression system comprising ligand binding domains of a Group H nuclear receptor and its respective dimerization partner. Thus, Applicants' invention also provides a two-hybrid Group H nuclear receptor-based gene expression system for use in both prokaryotic and eukaryotic host cells in which ligand sensitivity and magnitude of transactivation may be selected as desired, depending upon the application.

SUMMARY OF THE INVENTION

The present invention relates to a novel ecdysone receptor-based inducible gene expression system, novel receptor polynucleotides and polypeptides for use in the novel inducible gene expression system, and methods of modulating the expression of a gene within a host cell using this inducible gene expression system. The present invention also relates to a novel Group H nuclear receptor-based gene expression system, novel receptor polynucleotides and polypeptides for use in the novel inducible gene expression system, and methods of modulating the expression of a gene within a host cell using this inducible gene expression system. In a specific embodiment, Applicants' invention relates to an improved Group H nuclear receptor-based inducible gene expression modulation system comprising a polynucleotide encoding a receptor polypeptide comprising a truncation mutation.

Specifically, the present invention relates to a gene expression modulation system comprising: a) a first gene expression cassette that is capable of being expressed in a host cell comprising a polynucleotide that encodes a first polypeptide comprising: i) a DNA-binding domain that recognizes a response element associated with a gene whose expression is to be modulated; and ii) a ligand binding domain comprising a ligand binding domain from a nuclear receptor; and b) a second gene expression cassette that is capable of being expressed in the host cell comprising a polynucleotide sequence that encodes a second polypeptide comprising: i) a transactivation domain; and ii) a ligand binding domain comprising a ligand binding domain from a nuclear receptor other than an ultraspiracle receptor. In a specific embodiment, the gene expression modulation system comprises a DNA binding domain and a transactivation domain from a polypeptide other than a Group H nuclear receptor, an ecdysone receptor, a Group B nuclear receptor, a retinoid X receptor, or an ultraspiracle receptor. In another specific embodiment, the ligand binding domains from the first polypeptide and the second polypeptide are different and dimerize.

In a specific embodiment, the ligand binding domain of the first polypeptide comprises a Group H nuclear receptor ligand binding domain. Preferably, the ligand binding domain of the first polypeptide comprises an ecdysone receptor (EcR) ligand binding domain. In another specific embodiment, ligand binding domain of the second polypeptide comprises a Group B nuclear receptor ligand binding domain. Preferably, the ligand binding domain of the second polypeptide comprises a retinoid X receptor (RXR) ligand binding domain.

In a preferred embodiment, the ligand binding domain of the first polypeptide comprises a Group H nuclear receptor ligand binding domain and the ligand binding domain of the second polypeptide comprises a Group B nuclear receptor ligand binding domain. In another preferred embodiment, the ligand binding domain of the first polypeptide comprises an ecdysone receptor ligand binding domain and the ligand binding domain of the second polypeptide comprises a retinoid X receptor ligand binding domain.

The present invention also relates to a gene expression modulation system according to the invention further comprising c) a third gene expression cassette comprising: i) a response element to which the DNA-binding domain of the first polypeptide binds; ii) a promoter that is activated by the transactivation domain of the second polypeptide; and iii) the gene whose expression is to be modulated.

The present invention also relates to an isolated polynucleotide encoding a truncated Group H nuclear receptor, truncated EcR, truncated Group B nuclear receptor, or a truncated RXR polypeptide, wherein the truncation mutation affects ligand binding activity or ligand sensitivity.

In particular, the present invention relates to an isolated polynucleotide encoding a truncated EcR or a truncated RXR polypeptide comprising a truncation mutation that reduces ligand binding activity or ligand sensitivity of said EcR or RXR polypeptide. In a specific embodiment, the present invention relates to an isolated polynucleotide encoding a truncated EcR or a truncated RXR polypeptide comprising a truncation mutation that reduces steroid binding activity or steroid sensitivity of said EcR or RXR polypeptide. In another specific embodiment, the present invention relates to an isolated polynucleotide encoding a truncated EcR or a truncated RXR polypeptide comprising a truncation mutation that reduces non-steroid binding activity or non-steroid sensitivity of said EcR or RXR polypeptide.

The present invention also relates to an isolated polynucleotide encoding a truncated EcR or a truncated RXR polypeptide comprising a truncation mutation that enhances ligand binding activity or ligand sensitivity of said EcR or RXR polypeptide. In a specific embodiment, the present invention relates to an isolated polynucleotide encoding a truncated EcR or a truncated RXR polypeptide comprising a truncation mutation that enhances steroid binding activity or steroid sensitivity of said EcR or RXR polypeptide. In another specific embodiment, the present invention relates to an isolated polynucleotide encoding a truncated EcR or a truncated RXR polypeptide comprising a truncation mutation that enhances non-steroid binding activity or non-steroid sensitivity of said EcR or RXR polypeptide.

The present invention also relates to an isolated polynucleotide encoding a truncated RXR polypeptide comprising a truncation mutation that increases ligand sensitivity of a heterodimer comprising the truncated retinoid X receptor polypeptide and a dimerization partner. In a specific embodiment, the dimerization partner is an ecdysone receptor polypeptide.

The present invention also relates to an isolated polypeptide encoded by a polynucleotide according to Applicants' invention. In particular, the present invention relates to an isolated truncated EcR or truncated RXR polypeptide comprising a truncation mutation, wherein the EcR or RXR polypeptide is encoded by a polynucleotide according to the invention.

Thus, the present invention also relates to an isolated truncated Group H nuclear receptor, truncated EcR, truncated Group B nuclear receptor, or truncated RXR polypeptide comprising a truncation mutation that affects ligand binding activity or ligand sensitivity of the Group H nuclear receptor polypeptide, the EcR polypeptide, the Group B nuclear receptor polypeptide, or the RXR polypeptide.

Applicants' invention also relates to methods of modulating gene expression in a host cell using a gene expression modulation system according to the invention. Specifically, Applicants' invention provides a method of modulating the expression of a gene in a host cell comprising the gene to be modulated comprising the steps of: a) introducing into the host cell a gene expression modulation system according to the invention; and b) introducing into the host cell a ligand that independently combines with the ligand binding domains of the first polypeptide and the second polypeptide of the gene expression modulation system; wherein the gene to be expressed is a component of a chimeric gene comprising: i) a response element comprising a domain to which the DNA binding domain from the first polypeptide binds; ii) a promoter that is activated by the transactivation domain of the second polypeptide; and iii) the gene whose expression is to be modulated, whereby a complex is formed comprising the ligand, the first polypeptide, and the second polypeptide, and whereby the complex modulates expression of the gene in the host cell.

Applicants' invention also provides an isolated host cell comprising an inducible gene expression system according to the invention. The present invention also relates to an isolated host cell comprising a polynucleotide or polypeptide according to the invention. Accordingly, Applicants' invention also relates to a non-human organism comprising a host cell according to the invention.

DETAILED DESCRIPTION OF THE INVENTION

Figure 1:
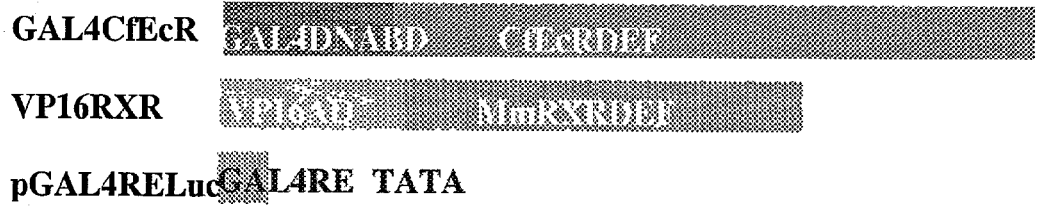
FIG. 1: An ecdysone receptor-based gene expression system comprising a first gene expression cassette encoding a Gal4DBD-CfEcRDEF chimeric polypeptide and a second gene expression cassette encoding a VP16AD-MmRXR-DEF chimeric polypeptide; prepared as described in Example 1 (switch 1.1).
Figure 2:
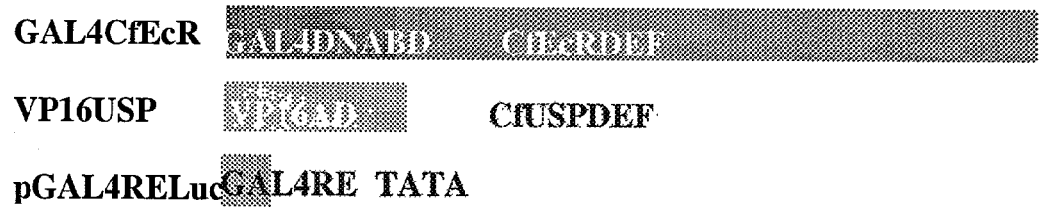
FIG. 2: An ecdysone receptor-based gene expression system comprising a first gene expression cassette encoding a Gal4DBD-CfEcRDEF chimeric polypeptide and a second gene expression cassette encoding a VP16AD-CfUSPDEF chimeric polypeptide; prepared as described in Example 1 (switch 1.2).
Figure 3:
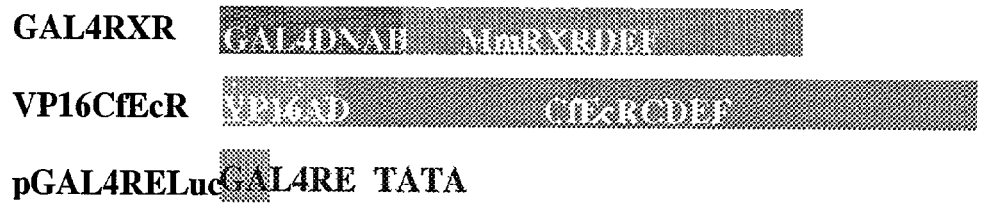
FIG. 3: An ecdysone receptor-based gene expression system comprising a first gene expression cassette encoding a Gal4DBD-MmRXRDEF chimeric polypeptide and a second gene expression cassette encoding a VP16AD-CfEcRC-DEF chimeric polypeptide; prepared as described in Example 1 (switch 1.3).
Figure 4:
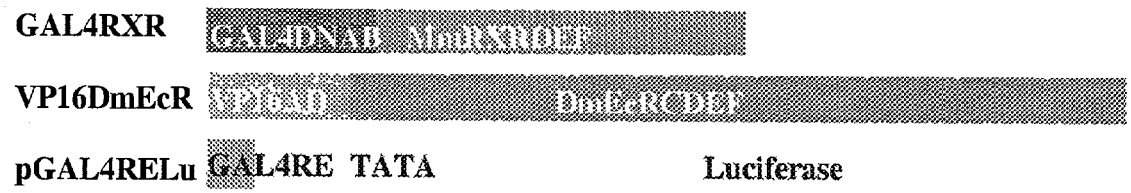
FIG. 4: An ecdysone receptor-based gene expression system comprising a first gene expression cassette encoding a Gal4DBD-MmRXRDEF chimeric polypeptide and a second gene expression cassette encoding a VP16AD-DmEcRCDEF chimeric polypeptide; prepared as described in Example 1 (switch 1.4).
Figure 5:
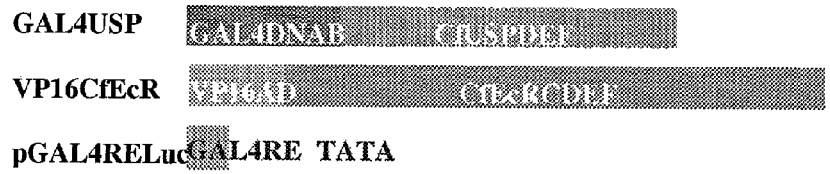
FIG. 5: An ecdysone receptor-based gene expression system comprising a first gene expression cassette encoding a Gal4DBD-CfUSPDEF chimeric polypeptide and a second gene expression cassette encoding a VP16AD-CfEcRCDEF chimeric polypeptide; prepared as described in Example 1 (switch 1.5).
Figure 6:
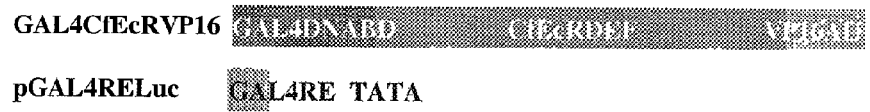
FIG. 6: An ecdysone receptor-based gene expression system comprising a first gene expression cassette encoding a Gal4DBD-CfEcRDEF-VP16AD chimeric polypeptide; prepared as described in Example 1 (switch 1.6).
Figure 7:
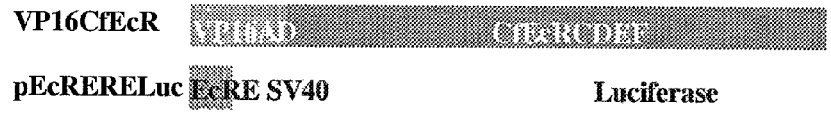
FIG. 7: An ecdysone receptor-based gene expression system comprising a first gene expression cassette encoding a VP16AD-CfEcRCDEF chimeric polypeptide; prepared as described in Example 1 (switch 1.7).
Figure 8:
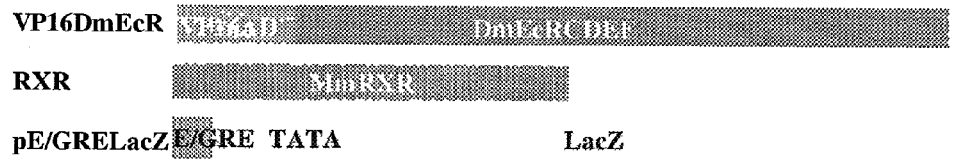
FIG. 8: An ecdysone receptor-based gene expression system comprising a first gene expression cassette encoding a VP16AD-DmEcRCDEF chimeric polypeptide and a second gene expression cassette encoding a MmRXR polypeptide; prepared as described in Example 1 (switch 1.8).
Figure 9:
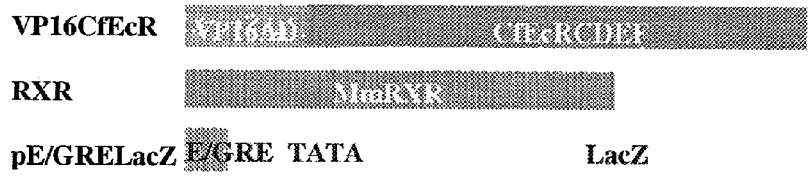
FIG. 9: An ecdysone receptor-based gene expression system comprising a first gene expression cassette encoding a VP16AD-CfEcRCDEF chimeric polypeptide and a second gene expression cassette encoding a MmRXR polypeptide; prepared as described in Example 1 (switch 1.9).
Figure 10:
FIG. 10: An ecdysone receptor-based gene expression system comprising a gene expression cassette encoding a Gal4DBD-CfEcRCDEF chimeric polypeptide; prepared as described in Example 1 (switch 1.10).

Applicants describe herein an improved ecdysone receptor-based inducible gene expression system in which the transactivation and DNA binding domains are separated from each other by placing them on two different proteins results in greatly reduced background activity in the absence of a ligand and significantly increased activity over background in the presence of a ligand. This two-hybrid system is a significantly improved inducible gene expression modulation system compared to the two systems disclosed in applications PCT/US97/05330 and PCT/US98/14215. The two-hybrid system exploits the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). Briefly, the two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, the interaction of the first polypeptide with the second polypeptide effectively tethers the DNA binding domain to the transactivation domain. Since the DNA binding and transactivation domains reside on two different molecules, the background activity in the absence of ligand is greatly reduced.

Applicants' two-hybrid system also provides improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provide higher activity at a lower concentration. In addition, since transactivation based on EcR gene switches is often cell-line dependent, it is easier to tailor switching systems to obtain maximum transactivation capability for each application. Furthermore, the two-hybrid system avoids some side effects due to overexpression of RXR that often occur when unmodified RXR is used as a switching partner. In a preferred two-hybrid system, native DNA binding and transactivation domains of EcR or RXR are eliminated and as a result, these hybrid molecules have less chance of interacting with other steroid hormone receptors present in the cell resulting in reduced side effects.

In a preferred embodiment, Applicants' improved ecdysone receptor-based inducible gene expression system comprises a truncation mutant of an ecdysone receptor or a retinoid X receptor (RXR) polypeptide that affects ligand binding activity or ligand sensitivity. This mutational effect may increase or reduce ligand binding activity or ligand sensitivity and may be steroid or non-steroid specific. Thus, Applicants' invention provides an improved ecdysone receptor-based inducible gene expression system useful for modulating expression of a gene of interest in a host cell. In a particularly desirable embodiment, Applicants' invention provides an inducible gene expression system that has a reduced level of background gene expression and responds to submicromolar concentrations of non-steroidal ligand. Thus, Applicants' novel inducible gene expression system and its use in methods of modulating gene expression in a host cell overcome the limitations of currently available inducible expression systems and provide the skilled artisan with an effective means to control gene expression.

The present invention provides a novel inducible gene expression system that can be used to modulate gene expression in both prokaryotic and eukaryotic host cells. Applicants' invention is useful for applications such as gene therapy, large scale production of proteins and antibodies, cell-based high throughput screening assays, orthogonal ligand screening assays, functional genomics, proteomics, metabolomics, and regulation of traits in transgenic organisms, where control of gene expression levels is desirable. An advantage of Applicants' invention is that it provides a means to regulate gene expression and to tailor expression levels to suit the user's requirements.

Definitions

In this disclosure, a number of terms and abbreviations are used. The following definitions are provided and should be helpful in understanding the scope and practice of the present invention.

In a specific embodiment, the term "about" or "approximately" means within 20%, preferably within 10%, more preferably within 5%, and even more preferably within 1% of a given value or range.

The term "substantially free" means that a composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The term "isolated" for the purposes of the present invention designates a biological material (nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated". The term "purified" does not require the material to be present in a form exhibiting absolute purity, exclusive of the presence of other compounds. It is rather a relative definition.

For example, a polynucleotide present in the natural state in a plant or an animal is not isolated. The same polynucleotide separated from the adjacent nucleic acids in which it is naturally present. The term "purified" does not require the material to be present in a form exhibiting absolute purity, exclusive of the presence of other compounds. It is rather a relative definition.

A polynucleotide is in the "purified" state after purification of the starting material or of the natural material by at least one order of magnitude, preferably 2 or 3 and preferably 4 or 5 orders of magnitude.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded.

DNA includes but is not limited to cDNA, genomic DNA, plasmids DNA, synthetic DNA, and semi-synthetic DNA. DNA may be linear, circular, or supercoiled.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single stranded form, or a double-stranded helix. Double stranded DNA—DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

The term "fragment" will be understood to mean a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000 or 1500 consecutive nucleotides of a nucleic acid according to the invention.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to an assembly of nucleotides that encode a polypeptide, and includes cDNA and genomic DNA nucleic acids. "Gene" also refers to a nucleic acid fragment that expresses a specific protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Heterologous" DNA refers to DNA not naturally located in the cell, or in a chromosomal site of the cell. Preferably, the heterologous DNA includes a gene foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989 infra). Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization.

Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a $T_m$ of 55°, can be used, e.g., 5× SSC, 0.1% SDS, 0.25% milk, and no formamide; or 30% formamide, 5× SSC, 0.5% SDS). Moderate stringency hybridization conditions correspond to a higher $T_m$, e.g., 40% formamide, with 5× or 6× SCC. High stringency hybridization conditions correspond to the highest $T_m$, e.g., 50% formamide, 5× or 6× SCC.

Hybridization requires that the two nucleic acids contain complementary sequences, although depending on the stringency of the hybridization, mismatches between bases are possible. The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as disclosed or used herein as well as those substantially similar nucleic acid sequences.

In a specific embodiment of the invention, polynucleotides are detected by employing hybridization conditions comprising a hybridization step at $T_m$ of 55° C., and utilizing conditions as set forth above. In a preferred embodiment, the $T_m$ is 60° C.; in a more preferred embodiment, the $T_m$ is 63° C.; in an even more preferred embodiment, the $T_m$ is 65° C.

Post-hybridization washes also determine stringency conditions. One set of preferred conditions uses a series of washes starting with 6× SSC, 0.5% SDS at room temperature for minutes (min), then repeated with 2× SSC, 0.5% SDS at 45° C. for 30 minutes, and then repeated twice with 0.2× SSC, 0.5% SDS at 50° C. for 30 minutes. A more preferred set of stringent conditions uses higher temperatures in which the washes are identical to those above except for the temperature of the final two 30 min washes in 0.2× SSC, 0.5% SDS was increased to 60° C. Another preferred set of highly stringent conditions uses two final washes in 0.1× SSC, 0.1% SDS at 65° C. Hybridization requires that the two nucleic acids comprise complementary sequences, although depending on the stringency of the hybridization, mismatches between bases are possible.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8).

In a specific embodiment of the invention, polynucleotides are detected by employing hybridization conditions comprising a hybridization step in less than 500 mM salt and at least 37 degrees Celsius, and a washing step in 2× SSPE at least 63 degrees Celsius. In a preferred embodiment, the hybridization conditions comprise less than 200 mM salt and at least 37 degrees Celsius for the hybridization step. In a more preferred embodiment, the hybridization conditions comprise 2× SSPE and 63 degrees Celsius for both the hybridization and washing steps.

In one embodiment, the length for a hybridizable nucleic acid is at least about 10 nucleotides. Preferable a minimum length for a hybridizable nucleic acid is at least about nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "probe" refers to a single-stranded nucleic acid molecule that can base pair with a complementary single stranded target nucleic acid to form a double-stranded molecule.

As used herein, the term "oligonucleotide" refers to a nucleic acid, generally of at least 18 nucleotides, that is hybridizable to a genomic DNA molecule, a cDNA molecule, a plasmid DNA or an mRNA molecule. Oligonucleotides can be labeled, e.g., with $^{32}P$-nucleotides or nucleotides to which a label, such as biotin, has been covalently conjugated. A labeled oligonucleotide can be used as a probe to detect the presence of a nucleic acid. Oligonucleotides (one or both of which may be labeled) can be used as PCR primers, either for cloning full length or a fragment of a nucleic acid, or to detect the presence of a nucleic acid. An oligonucleotide can also be used to form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "primer" is an oligonucleotide that hybridizes to a target nucleic acid sequence to create a double stranded nucleic acid region that can serve as an initiation point for DNA synthesis under suitable conditions. Such primers may be used in a polymerase chain reaction.

"Polymerase chain reaction" is abbreviated PCR and means an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

"Reverse transcription-polymerase chain reaction" is abbreviated RT-PCR and means an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" is a double-stranded DNA sequence that is transcribed and translated into a polypeptide in a cell in vitro or in vivo when placed under the control of appropriate regulatory sequences. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in a eukaryotic cell, a polyadenylation signal and transcription termination sequence will usually be located 3' to the coding sequence.

"Open reading frame" is abbreviated ORF and means a length of nucleic acid sequence, either DNA, cDNA or RNA, that comprises a translation start signal or initiation codon, such as an ATG or AUG, and a termination codon and can be potentially translated into a polypeptide sequence.

The term "head-to-head" is used herein to describe the orientation of two polynucleotide sequences in relation to each other. Two polynucleotides are positioned in a head-to-head orientation when the 5' end of the coding strand of one polynucleotide is adjacent to the 5' end of the coding strand of the other polynucleotide, whereby the direction of transcription of each polynucleotide proceeds away from the 5' end of the other polynucleotide. The term "head-to-head" may be abbreviated (5')-to-(5') and may also be indicated by the symbols (←→) or (3'←5'5'→3').

The term "tail-to-tail" is used herein to describe the orientation of two polynucleotide sequences in relation to each other. Two polynucleotides are positioned in a tail-to-tail orientation when the 3' end of the coding strand of one polynucleotide is adjacent to the 3' end of the coding strand of the other polynucleotide, whereby the direction of transcription of each polynucleotide proceeds toward the other polynucleotide. The term "tail-to-tail" may be abbreviated (3')-to-(3') and may also be indicated by the symbols (→←) or (5'→3'3←5').

The term "head-to-tail" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→→) or (5→3'5→3').

The term "downstream" refers to a nucleotide sequence that is located 3' to reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" refer to an enzyme that binds and cuts within a specific nucleotide sequence within double stranded DNA.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" is any means for the cloning of and/or transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include but are not limited to retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" is a "replicon", which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector").

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; and Hartmut et al., Canadian Patent Application No. 2,012,311, filed Mar. 15, 1990).

A polynucleotide according to the invention can also be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et al., 1987. PNAS 84:7413; Mackey, et al., 1988. Proc. Natl. Acad. Sci. U.S.A 85:8027–8031; and Ulmer et al., 1993. Science 259:1745–1748). The use of cationic lipids may promote encapsulation of negatively charged nucleic acids, and also promote fusion with negatively charged cell membranes (Felgner and Ringold, 1989.

Science 337:387–388). Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., 1992. Hum. Gene Ther. 3:147–154; and Wu and Wu, 1987. J. Biol. Chem. 262: 4429–4432).

The term "transfection" means the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "genetic region" will refer to a region of a nucleic acid molecule or a nucleotide sequence that comprises a gene encoding a polypeptide.

In addition, the recombinant vector comprising a polynucleotide according to the invention may include one or more origins for replication in the cellular hosts in which their amplification or their expression is sought, markers or selectable markers.

The term "selectable marker" means an identifying factor, usually an antibiotic or chemical resistance gene, that is able to be selected for based upon the marker gene's effect, i.e., resistance to an antibiotic, resistance to a herbicide, calorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" means a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes may also be considered reporter genes.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". Promoters that cause a gene to be expressed in a specific cell type are commonly referred to as "cell-specific promoters" or "tissue-specific promoters". Promoters that cause a gene to be expressed at a specific stage of development or cell differentiation are commonly referred to as "developmentally-specific promoters" or "cell differentiation-specific promoters". Promoters that are induced and cause a gene to be expressed following exposure or treatment of the cell with an agent, biological molecule, chemical, ligand, light, or the like that induces the promoter are commonly referred to as "inducible promoters" or "regulatable promoters". It is further recognized that since in most cases the exact boundaries of regulatory sequences have not been completely defined, DNA fragments of different lengths may have identical promoter activity.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease SI), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

The term "response element" means one or more cis-acting DNA elements which confer responsiveness on a promoter mediated through interaction with the DNA-binding domains of the first chimeric gene. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element will be incorporated. The DNA binding domain of the first hybrid protein binds, in the presence or absence of a ligand, to the DNA sequence of a response element to initiate or suppress transcription of downstream gene(s) under the regulation of this response element. Examples of DNA sequences for response elements of the natural ecdysone receptor include: RRGG/TTCANTGAC/ACYY (SEQ ID NO: 76) (see Cherbas L., et. al., (1991), *Genes Dev.* 5, 120–131); AGGTCAN$_{(n)}$AGGTCA, where N$_{(n)}$ (SEQ ID NO: 77) can be one or more spacer nucleotides (see D'Avino PP., et. al., (1995), Mol. Cell. Endocrinol, 113, 1–9); and GGGTTGAATGAATTT (SEQ ID NO: 78) (see Antoniewski C., et. al., (1994). Mol. Cell Biol. 14, 4465–4474).

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from a nucleic acid or polynucleotide. Expression may also refer to translation of mRNA into a protein or polypeptide.

The terms "cassette", "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of this invention, the term "gene switch" refers to the combination of a response element associated with a promoter, and an EcR based system which, in the presence of one or more ligands, modulates the expression of a gene into which the response element and promoter are incorporated.

The terms "modulate" and "modulates" mean to induce, reduce or inhibit nucleic acid or gene expression, resulting in the respective induction, reduction or inhibition of protein or polypeptide production.

The plasmids or vectors according to the invention may further comprise at least one promoter suitable for driving expression of a gene in a host cell. The term "expression vector" means a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving these genes is suitable for the present invention including but not limited to: viral promoters, bacterial promoters, animal promoters, mammalian promoters, synthetic promoters, constitutive promoters, tissue specific promoter, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TPI, alkaline phosphatase promoters (useful for expression in Saccharomyces); AOX1 promoter (useful for expression in Pichia); b-lactamase, lac, ara, tet, trp, IP$_L$, IP$_R$, T7, tac, and trc promoters (useful for expression in *Escherichia coli*); light regulated-, seed specific-, pollen specific-, ovary specific-, pathogenesis or disease related-, cauliflower mosaic virus 35S, CMV 35S minimal, cassava vein mosaic virus (CsVMV), chlorophyll a/b binding protein, ribulose 1, 5-bisphosphate carboxylase, shoot-specific, root specific, chitinase, stress inducible, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells); animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, a baculovirus 1E1 promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell cc-actin, and the like. In a preferred embodiment of the invention, the promoter is selected from the group consisting of a cauliflower mosaic virus 35S promoter, a cassava vein mosaic virus promoter, and a cauliflower mosaic virus 35S minimal promoter, an elongation factor 1 alpha (EF 1) promoter, a phosphoglycerate kinase (PGK) promoter, a ubiquitin (Ubc) promoter, and an albumin promoter. In addition, these expression sequences may be modified by addition of enhancer or regulatory sequences and the like.

Enhancers that may be used in embodiments of the invention include but are not limited to: tobacco mosaic virus enhancer, cauliflower mosaic virus 35S enhancer, tobacco etch virus enhancer, ribulose 1,5-bisphosphate carboxylase enhancer, rice tungro bacilliform irus enhancer, an SV40 enhancer, a cytomegalovirus (CMV) enhancer, an elongation factor 1 (EF1) enhancer, yeast enhancers, other plant and viral gene enhancers, and the like.

Termination control regions, i.e., terminator or polyadenylation sequences, may also be derived from various genes native to the preferred hosts. Optionally, a termination site may be unnecessary, however, it is most preferred if included. In a preferred embodiment of the invention, the termination control region may be comprise or be derived from a synthetic sequence, synthetic polyadenylation signal, an SV40 late polyadenylation signal, an SV40 polyadenylation signal, a bovine growth hormone (BGH) polyadenylation signal, nopaline synthase (nos), cauliflower mosaic virus (CaMV), octopine synthase (ocs), Agrocateum, viral, and plant terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Regulatory region" means a nucleic acid sequence which regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" is a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

A "polypeptide" is a polymeric compound comprised of covalently linked amino acid residues. Amino acids have the following general structure:

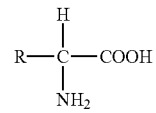

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. A polypeptide of the invention preferably comprises at least about 14 amino acids.

A "protein" is a polypeptide that performs a structural or functional role in a living cell.

An "isolated polypeptide" or "isolated protein" is a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

"Fragment" of a polypeptide according to the invention will be understood to mean a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of at least 2, 3, 4, 5, 6, 8, 10, 13, 14, 15, 16, 17, 18, 19, 20, 21, 22, 25, 26, 30, 35, 40, 45, 50, 100, 200, 240, or 300 amino acids.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c)

variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art. A variant polypeptide preferably comprises at least about 14 amino acids.

A "heterologous protein" refers to a protein not naturally produced in the cell.

A "mature protein" refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667.). Such proteins (and their encoding genes) have sequence homology, as reflected by their high degree of sequence similarity. However, in common usage and in the instant application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al., 1987, Cell 50:667).

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Sambrook et al., 1989, supra.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1× SSC, 0.1% SDS, 65° C. and washed with 2× SSC, 0.1% SDS followed by 0.1× SSC, 0.1% SDS), with the sequences exemplified herein. Substantially similar nucleic acid fragments of the instant invention are those nucleic acid fragments whose DNA sequences are at least 70% identical to the DNA sequence of the nucleic acid fragments reported herein. Preferred substantially nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Even more preferred are nucleic acid fragments that are at least 95% identical to the DNA sequence of the nucleic acid fragments reported herein.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

Gene Expression Modulation System of the Invention

Applicants have now shown that separating the transactivation and DNA binding domains by placing them on two different proteins results in greatly reduced background activity in the absence of a ligand and significantly increased activity over background in the presence of a ligand. Applicants' improved gene expression system comprises two chimeric gene expression; the first encoding a DNA binding domain fused to a nuclear receptor polypeptide and the second encoding a transactivation domain fused to a nuclear receptor polypeptide. The interaction of the first protein with the second protein effectively tethers the DNA binding domain to the transactivation domain. Since the DNA binding and transactivation domains reside on two different molecules, the background activity in the absence of ligand is greatly reduced.

In general, the inducible gene expression modulation system of the invention comprises a) a first chimeric gene that is capable of being expressed in a host cell comprising a polynucleotide sequence that encodes a first hybrid polypeptide comprising i) a DNA-binding domain that recognizes a response element associated with a gene whose expression is to be modulated; and ii) a ligand binding domain comprising the ligand binding domain from a nuclear receptor; and b) a second chimeric gene that is capable of being expressed in the host cell comprising a polynucleotide sequence that encodes a second hybrid polypeptide comprising: i) a transactivation domain; and ii) a ligand binding domain comprising the ligand binding domain from a nuclear receptor other than ultraspiracle (USP). In a specific embodiment, the gene expression modulation system comprises a DNA binding domain and a transactivation domain from a polypeptide other than a Group H nuclear receptor, an ecdysone receptor, a Group B nuclear receptor, a retinoid X receptor, or an ultraspiracle receptor. In another specific embodiment, the ligand binding domains from the first polypeptide and the second polypeptide are different and dimerize.

This two-hybrid system exploits the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). This two-hybrid system is a significantly improved inducible gene expression modulation system compared to the two systems disclosed in International Patent Applications PCT/US97/05330 and PCT/US98/14215.

The EcR is a member of the nuclear receptor superfamily and classified into subfamily 1, group H (referred to herein as "Group H nuclear receptors"). The members of each group share 40–60% amino acid identity in the E (ligand binding) domain (Laudet et al., A Unified Nomenclature System for the Nuclear Receptor Subfamily, 1999; Cell 97:161-163). In addition to the ecdysone receptor, other members of this nuclear receptor subfamily 1, group H include: ubiquitous receptor (UR), Orphan receptor 1 (OR-1), steroid hormone nuclear receptor 1 (NER-1), RXR interacting protein-15 (RIP-15), liver x receptor β (LXRβ), steroid hormone receptor like protein (RLD-1), liver x receptor (LXR), liver x receptor α (LXRα), farnesoid x receptor (FXR), receptor interacting protein 14 (RIP-14), and farnesol receptor (HRR-1).

Given the close relatedness of ecdysone receptor to other Group H nuclear receptors, Applicants' improved two-hybrid ecdysone receptor-based gene expression system is also expected to work when the ligand binding domains of other Group H nuclear receptors and their respective dimerization partners (Group B nuclear receptors) are used in place of EcR and RXR, respectively. One of ordinary skill in the art is able to make and use a Group H nuclear receptor-based gene expression system based upon Applicants' discovery and disclosure provided herein. Thus, Applicants' invention also provides a two-hybrid Group H nuclear receptor-based gene expression system that is useful in gene modulation for various applications including gene therapy, expression of proteins of interest in host cells, production of transgenic organisms, and cell-based assays.

RXR is a member of the nuclear receptor superfamily and classified into subfamily 2, Group B (referred to herein as "Group B nuclear receptors"). The members of each group share 40–60% amino acid identity in the E (ligand binding) domain (Laudet et al., A Unified Nomenclature System for the Nuclear Receptor Subfamily, 1999; Cell 97:161–163). In addition to the retinoid X receptor, other members of this nuclear receptor subfamily 2, Group B include: H-2 region II binding protein (H-2RIIBP), nuclear receptor co-regulator-I (RCoR-1), ultraspiracle (USP), 2C1, and chorion factor 1 (CF-1).

The nuclear receptor-based gene expression modulation system of the invention may be either heterodimeric and homodimeric. A functional EcR complex generally refers to a heterodimeric protein complex consisting of two members of the steroid receptor family, an ecdysone receptor protein obtained from various insects, and an ultraspiracle (USP) protein or the vertebrate homolog of USP, retinoid X receptor protein (see Yao, et al. (1993) Nature 366, 476–479; Yao, et al., (1992) Cell 71, 63–72). However, the complex may also be a homodimer as detailed below. The functional ecdysteroid receptor complex may also include additional protein(s) such as immunophilins. Additional members of the steroid receptor family of proteins, known as transcriptional factors (such as DHR38 or betaFTZ-1), may also be ligand dependent or independent partners for EcR, USP, and/or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP140, TIF1, RAP46/Bag-1, ARA70, SRC-1/NCoA-1, TIF2/GRIP/NCoA-2, ACTR/AIB1/RAC3/pCIP as well as the promiscuous coactivator C response element B binding protein, CBP/p300 (for review see Glass et al, Curr. Opin. Cell Biol. 9:222–232, 1997). Also, protein cofactors generally known as corepressors (also known as repressors, silencers, or silencing mediators) may be required to effectively inhibit transcriptional activation in the absence of ligand. These corepressors may interact with the unliganded ecdysone receptor to silence the activity at the response element. Current evidence suggests that the binding of ligand changes the conformation of the receptor, which results in release of the corepressor and recruitment of the above described coactivators, thereby abolishing their silencing activity. Examples of corepressors include N-CoR and SMRT (for review, see Horwitz et al. Mol Endocrinol. 10: 1167–1177, 1996). These cofactors may either be endogenous within the cell or organism, or may be added exogenously as transgenes to be expressed in either a regulated or unregulated fashion. Homodimer complexes of the ecdysone receptor protein, USP, or RXR may also be functional under some circumstances.

The ecdysone receptor complex typically includes proteins that are members of the nuclear receptor superfamily wherein all members are generally characterized by the presence of an amino-terminal transactivation domain, a DNA binding domain ("DBD"), and a ligand binding domain ("LBD") separated from the DBD by a hinge region. As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (see U.S. Pat. No. 4,981,784 and Evans, Science 240:889-895 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins. The EcR receptor, like a subset of the steroid receptor family, also possesses less well defined regions responsible for heterodimerization properties. Because the domains of nuclear receptors are modular in nature, the LBD, DBD, and transactivation domains may be interchanged.

Gene switch systems are known that incorporate components from the ecdysone receptor complex. However, in these known systems, whenever EcR is used it is associated with native or modified DNA binding domains and transactivation domains on the same molecule. USP or RXR are typically used as silent partners. We have now shown that when DNA binding domains and transactivation domains are on the same molecule the background activity in the absence of ligand is high and that such activity is dramatically reduced when DNA binding domains and transactivation domains are on different molecules, that is, on each of two partners of a heterodimeric or homodimeric complex.

This two-hybrid system also provides improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provide higher activity at a lower concentration. In addition, since transactivation based on EcR gene switches is often cell-line dependent, it is easier to tailor switching system to obtain maximum transactivation capability for each application. Furthermore, this two-hybrid system avoids some side effects due to overexpression of RXR that often occur when unmodified RXR is used as a switching partner. In this two-hybrid system, native DNA binding and transactivation domains of EcR or RXR are eliminated. As a result, these chimeric molecules have less chance of interacting with other steroid hormone receptors present in the cell resulting in reduced side effects.

Specifically, Applicants' invention relates to a gene expression modulation system comprising: a) a first gene expression cassette that is capable of being expressed in a host cell, wherein the first gene expression cassette comprises a polynucleotide that encodes a first polypeptide comprising i) a DNA-binding domain that recognizes a response element associated with a gene whose expression is to be modulated; and ii) a ligand binding domain comprising a ligand binding domain from a nuclear receptor; and b) a second gene expression cassette that is capable of being expressed in the host cell, wherein the second gene expression cassette comprises a polynucleotide sequence that encodes a second polypeptide comprising i) a transactivation domain; and ii) a ligand binding domain comprising a ligand binding domain from a nuclear receptor other than ultraspiracle (USP). In a specific embodiment, the gene expression modulation system comprises a DNA binding domain and a transactivation domain from a polypeptide other than a Group H nuclear receptor, an ecdysone receptor, a Group B nuclear receptor, a retinoid X receptor, or an ultraspiracle receptor. In another specific embodiment, the ligand binding domains from the first polypeptide and the second polypeptide are different and dimerize.

The present invention also relates to a gene expression modulation system according to the present invention further comprising c) a third gene expression cassette comprising: i) the response element to which the DNA-binding domain of the first polypeptide binds; ii) a promoter that is activated by the transactivation domain of the second polypeptide; and iii) the gene whose expression is to be modulated. In a specific embodiment, the gene whose expression is to be modulated is a homologous gene with respect to the host cell. In another specific embodiment, the gene whose expression is to be modulated is a heterologous gene with respect to the host cell.

In a specific embodiment, the ligand binding domain of the first polypeptide comprises a ligand binding domain selected from the group consisting of an ecdysone receptor, ubiquitous receptor (UR), Orphan receptor 1 (OR-1), steroid hormone nuclear receptor 1 (NER-1), RXR interacting protein-15 (RIP-15), liver x receptor β (LXRβ), steroid hormone receptor like protein (RLD-1), liver x receptor (LXR), liver x receptor α (LXRα), farnesoid x receptor (FXR), receptor interacting protein 14 (RIP-14), and farnesol receptor (HRR-1). In another specific embodiment, the ligand binding domain of the second polypeptide comprises a ligand binding domain selected from the group consisting of a retinoid X receptor, an H-2 region II binding protein (H-2RIIBP), a nuclear receptor co-regulator-1 (RCoR-1), an ultraspiracle (USP), a 2C1, and a chorion factor 1 (CF-1).

In a specific embodiment, the ligand binding domain of the first polypeptide comprises a Group H nuclear receptor ligand binding domain. Preferably, the ligand binding domain of the first polypeptide comprises an ecdysone receptor (EcR) ligand binding domain.

In another specific embodiment, ligand binding domain of the second polypeptide comprises a Group B nuclear receptor ligand binding domain. Preferably, the ligand binding domain of the second polypeptide comprises a retinoid X receptor (RXR) ligand binding domain.

In a preferred embodiment, when the ligand binding domain is an ecdysone receptor ligand binding domain, the other ligand binding domain ("partner") may be from a vertebrate retinoid X receptor (RXR). The "partner" ligand binding domain may further comprise a truncation mutation, a deletion mutation, a substitution mutation, or another modification.

In a specific embodiment, the ligand binding domain of the first polypeptide comprises a Group B nuclear receptor ligand binding domain.

In another specific embodiment, the ligand binding domain of the first polypeptide comprises a ligand binding domain selected from the group consisting of a retinoid X receptor, an H-2 region II binding protein (H-2RIIBP), a nuclear receptor co-regulator-1 (RCoR-1), an ultraspiracle (USP), a 2C1, and a chorion factor 1 (CF-1). Preferably, the ligand binding domain of the first polypeptide comprises a retinoid X receptor ligand binding domain.

In a specific embodiment, the ligand binding domain of the second polypeptide comprises a Group H nuclear receptor ligand binding domain.

In a specific embodiment, the ligand binding domain of the second polypeptide comprises a ligand binding domain selected from the group consisting of an ecdysone receptor, ubiquitous receptor (UR), Orphan receptor 1 (OR-1), steroid hormone nuclear receptor 1 (NER-1), RXR interacting protein-15 (RIP-15), liver x receptor β (LXRβ), steroid hormone receptor like protein (RLD-1), liver x receptor (LXR), liver x receptor α (LXRα), farnesoid x receptor (FXR), receptor interacting protein 14 (RIP-14), and farnesol receptor (HRR-1). Preferably, the ligand binding domain of the second polypeptide comprises an ecdysone receptor ligand binding domain.

In a preferred embodiment, the ligand binding domain of the first polypeptide comprises an ecdysone receptor ligand binding domain, and the ligand binding domain of the second polypeptide comprises a retinoid X receptor ligand binding domain.

In another preferred embodiment, the ligand binding domain of the first polypeptide is from a retinoid X receptor polypeptide, and the ligand binding domain of the second polypeptide is from an ecdysone receptor polypeptide. Preferably, the ligand binding domain is an EcR or RXR related steroid/thyroid hormone nuclear receptor family member ligand binding domain, or analogs, combinations, or modifications thereof. More preferably, the LBD is from EcR or RXR. Even more preferably, the LBD is from a truncated EcR or RXR. A truncation mutation may be made by any method used in the art, including but not limited to restriction endonuclease digestion/deletion, PCR-mediated/oligonucleotide-directed deletion, chemical mutagenesis, UV strand breakage, and the like.

Preferably, the EcR is an insect EcR selected from the group consisting of a Lepidopteran EcR, a Dipteran EcR, an Arthropod EcR, a Homopteran EcR and a Hemipteran EcR. More preferably, the EcR for use is a spruce budworm *Choristoneura fumiferana* EcR ("CfEcR"), a *Tenebrio moli-* tor EcR ("TmEcR"), a *Manduca sexta* EcR ("MsEcR"), a *Heliothies virescens* EcR ("HvEcR"), a silk moth *Bombyx mori* EcR ("BmEcR"), a fruit fly *Drosophila melanogaster* EcR ("DmEcR"), a mosquito *Aedes aegypti* EcR ("AaEcR"), a blowfly *Lucilia capitata* EcR ("LcEcR"), a Mediterranean fruit fly *Ceratitis capitata* EcR ("CcEcR"), a locust *Locusta migratoria* EcR ("LmEcR"), an aphid *Myzus persicae* EcR ("MpEcR"), a fiddler crab *Uca pugilator* EcR ("UpEcR"), an ixodid tick *Amblyomma americanum* EcR ("AmaEcR"), a white fly *Bamecia argentifoli* EcR ("BaEcR"; Zhang et al., co-pending US provisional patent application filed Sep. 26, 2001, incorporated herein by reference in its entirety), or a green leafhopper Nephotetix cincticeps EcR ("NcEcR"; Palli, co-pending US provisional patent application filed Sep. 26, 2001, incorporated herein by reference in its entirety). Even more preferably, the LBD is from spruce budworm (*Choristoneura fumiferana*) EcR ("CfEcR") or fruit fly *Drosophila melanogaster* EcR ("DmEcR").

Preferably, the LBD is from a truncated insect EcR. The insect EcR polypeptide truncation comprises a deletion of at least 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, or 265 amino acids. More preferably, the insect EcR polypeptide truncation comprises a deletion of at least a partial polypeptide domain. Even more preferably, the insect EcR polypeptide truncation comprises a deletion of at least an entire polypeptide domain. In a specific embodiment, the insect EcR polypeptide truncation comprises a deletion of at least an A/B-domain deletion, a C-domain deletion, a D-domain deletion, an E-domain deletion, an F-domain deletion, an A/B/C-domains deletion, an A/B/½-C-domains deletion, an A/B/C/D-domains deletion, an A/B/C/D/F-domains deletion, an A/B/F-domains, and an A/B/C/F-domains deletion. A combination of several complete and/or partial domain deletions may also be performed.

In a preferred embodiment, the ecdysone receptor ligand binding domain is encoded by a polynucleotide comprising a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

In another preferred embodiment, the ecdysone receptor ligand binding domain comprises a polypeptide sequence selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

Preferably, the vertebrate RXR ligand binding domain is from a human *Homo sapiens*, mouse *Mus musculus*, rat *Rattus norvegicus*, chicken *Gallus gallus*, pig *Sus scrofa domestica*, frog *Xenopus laevis*, zebrafish *Danio rerio*, tunicate *Polyandrocarpa misakiensis*, or jellyfish *Tripedalia cysophora* RXR. More preferably, the vertebrate RXR ligand binding domain is from a mouse *Mus musculus* RXR ("MmRXR") or a human Homo sapiens RXR "HsRXR"). The vertebrate RXR ligand binding domain is from an $RXR_\alpha$, $RXR_\beta$, or $RXR_\gamma$ isoform.

Preferably, the LBD is from a truncated vertebrate RXR. The RXR polypeptide truncation comprises a deletion of at least 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, or 265 amino acids. More preferably, the RXR polypeptide truncation comprises a deletion of at least a partial polypeptide domain. Even more preferably, the RXR polypeptide truncation comprises a deletion of at least an entire polypeptide domain. In a specific embodiment, the RXR polypeptide truncation comprises a deletion of at least an A/B-domain deletion, a C-domain deletion, a D-domain deletion, an E-domain deletion, an F-domain deletion, an A/B/C-domains deletion, an A/B/½-C-domains deletion, an A/B/C/D-domains deletion, an A/B/C/D/F-domains deletion, an A/B/F-domains, and an A/B/C/F-domains deletion. A combination of several complete and/or partial domain deletions may also be performed.

In a preferred embodiment, the retinoid X receptor ligand binding domain is encoded by a polynucleotide comprising a nucleic acid sequence selected from the group consisting of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30.

In another preferred embodiment, the retinoid X receptor ligand binding domain comprises a polypeptide sequence selected from the group consisting of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40.

The DNA binding domain can be any DNA binding domain with a known response element, including synthetic and chimeric DNA binding domains, or analogs, combinations, or modifications thereof. Preferably, the DBD is a GAL4 DBD, a LexA DBD, a transcription factor DBD, a Group H nuclear receptor member DBD, a steroid/thyroid hormone nuclear receptor superfamily member DBD, or a bacterial LacZ DBD. More preferably, the DBD is an EcR DBD [SEQ ID NO: 41 (polynucleotide) or SEQ ID NO: 42 (polypeptide)], a GAL4 DBD [SEQ ID NO: 43 (polynucleotide) or SEQ ID NO: 44 (polypeptide)], or a LexA DBD [(SEQ ID NO: 45 (polynucleotide) or SEQ ID NO: 46 (polypeptide)].

The transactivation domain (abbreviated "AD" or "TA") may be any Group H nuclear receptor member AD, steroid/thyroid hormone nuclear receptor AD, synthetic or chimeric AD, polyglutamine AD, basic or acidic amino acid AD, a VP16 AD, a GAL4 AD, an NF-κB AD, a BP64 AD, a B42 acidic activation domain (B42AD), a p65 transactivation domain (p65AD), or an analog, combination, or modification thereof. In a specific embodiment, the AD is a synthetic or chimeric AD, or is obtained from an EcR, a glucocorticoid receptor, VP16, GAL4, NF-kB, or B42 acidic activation domain AD. Preferably, the AD is an EcR AD [SEQ ID NO: 47 (polynucleotide) or SEQ ID NO: 48 (polypeptide)], a VP16 AD [SEQ ID NO: 49 (polynucleotide) or SEQ ID NO: 50 (polypeptide)], a B42 AD [SEQ ID NO: 51 (polynucleotide) or SEQ ID NO: 52 (polypeptide)], or a p65 AD [SEQ ID NO: 53 (polynucleotide) or SEQ ID NO: 54 (polypeptide)].

In a specific embodiment, the gene expression cassette encodes a hybrid polypeptide comprising either a) a DNA-binding domain encoded by a polynucleotide comprising a nucleic acid sequence of SEQ ID NO: 41, SEQ ID NO: 43, or SEQ ID NO: 45, or b) a transactivation domain encoded by a polynucleotide comprising a nucleic acid sequence of SEQ ID NO: 47, SEQ ID NO: 49, SEQ ID NO: 51, or SEQ ID NO: 53; and a Group H nuclear receptor ligand binding domain encoded by a polynucleotide according to the invention. Preferably, the Group H nuclear receptor ligand binding domain is an ecdysone receptor ligand binding domain encoded by a polynucleotide according to the invention.

In another specific embodiment, the gene expression cassette encodes a hybrid polypeptide comprising either a) a DNA-binding domain comprising an amino acid sequence of SEQ ID NO: 42, SEQ ID NO: 44, or SEQ ID NO: 46, or b) a transactivation domain comprising an amino acid sequence of SEQ ID NO: 48, EQ ID NO: 50, SEQ ID NO: 52, or SEQ ID NO: 54; and a Group H nuclear receptor ligand binding domain according to the invention. Preferably, the Group H nuclear receptor ligand binding domain is an ecdysone receptor ligand binding domain according to the invention.

The response element ("RE") may be any response element with a known DNA binding domain, or an analog, combination, or modification thereof. A single RE may be employed or multiple REs, either multiple copies of the same RE or two or more different REs, may be used in the present invention. In a specific embodiment, the RE is an RE from GAL4 ("GAL4RE"), LexA, a Group H nuclear receptor RE, a steroid/thyroid hormone nuclear receptor RE, or a synthetic RE that recognizes a synthetic DNA binding domain. Preferably, the RE is an ecdysone response element (EcRE) comprising a polynucleotide sequence of SEQ ID NO: 55, a GAL4RE comprising a polynucleotide sequence of SEQ ID NO: 56, or a LexA RE (operon, "op") comprising a polynucleotide sequence of SEQ ID NO: 57 ("2XLexAo-pRE").

Preferably, the first hybrid protein is substantially free of a transactivation domain and the second hybrid protein is substantially free of a DNA binding domain. For purposes of this invention, "substantially free" means that the protein in question does not contain a sufficient sequence of the domain in question to provide activation or binding activity.

The ligands for use in the present invention as described below, when combined with the ligand binding domain of an EcR, USP, RXR, or another polypeptide which in turn are bound to the response element linked to a gene, provide the means for external temporal regulation of expression of the gene. The binding mechanism or the order in which the various components of this invention bind to each other, that is, for example, ligand to ligand binding domain, DNA-binding domain to response element, transactivation domain to promoter, etc., is not critical. Binding of the ligand to the ligand binding domains of an EcR, USP, RXR, or another protein, enables expression or suppression of the gene. This mechanism does not exclude the potential for ligand binding to EcR, USP, or RXR, and the resulting formation of active homodimer complexes (e.g. EcR+EcR or USP+USP). Preferably, one or more of the receptor domains can be varied producing a chimeric gene switch. Typically, one or more of the three domains, DBD, LBD, and transactivation domain, may be chosen from a source different than the source of the other domains so that the chimeric genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski, et al. (1988) Nature, 335:563–564) or LexA protein from *E. coli* (see Brent and Ptashne (1985), Cell, 43:729–736), or synthetic response elements specific for targeted interactions with proteins designed, modified, and selected for such specific interactions (see, for example, Kim, et al. (1997), *Proc. Natl. Acad. Sci., USA*, 94:3616–3620) to accommodate chimeric receptors. Another advantage of chimeric systems is that they allow choice of a promoter used to drive the gene expression according to a desired end result. Such double control can be particularly important in areas of gene therapy, especially when cytotoxic proteins are produced, because both the timing of expression as well as the cells wherein expression occurs can be controlled. When genes, operatively linked to a suitable promoter, are introduced into the cells of the subject, expression of the exogenous genes is controlled by the presence of the system of this invention. Promoters may be constitutively or inducibly regulated or may be tissue-specific (that is, expressed only in a particular type of cells) or specific to certain developmental stages of the organism.

Gene Expression Cassettes of the Invention

The novel nuclear receptor-based inducible gene expression system of the invention comprises a novel gene expression cassette that is capable of being expressed in a host cell, wherein the gene expression cassette comprises a polynucleotide encoding a hybrid polypeptide. Thus, Applicants' invention also provides novel gene expression cassettes for use in the gene expression system of the invention.

Specifically, the present invention provides a gene expression cassette comprising a polynucleotide encoding a hybrid polypeptide. The hybrid polypeptide comprises either 1) a DNA-binding domain that recognizes a response element and a ligand binding domain of a nuclear receptor or 2) a transactivation domain and a ligand binding domain of a nuclear receptor. In a specific embodiment, the ligand binding domain is from a Group H nuclear receptor, an ecdysone receptor, a Group B nuclear receptor, or a retinoid X receptor. In another specific embodiment, the ligand binding domain and the transactivation domain are from a nuclear receptor other than a Group H nuclear receptor, an EcR, a Group B nuclear receptor, an RXR, or a USP.

In a specific embodiment, the gene expression cassette encodes a hybrid polypeptide comprising a DNA-binding domain that recognizes a response element and an ecdysone receptor ligand binding domain, wherein the DNA binding domain is from a nuclear receptor other than an ecdysone receptor.

In another specific embodiment, the gene expression cassette encodes a hybrid polypeptide comprising a DNA-binding domain that recognizes a response element and a retinoid X receptor ligand binding domain, wherein the DNA binding domain is from a nuclear receptor other than a retinoid X receptor.

In another specific embodiment, the gene expression cassette encodes a hybrid polypeptide comprising a transactivation domain and an ecdysone receptor ligand binding domain, wherein the transactivation domain is from a nuclear receptor other than an ecdysone receptor.

In another specific embodiment, the gene expression cassette encodes a hybrid polypeptide comprising a transactivation domain and a retinoid X receptor ligand binding domain, wherein the transactivation domain is from a nuclear receptor other than a retinoid X receptor.

Preferably, the ligand binding domain is an EcR or RXR related steroid/thyroid hormone nuclear receptor family member ligand binding domain, or analogs, combinations, or modifications thereof. More preferably, the LBD is from EcR or RXR. Even more preferably, the LBD is from a truncated EcR or RXR.

Preferably, the EcR is an insect EcR selected from the group consisting of a Lepidopteran EcR, a Dipteran EcR, an Arthropod EcR, a Homopteran EcR and a Hemipteran EcR. More preferably, the EcR for use is a spruce budworm *Choristoneura fumiferana* EcR ("CfEcR"; Kothapalli et al., 1995 Dev Genet. 17:319–30), a yellow meal worm *Tenebrio*

*molitor* EcR ("TmEcR"; Mouillet et al., 1997, Eur. J. Biochem. 248:856–863), a tobacco hormworm *Manduca sexta* EcR ("MsEcR"; Fujiwara et al., 1995, Insect Biochem. Molec. Biol. 25, 845–856), a tobacco budworm *Heliothies virescens* EcR ("HvEcR"; Martinez et al., 1999, *Insect Biochem Mol Biol.* 29:915–30), a golmidge *Chironomus tentans* EcR ("CtEcR"; Imhof et al., 1993, Insect Biochem. Molec. Biol. 23, 115–124), a silkworm *Bombyx mori* EcR ("BmEcR"; Swevers et al., 1995, Insect Biochem. Molec. Biol. 25, 857–866), a squinting bush brown *Bicyclus anynana* EcR ("BanEcR"), a buckeye *Junonia coenia* EcR ("JcEcR"), a fruit fly *Drosophila melanogaster* EcR ("DmEcR"; Koelle et al., 1991, Cell 67, 59–77), a yellow fever mosquito *Aedes aegypti* EcR ("AaEcR"; Cho et al., 1995, Insect Biochem. Molec. Biol. 25, 19–27), a blowfly *Lucilia capitata* ("LcEcR"), a sheep blowfly *Lucilia cuprina* EcR ("LucEcR"; Hannan and Hill, 1997, Insect Biochem. Molec. Biol. 27, 479–488), a blowfly *Calliphora vicinia* EcR ("CvEcR"), a Mediterranean fruit fly *Ceratitis capitata* EcR ("CcEcR"; Verras et al., 1999, Eur J Biochem. 265: 798–808), a locust *Locusta migratoria* EcR ("LmEcR"; Saleh et al., 1998, Mol Cell Endocrinol. 143:91–9), an aphid *Myzus persicae* EcR ("MpEcR"; International Patent Application Publication WO99/36520), a fiddler crab *Celuca pugilator* EcR ("CpEcR"; Chung et al., 1998, Mol Cell Endocrinol 139:209–27), an ixodid tick *Amblyomma americanum* EcR ("AmaEcR"; Guo et al., 1997, Insect Biochem. Molec. Biol. 27, 945–962), a white fly *Bamecia argentifoli* ("BaEcR"; Zhang et al., co-pending US provisional patent application filed Sep. 26, 2001, incorporated herein by reference in its entirety), or a green leafhopper *Nephotetix cincticeps* ("NcEcR"; Palli, co-pending US provisional patent application filed Sep. 26, 2001, incorporated herein by reference in its entirety). Even more preferably, the LBD is from spruce budworm (*Choristoneura fumiferana*) EcR ("CfEcR") or fruit fly *Drosophila melanogaster* EcR ("DmEcR").

Preferably, the LBD is from a truncated insect EcR. The insect EcR polypeptide truncation comprises a deletion of at least 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, or 265 amino acids. More preferably, the insect EcR polypeptide truncation comprises a deletion of at least a partial polypeptide domain. Even more preferably, the insect EcR polypeptide truncation comprises a deletion of at least an entire polypeptide domain. In a specific embodiment, the insect EcR polypeptide truncation comprises a deletion of at least an A/B-domain deletion, a C-domain deletion, a D-domain deletion, an E-domain deletion, an F-domain deletion, an A/B/C-domains deletion, an A/B/½-C-domains deletion, an A/B/C/D-domains deletion, an A/B/C/D/F-domains deletion, an A/B/F-domains, and an A/B/C/F-domains deletion. A combination of several complete and/or partial domain deletions may also be performed.

In a preferred embodiment, the ecdysone receptor ligand binding domain is encoded by a polynucleotide comprising a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

In another preferred embodiment, the ecdysone receptor ligand binding domain comprises an amino acid sequence selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

Preferably, the RXR polypeptide is a mouse *Mus musculus* RXR ("MmRXR") or a human Homo sapiens RXR ("HsRXR"). The RXR polypeptide may be an $RXR_\alpha$, $RXR_\beta$, or $RXR_\gamma$ isoform.

Preferably, the LBD is from a truncated RXR. The RXR polypeptide truncation comprises a deletion of at least 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, or 265 amino acids. More preferably, the RXR polypeptide truncation comprises a deletion of at least a partial polypeptide domain. Even more preferably, the RXR polypeptide truncation comprises a deletion of at least an entire polypeptide domain. In a specific embodiment, the RXR polypeptide truncation comprises a deletion of at least an A/B-domain deletion, a C-domain deletion, a D-domain deletion, an E-domain deletion, an F-domain deletion, an A/B/C-domains deletion, an A/B/½-C-domains deletion, an A/B/C/D-domains deletion, an A/B/C/D/F-domains deletion, an A/B/F-domains, and an A/B/C/F-domains deletion. A combination of several complete and/or partial domain deletions may also be performed.

In a preferred embodiment, the retinoid X receptor ligand binding domain is encoded by a polynucleotide comprising a nucleic acid sequence selected from the group consisting of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30.

In another preferred embodiment, the retinoid X receptor ligand binding domain comprises an amino acid sequence selected from the group consisting of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40.

The DNA binding domain can be any DNA binding domain with a known response element, including synthetic and chimeric DNA binding domains, or analogs, combinations, or modifications thereof. Preferably, the DBD is a GAL4 DBD, a LexA DBD, a transcription factor DBD, a Group H nuclear receptor member DBD, a steroid/thyroid hormone nuclear receptor superfamily member DBD, or a bacterial LacZ DBD. More preferably, the DBD is an EcR DBD [SEQ ID NO: 41 (polynucleotide) or SEQ ID NO: 42 (polypeptide)], a GAL4 DBD [SEQ ID NO: 43 (polynucleotide) or SEQ ID NO: 44 (polypeptide)], or a LexA DBD [(SEQ ID NO: 45 (polynucleotide) or SEQ ID NO: 46 (polypeptide)].

In a preferred embodiment, the gene expression cassette encodes a hybrid polypeptide comprising a DNA-binding domain encoded by a polynucleotide comprising a nucleic acid sequence selected from the group consisting of an EcR DBD (SEQ ID NO: 41), a GAL4 DBD (SEQ ID NO: 43), and a LexA DBD (SEQ ID NO: 45), and an ecdysone receptor ligand binding domain encoded by a polynucleotide comprising a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

In another preferred embodiment, the gene expression cassette encodes a hybrid polypeptide comprising a DNA-binding domain comprising a polypeptide sequence selected from the group consisting of an EcR DBD (SEQ ID NO: 42), a GAL4 DBD (SEQ ID NO: 44), and a LexA DBD (SEQ ID NO: 46), and an ecdysone receptor ligand binding domain comprising an amino acid sequence selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

In another preferred embodiment, the gene expression cassette encodes a hybrid polypeptide comprising a DNA-binding domain encoded by a polynucleotide comprising a nucleic acid sequence selected from the group consisting of an EcR DBD (SEQ ID NO: 41), a GAL4 DBD (SEQ ID NO: 43), and a LexA DBD (SEQ ID NO: 45), and a retinoid X receptor ligand binding domain encoded by a polynucleotide comprising a nucleic acid sequence selected from the group consisting of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30.

In another preferred embodiment, the gene expression cassette encodes a hybrid polypeptide comprising a DNA-binding domain comprising a polypeptide sequence selected from the group consisting of an EcR DBD (SEQ ID NO: 42), a GAL4 DBD (SEQ ID NO: 44), and a LexA DBD (SEQ ID NO: 46), and a retinoid X receptor ligand binding domain comprising an amino acid sequence selected from the group consisting of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40.

The transactivation domain (abbreviated "AD" or "TA") may be any Group H nuclear receptor member AD, steroid/thyroid hormone nuclear receptor AD, synthetic or chimeric AD, polyglutamine AD, basic or acidic amino acid AD, a VP16 AD, a GAL4 AD, an NF-κB AD, a BP64 AD, a B42 acidic activation domain (B42AD), a p65 transactivation domain (p65AD), or an analog, combination, or modification thereof. In a specific embodiment, the AD is a synthetic or chimeric AD, or is obtained from an EcR, a glucocorticoid receptor, VP16, GAL4, NF-kB, or B42 acidic activation domain AD. Preferably, the AD is an EcR AD [SEQ ID NO: 47 (polynucleotide) or SEQ ID NO: 48 (polypeptide)], a VP16 AD [SEQ ID NO: 49 (polynucleotide) or SEQ ID NO: 50 (polypeptide)], a B42 AD [SEQ ID NO: 51 (polynucleotide) or SEQ ID NO: 52 (polypeptide)], or a p65 AD [SEQ ID NO: 53 (polynucleotide) or SEQ ID NO: 54 (polypeptide)].

In a specific embodiment, the gene expression cassette encodes a hybrid polypeptide comprising either a) a DNA-binding domain encoded by a polynucleotide comprising a nucleic acid sequence of SEQ ID NO: 41, SEQ ID NO: 43, or SEQ ID NO: 45, or b) a transactivation domain encoded by a polynucleotide comprising a nucleic acid sequence of SEQ ID NO: 47, SEQ ID NO: 49, SEQ ID NO: 51, or SEQ ID NO: 53; and a Group H nuclear receptor ligand binding domain encoded by a polynucleotide according to the invention. Preferably, the Group H nuclear receptor ligand binding domain is an ecdysone receptor ligand binding domain encoded by a polynucleotide according to the invention.

In another specific embodiment, the gene expression cassette encodes a hybrid polypeptide comprising either a) a DNA-binding domain comprising an amino acid sequence of SEQ ID NO: 42, SEQ ID NO: 44, or SEQ ID NO: 46, or b) a transactivation domain comprising an amino acid sequence of SEQ ID NO: 48, SEQ ID NO: 50, SEQ ID NO: 52, or SEQ ID NO: 54; and a Group H nuclear receptor ligand binding domain according to the invention. Preferably, the Group H nuclear receptor ligand binding domain is an ecdysone receptor ligand binding domain according to the invention.

In a preferred embodiment, the gene expression cassette encodes a hybrid polypeptide comprising a transactivation domain encoded by a polynucleotide comprising a nucleic acid sequence of SEQ ID NO: 47, SEQ ID NO: 49, SEQ ID NO: 51, or SEQ ID NO: 53, and an ecdysone receptor ligand binding domain encoded by a polynucleotide comprising a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

In another preferred embodiment, the gene expression cassette encodes a hybrid polypeptide comprising a transactivation domain comprising a polypeptide sequence of SEQ ID NO: 48, SEQ ID NO: 50, SEQ ID NO: 52, or SEQ ID NO: 54, and an ecdysone receptor ligand binding domain comprising a polypeptide sequence selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

In another preferred embodiment, the gene expression cassette encodes a hybrid polypeptide comprising a transactivation domain encoded by a polynucleotide comprising a nucleic acid sequence of SEQ ID NO: 47, SEQ ID NO: 49, SEQ ID NO: 51, or SEQ ID NO: 53, and a retinoid X receptor ligand binding domain encoded by a polynucleotide comprising a nucleic acid sequence selected from the group consisting of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30.

In another preferred embodiment, the gene expression cassette encodes a hybrid polypeptide comprising a transactivation domain comprising a polypeptide sequence of SEQ ID NO: 48, SEQ ID NO: 50, SEQ ID NO: 52, or SEQ ID NO: 54, and a retinoid X receptor ligand binding domain comprising an amino acid sequence selected from the group consisting of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40.

The present invention also provides a gene expression cassette comprising: i) a response element comprising a domain recognized by a polypeptide comprising a DNA binding domain; ii) a promoter that is activated by a polypeptide comprising a transactivation domain; and iii) a gene whose expression is to be modulated.

The response element ("RE") may be any response element with a known DNA binding domain, or an analog, combination, or modification thereof. A single RE may be employed or multiple REs, either multiple copies of the same RE or two or more different REs, may be used in the present invention. In a specific embodiment, the RE is an RE from GAL4 ("GAL4RE"), LexA, a Group H nuclear receptor RE, a steroid/thyroid hormone nuclear receptor RE, or a synthetic RE that recognizes a synthetic DNA binding domain. Preferably, the RE is an ecdysone response element (EcRE) comprising a polynucleotide sequence of SEQ ID NO: 55, a GAL4RE comprising a polynucleotide sequence of SEQ ID NO: 56, or a LexA RE (operon, "op") comprising a polynucleotide sequence of SEQ ID NO: 57 ("2XLexAopRE").

Preferably, the first hybrid protein is substantially free of a transactivation domain and the second hybrid protein is substantially free of a DNA binding domain. For purposes of this invention, "substantially free" means that the protein in question does not contain a sufficient sequence of the domain in question to provide activation or binding activity.

A steroid/thyroid hormone nuclear receptor DNA binding domain, activation domain or response element according to the invention may be obtained from a steroid/thyroid hormone nuclear receptor selected from the group consisting of thyroid hormone receptor α (TRα), thyroid receptor 1 (c-erbA-1), thyroid hormone receptor α (THRA), thyroid hormone receptor β (TRβ), thyrpid hormone receptor β (THRB), retinoic acid receptor α (RARα), retinoic acid receptor β (RARβ), hepatoma (HAP), retinoic acid receptor γ (RARγ), retinoic acid recetor gamma-like (RARD), peroxisome proliferator-activated receptor α (PPARα), peroxisome proliferator-activated receptor β (PPARβ), peroxisome proliferator-activator related receptor (NUC-1), peroxisome proliferator-activated receptor δ (PPARδ), peroxisome proliferator-activator related receptor (FFAR), peroxisome proliferator-activated receptor γ (PPARγ), orphan receptor encoded by non-encoding strand of thyroid hormone receptor α (REVERBα), v-erb A related receptor (EAR-1), v-erb related receptor (EAR-1 A), γ), orphan receptor encoded by non-encoding strand of thyroid hormone receptor β (REVERBβ), v-erb related receptor (EAR-1β), orphan nuclear recptor BD73 (BD73), rev-erbA-related receptor (RVR), zinc finger protein 126 (HZF2), ecdysone-inducible protein E75 (E75), ecdysone-inducible protein E78 (E78), Drosophila receptor 78 (DR-78), retinoid-related orphan receptor α (RORα), retinoid Z receptor α (RZRα), retinoid related orphan receptor p (RORβ), retinoid Z receptor β (RZRβ), retinoid-related orphan receptor γ (RORγ), retinoid Z receptor γ (RZRγ), retinoid-related orphan receptor (TOR), hormone receptor 3 (HR-3), Drosophila hormone receptor 3 (DHR-3), myohemerythin (MHR-3), growth hormone receptor 3 (GHR-3), C. elegans nuclear receptor 3 (CNR-3), C. elegans hormone receptor 3 (CHR-3), C. elegans nuclear receptor 14 (CNR-14), ecdysone receptor (ECR), ubiquitous receptor (UR), orphan nuclear receptor (OR-1), NER-1, receptor-interacting protein 15 (RIP-15), liver X receptor β (LXRβ), steroid hormone receptor like protein (RLD-1), liver X receptor (LXR), liver X receptor α (LXRα), farnesoid X receptor (FXR), receptor-interacting protein 14 (RIP-14), HRR-1, vitamin D receptor (VDR), orphan nuclear receptor (ONR-1), pregnane X receptor (PXR), steroid and xenobiotic receptor (SXR), benzoate X receptor (BXR), nuclear receptor (MB-67), constitutive androstane receptor 1 (CAR-1), constitutive androstane receptor α (CARα), constitutive androstane receptor 2 (CAR-2), constitutive androstane receptor β (CARβ), Drosophila hormone receptor 96 (DHR-96), nuclear hormone receptor 1 (NHR-1), hepatocyte nuclear factor 4 (HNF-4), hepatocyte nuclear factor 4G (HNF-4G), hepatocyte nuclear factor 4B (HNF-4B), DHNF-4, hepatocyte nuclear factor 4D (HNF-4D), retinoid X receptor α (RXRα), retinoid X receptor β (RXRβ), H-2 region II binding protein (H-2RIIBP), nuclear receptor co-regulator-1 (RCOR-1), retinoid X receptor 7 (RXRy), Ultraspiracle (USP), 2C1, chorion factor 1 (CF-1), testicular receptor (TR-2), testicular receptor (TR2–11), TR4, TAK-1, Drosophila hormone receptor (DHR78), Tailless (TLL), tailless homolog (TLX), XTLL, chicken ovalbumin upstream promoter transcription factor I (COUP-TFI), chicken ovalbumin upstream promoter transcription factor A (COUP-TFA), EAR-3, SVP-44, chicken ovalbumin upstream promoter transcription factor II (COUP-TFII), chicken ovalbumin upstream promoter transcription factor B (COUP-TFB), ARP-1, SVP-40, SVP, chicken ovalbumin upstream promoter transcription factor III (COUP-TFIII), chicken ovalbumin upstream promoter transcription factor G (COUP-TFG), SVP-46, EAR-2, estrogen receptor α (ERα), estrogen receptor β (ERβ), estrogen related receptor 1 (ERR1), estrogen related receptor α (ERRα), estrogen related receptor 2 (ERR2), estrogen related receptor β (ERRβ), glucocorticoid receptor (GR), mineralocorticoid receptor (MR), progesterone receptor (PR), androgen receptor (AR), nerve growth factor induced gene B (NGFI-B), nuclear receptor similar to Nur-77 (TRS), N10, Orphan receptor (NUR-77), Human early response gene (NAK-1), Nurr related factor 1 (NURR-1), a human immediate-early response gene (NOT), regenerating liver nuclear receptor 1 (RNR-1), hematopoietic zinc finger 3 (HZF-3), Nur rekated protein-1 (TINOR), Nuclear orphan receptor 1 (NOR-1), NOR1 related receptor (MINOR), Drosophila hormone receptor 38 (DHR-38), C. elegans nuclear receptor 8 (CNR-8), C48D5, steroidogenic factor 1 (SF 1), endozepine-like peptide (ELP), fushi tarazu factor 1 (FTZ-F1), adrenal 4 binding protein (AD4BP), liver receptor homolog (LRH-1), Ftz-F1-related orphan receptor A (xFFrA), Ftz-F 1-related orphan receptor B (xFFrB), nuclear receptor related to LRH-1 (FFLR), nuclear receptor related to LRH-1 (PHR), fetoprotein transcriptin factor (FTF), germ cell nuclear factor (GCNFM), retinoid receptor-related testis-associated receptor (RTR), knirps (KNI), knirps related (KNRL), Embryonic gonad (EGON), Drosophila gene for ligand dependent nuclear receptor (EAGLE), nuclear receptor similar to trithorax (ODR7), Trithorax, dosage sensitive sex reversal adrenal hypoplasia congenita critical region chromosome X gene (DAX-1), adrenal hypoplasia congenita and hypogonadotropic hypogonadism (AHCH), and short heterodimer partner (SHP).

For purposes of this invention, Group H nuclear receptors, EcR and RXR also include synthetic and chimeric Group H nuclear receptors, EcR and RXR and their homologs.

Genes of interest for use in Applicants' gene expression cassettes may be endogenous genes or heterologous genes. Nucleic acid or amino acid sequence information for a desired gene or protein can be located in one of many public access databases, for example, GENBANK, EMBL, Swiss-Prot, and PIR, or in many biology related journal publications. Thus, those skilled in the art have access to nucleic acid sequence information for virtually all known genes. Such information can then be used to construct the desired constructs for the insertion of the gene of interest within the gene expression cassettes used in Applicants' methods described herein.

Examples of genes of interest for use in Applicants' gene expression cassettes include, but are not limited to: genes encoding therapeutically desirable polypeptides or products that may be used to treat a condition, a disease, a disorder, a dysfunction, a genetic defect, such as monoclonal antibodies, enzymes, proteases, cytokines, interferons, insulin, erthropoietin, clotting factors, other blood factors or components, viral vectors for gene therapy, virus for vaccines, targets for drug discovery, functional genomics, and proteomics analyses and applications, and the like.

Polynucleotides of the Invention

The novel two-hybrid inducible gene expression system of the invention comprises a gene expression cassette comprising a polynucleotide that encodes a nuclear receptor ligand binding domain. In a specific embodiment, the ligand binding domain is from a Group H nuclear receptor, an ecdysone receptor, a Group B nuclear receptor, or a retinoid X receptor. In a preferred embodiment, the two-hybrid inducible gene expression system is a two-hybrid ecdysone receptor-based inducible gene expression system of the invention comprising a gene expression cassette comprising a polynucleotide that encodes a ligand binding domain from an EcR or RXR polypeptide. Preferably, the polynucleotide encoding the ligand binding domain from an EcR or RXR polypeptide, is a polynucleotide encoding an EcR or RXR polypeptide comprising a truncation mutation. These gene expression cassettes and the polynucleotides they comprise are useful as components of a nuclear receptor-based gene expression system to modulate the expression of a gene within a host cell.

Thus, the present invention also relates to a polynucleotide that encodes a Group H nuclear receptor polypeptide comprising a truncation mutation, an ecdysone receptor polypeptide comprising a truncation mutation, a Group B nuclear receptor polypeptide comprising a truncation mutation, or a retinoid X receptor polypeptide comprising a truncation mutation. The present invention also relates to a polynucleotide that encodes an EcR or RXR polypeptide comprising a truncation mutation. Specifically, the present invention relates to an isolated polynucleotide encoding an EcR or RXR polypeptide comprising a truncation mutation that affects ligand binding activity or ligand sensitivity.

Preferably, the truncation mutation results in a polynucleotide that encodes a truncated EcR polypeptide or a truncated RXR polypeptide comprising a deletion of at least 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, or 265 amino acids. More preferably, the EcR or RXR polypeptide truncation comprises a deletion of at least a partial polypeptide domain. Even more preferably, the EcR or RXR polypeptide truncation comprises a deletion of at least an entire polypeptide domain. In a specific embodiment, the EcR or RXR polypeptide truncation comprises a deletion of at least an A/B-domain deletion, a C-domain deletion, a D-domain deletion, an E-domain deletion, an F-domain deletion, an A/B/C-domains deletion, an A/B/½-C-domains deletion, an A/B/C/D-domains deletion, an A/B/C/D/F-domains deletion, an A/B/F-domains, and an A/B/C/F-domains deletion. A combination of several complete and/or partial domain deletions may also be performed.

In a specific embodiment, the EcR polynucleotide according to the invention comprises a polynucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10. In a specific embodiment, the polynucleotide according to the invention encodes a ecdysone receptor polypeptide comprising an amino acid sequence selected from the group consisting of SEQ ID NO: 11 (CfEcR-CDEF), SEQ ID NO: 12 (CfEcR-½CDEF, which comprises the last 33 carboxy-terminal amino acids of C domain), SEQ ID NO: 13 (CfEcR-DEF), SEQ ID NO: 14 (CfEcR-EF), SEQ ID NO: 15 (CfEcR-DE), SEQ ID NO: 16 (DmEcR-CDEF), SEQ ID NO: 17 (DmEcR-½CDEF), SEQ ID NO: 18 (DmEcR-DEF), SEQ ID NO: 19 (DmEcR-EF), and SEQ ID NO: 20 (DmEcR-DE).

In another specific embodiment, the RXR polynucleotide according to the invention comprises a polynucleotide sequence selected from the group consisting of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30. In another specific embodiment, the polynucleotide according to the invention encodes a truncated RXR polypeptide comprising an amino acid sequence consisting of SEQ ID NO: 31 (MmRXR-CDEF), SEQ ID NO: 32 (MmRXR-DEF), SEQ ID NO: 33 (MmRXR-EF), SEQ ID NO: 34 (MmRXR-truncatedEF), SEQ ID NO: 35 (MmRXR-E), SEQ ID NO: 36 (HsRXR-CDEF), SEQ ID NO: 37 (HsRXR-DEF), SEQ ID NO: 38 (HsRXR-EF), SEQ ID NO: 39 (HsRXR-truncated EF), and SEQ ID NO: 40 (HsRXR-E).

In particular, the present invention relates to an isolated polynucleotide encoding an EcR or RXR polypeptide comprising a truncation mutation, wherein the mutation reduces ligand binding activity or ligand sensitivity of the EcR or RXR polypeptide. In a specific embodiment, the present invention relates to an isolated polynucleotide encoding an EcR or RXR polypeptide comprising a truncation mutation that reduces steroid binding activity or steroid sensitivity of the EcR or RXR polypeptide. In a preferred embodiment, the present invention relates to an isolated polynucleotide encoding an EcR polypeptide comprising a truncation mutation that reduces steroid binding activity or steroid sensitivity of the EcR polypeptide, wherein the polynucleotide comprises a nucleic acid sequence of SEQ ID NO: 3 (CfEcR-DEF), SEQ ID NO: 4 (CfEcR-EF), SEQ ID NO: 8 (DmEcR-DEF), or SEQ ID NO: 9 (DmEcR-EF). In another specific embodiment, the present invention relates to an isolated polynucleotide encoding an EcR or RXR polypeptide comprising a truncation mutation that reduces non-steroid binding activity or non-steroid sensitivity of the EcR or RXR polypeptide. In a preferred embodiment, the present invention relates to an isolated polynucleotide encoding an EcR polypeptide comprising a truncation mutation that reduces non-steroid binding activity or non-steroid sensitivity of the EcR polypeptide, wherein the polynucleotide comprises a nucleic acid sequence of SEQ ID NO: 4 (CfEcR-EF) or SEQ ID NO: 9 (DmEcR-EF).

The present invention also relates to an isolated polynucleotide encoding an EcR or RXR polypeptide comprising a truncation mutation, wherein the mutation enhances ligand binding activity or ligand sensitivity of the EcR or RXR polypeptide. In a specific embodiment, the present invention relates to an isolated polynucleotide encoding an EcR or RXR polypeptide comprising a truncation mutation that enhances steroid binding activity or steroid sensitivity of the EcR or RXR polypeptide. In another specific embodiment, the present invention relates to an isolated polynucleotide encoding an EcR or RXR polypeptide comprising a truncation mutation that enhances non-steroid binding activity or non-steroid sensitivity of the EcR or RXR polypeptide. In a preferred embodiment, the present invention relates to an isolated polynucleotide encoding an EcR polypeptide comprising a truncation mutation that enhances non-steroid binding activity or non-steroid sensitivity of the EcR polypeptide, wherein the polynucleotide comprises a nucleic acid sequence of SEQ ID NO: 3 (CfEcR-DEF) or SEQ ID NO: 8 (DmEcR-DEF).

The present invention also relates to an isolated polynucleotide encoding a retinoid X receptor polypeptide comprising a truncation mutation that increases ligand sensitivity of a heterodimer comprising the mutated retinoid X receptor polypeptide and a dimerization partner. Preferably, the isolated polynucleotide encoding a retinoid X receptor polypeptide comprising a truncation mutation that increases ligand sensitivity of a heterodimer comprises a polynucleotide sequence selected from the group consisting of SEQ ID NO: 23 (MmRXR-EF), SEQ ID NO: 24 (MmRXR-truncatedEF), SEQ ID NO: 28 (HsRXR-EF), or SEQ ID NO: 29 (HsRXR-truncated EF). In a specific embodiment, the dimerization partner is an ecdysone receptor polypeptide. Preferably, the dimerization partner is a truncated EcR polypeptide. More preferably, the dimerization partner is an EcR polypeptide in which domains A/B/C have been deleted. Even more preferably, the dimerization partner is an EcR polypeptide comprising an amino acid sequence of SEQ ID NO: 13 (CfEcR-DEF) or SEQ ID NO: 18 (DmEcR-DEF).

In addition, the present invention relates to an expression vector comprising a polynucleotide according the invention, operatively linked to a transcription regulatory element. Preferably, the polynucleotide encoding a ligand binding domain is operatively linked with an expression control sequence permitting expression of the ligand binding domain in an expression competent host cell. The expression control sequence may comprise a promoter that is functional in the host cell in which expression is desired. The vector may be a plasmid DNA molecule or a viral vector. Preferred viral vectors include retrovirus, adenovirus, adeno-associated virus, herpes virus, and vaccinia virus. The invention further relates to a replication defective recombinant virus comprising in its genome, the polynucleotide encoding a ligand binding domain as described above. Thus, the present invention also relates to an isolated host cell comprising such an expression vector, wherein the transcription regulatory element is operative in the host cell.

The present invention also relates to an isolated polypeptide encoded by a polynucleotide according to the invention.

Polypeptides of the Invention

The novel two-hybrid-based inducible gene expression system of the invention comprises at least one gene expression cassette comprising a polynucleotide that encodes a polypeptide comprising a nuclear receptor ligand binding domain. In a specific embodiment, the nuclear receptor ligand binding domain is from a Group H nuclear receptor, an ecdysone receptor, a Group B nuclear receptor, or a retinoid X receptor. In a preferred embodiment, the two-hybrid inducible gene expression system is a two-hybrid ecdysone receptor-based inducible gene expression system of the invention comprising a gene expression cassette comprising a polynucleotide that encodes a ligand binding domain from an EcR or RXR polypeptide. Preferably, the polynucleotide encoding the ligand binding domain from an EcR or RXR polypeptide, is a polynucleotide encoding an EcR or RXR polypeptide comprising a truncation mutation. These gene expression cassettes and polynucleotides and the polypeptides they encode are useful as components of a nuclear receptor-based gene expression system to modulate the expression of a gene within a host cell. Thus, the present invention also provides an isolated polypeptide comprising a nuclear receptor ligand binding domain according to the invention.

Thus, the present invention also relates to an isolated truncated Group H nuclear receptor, truncated EcR, truncated Group B nuclear receptor, or truncated RXR polypeptide encoded by a polynucleotide or a gene expression cassette according to the invention. Specifically, the present invention relates to an isolated truncated EcR or RXR polypeptide comprising a truncation mutation that affects ligand binding activity or ligand sensitivity encoded by a polynucleotide according to the invention.

The present invention also relates to an isolated truncated Group H nuclear receptor, truncated EcR, truncated Group B nuclear receptor, or truncated RXR polypeptide comprising a truncation mutation. Specifically, the present invention relates to an isolated EcR or RXR polypeptide comprising a truncation mutation that affects ligand binding activity or ligand sensitivity.

Preferably, the truncation mutation results in a truncated EcR polypeptide or a truncated RXR polypeptide comprising a deletion of at least 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, or 265 amino acids. More preferably, the EcR or RXR polypeptide truncation comprises a deletion of at least a partial polypeptide domain. Even more preferably, the EcR or RXR polypeptide truncation comprises a deletion of at least an entire polypeptide domain. In a specific embodiment, the EcR or RXR polypeptide truncation comprises a deletion of at least an A/B-domain deletion, a C-domain deletion, a D-domain deletion, an E-domain deletion, an F-domain deletion, an A/B/C-domains deletion, an A/B/½-C-domains deletion, an A/B/C/D-domains deletion, an A/B/C/D/F-domains deletion, an A/B/F-domains, and an A/B/C/F-domains deletion. A combination of several complete and/or partial domain deletions may also be performed.

In a preferred embodiment, the isolated truncated ecdysone receptor polypeptide is encoded by a polynucleotide comprising a polynucleotide sequence selected from the group consisting of SEQ ID NO: 1 (CfEcR-CDEF), SEQ ID NO: 2 (CfEcR-½CDEF), SEQ ID NO: 3 (CfEcR-DEF), SEQ ID NO: 4 (CfEcR-EF), SEQ ID NO: 5 (CfEcR-DE), SEQ ID NO: 6 (DmEcR-CDEF), SEQ ID NO: 7 (DmEcR-½CDEF), SEQ ID NO: 8 (DmEcR-DEF), SEQ ID NO: 9 (DmEcR-EF), and SEQ ID NO: 10 (DmEcR-DE). In another preferred embodiment, the isolated truncated ecdysone receptor polypeptide comprises an amino acid sequence selected from the group consisting of SEQ ID NO: 11 (CfEcR-CDEF), SEQ ID NO: 12 (CfEcR-½CDEF), SEQ ID NO: 13 (CfEcR-DEF), SEQ ID NO: 14 (CfEcR-EF), SEQ ID NO: 15 (CfEcR-DE), SEQ ID NO: 16 (DmEcR-CDEF), SEQ ID NO: 17 (DmEcR-½CDEF), SEQ ID NO: 18 (DmEcR-DEF), SEQ ID NO: 19 (DmEcR-EF), and SEQ ID NO: 20 (DmEcR-DE).

In a preferred embodiment, the isolated truncated RXR polypeptide is encoded by a polynucleotide comprising a polynucleotide sequence selected from the group consisting of SEQ ID NO: 21 (MmRXR-CDEF), SEQ ID NO: 22 (MmRXR-DEF), SEQ ID NO: 23 (MmRXR-EF), SEQ ID NO: 24 (MmRXR-truncatedEF), SEQ ID NO: 25 (MmRXR-E), SEQ ID NO: 26 (HsRXR-CDEF), SEQ ID NO: 27 (HsRXR-DEF), SEQ ID NO: 28 (HsRXR-EF), SEQ ID NO: 29 (HsRXR-truncatedEF) and SEQ ID NO: 30 (HsRXR-E). In another preferred embodiment, the isolated truncated RXR polypeptide comprises an amino acid sequence selected from the group consisting of SEQ ID NO: 31 (MmRXR-CDEF), SEQ ID NO: 32 (MmRXR-DEF), SEQ ID NO: 33 (MmRXR-EF), SEQ ID NO: 34 (MmRXR-truncatedEF), SEQ ID NO: 35 (MmRXR-E), SEQ ID NO: 36 (HsRXR-CDEF), SEQ ID NO: 37 (HsRXR-DEF), SEQ ID NO: 38 (HsRXR-EF), SEQ ID NO: 39 (HsRXR-truncatedEF), and SEQ ID NO: 40 (HsRXR-E).

The present invention relates to an isolated EcR or RXR polypeptide comprising a truncation mutation that reduces ligand binding activity or ligand sensitivity of the EcR or RXR polypeptide, wherein the polypeptide is encoded by a polynucleotide comprising a polynucleotide sequence selected from the group consisting of SEQ ID NO: 1 (CfEcR-CDEF), SEQ ID NO: 2 (CfEcR-½CDEF), SEQ ID NO: 3 (CfEcRDE), SEQ ID NO: 4 (CfEcR-EF), SEQ ID NO: 5 (CfEcR-DE), SEQ ID NO: 6 (DmEcR-CDEF), SEQ ID NO: 7 (DmEcR-½CDEF), SEQ ID NO: 8 (DmEcR-DEF), SEQ ID NO: 9 (DmEcR-EF), SEQ ID NO: 10 (DmEcR-DE), SEQ ID NO: 21 (MmRXR-CDEF), SEQ ID NO: 22 (MmRXR-DEF), SEQ ID NO: 23 (MmRXR-EF), SEQ ID NO: 24 (MmRXR-truncatedEF), SEQ ID NO: 25 (MmRXR-E), SEQ ID NO: 26 (HsRXR-CDEF), SEQ ID NO: 27 (HsRXR-DEF), SEQ ID NO: 28 (HsRXR-EF), SEQ ID NO: 29 (HsRXR-truncatedEF), and SEQ ID NO: 30 (HsRXR-E).

Thus, the present invention relates to an isolated truncated EcR or RXR polypeptide comprising a truncation mutation that reduces ligand binding activity or ligand sensitivity of the EcR or RXR polypeptide, wherein the polypeptide comprises an amino acid sequence selected from the group consisting of SEQ ID NO: 1 (CfEcR-CDEF), SEQ ID NO: 12 (CfEcR-½CDEF), SEQ ID NO: 13 (CfEcR-DEF), SEQ ID NO: 14 (CfEcR-EF), SEQ ID NO: 15 (CfEcR-DE), SEQ ID NO: 16 (DmEcR-CDEF), SEQ ID NO: 17 (DmEcR-½CDEF), SEQ ID NO: 18 (DmEcR-DEF), SEQ ID NO: 19 (DmEcR-EF), SEQ ID NO: 20 (DmEcR-DE), SEQ ID NO: 31 (MmRXR-CDEF), SEQ ID NO: 32 (MmRXR-DEF), SEQ ID NO: 33 (MmRXR-EF), SEQ ID NO: 34 (MmRXR-truncatedEF), SEQ ID NO: 35 (MmRXR-E), SEQ ID NO: 36 (HsRXR-CDEF), SEQ ID NO: 37 (HsRXR-DEF), SEQ ID NO: 38 (HsRXR-EF), SEQ ID NO: 39 (HsRXR-truncatedEF), and SEQ ID NO: 40 (HsRXR-E).

In a specific embodiment, the present invention relates to an isolated EcR or RXR polypeptide comprising a truncation mutation that reduces steroid binding activity or steroid sensitivity of the EcR or RXR polypeptide. In a preferred embodiment, the present invention relates to an isolated EcR polypeptide comprising a truncation mutation that reduces steroid binding activity or steroid sensitivity of the EcR polypeptide, wherein the EcR polypeptide is encoded by a polynucleotide comprising a nucleic acid sequence of SEQ ID NO: 3 (CfEcR-DEF), SEQ ID NO: 4 (CfEcR-EF), SEQ ID NO: 8 (DmEcR-DEF), or SEQ ID NO: 9 (DmEcR-EF). Accordingly, the present invention also relates to an isolated truncated EcR or RXR polypeptide comprising a truncation mutation that reduces steroid binding activity or steroid sensitivity of the EcR or RXR polypeptide. In a preferred embodiment, the present invention relates to an isolated EcR polypeptide comprising a truncation mutation that reduces steroid binding activity or steroid sensitivity of the EcR polypeptide, wherein the EcR polypeptide comprises an amino acid sequence of SEQ ID NO: 13 (CfEcR-DEF), SEQ ID NO: 14 (CfEcR-EF), SEQ ID NO: 18 (DmEcR-DEF), or SEQ ID NO: 19 (DmEcR-EF).

In another specific embodiment, the present invention relates to an isolated EcR or RXR polypeptide comprising a truncation mutation that reduces non-steroid binding activity or non-steroid sensitivity of the EcR or RXR polypeptide. In a preferred embodiment, the present invention relates to an isolated EcR polypeptide comprising a truncation mutation that reduces non-steroid binding activity or non-steroid sensitivity of the EcR polypeptide, wherein the EcR polypeptide is encoded by a polynucleotide comprising a nucleic acid sequence of SEQ ID NO: 4 (CfEcR-EF) or SEQ ID NO: 9 (DmEcR-EF). Accordingly, the present invention also relates to an isolated truncated EcR or RXR polypeptide comprising a truncation mutation that reduces non-steroid binding activity or steroid sensitivity of the EcR or RXR polypeptide. In a preferred embodiment, the present invention relates to an isolated EcR polypeptide comprising a truncation mutation that reduces non-steroid binding activity or non-steroid sensitivity of the EcR polypeptide, wherein the EcR polypeptide comprises an amino acid sequence of SEQ ID NO: 14 (CfEcR-EF) or SEQ ID NO: 19 (DmEcR-EF).

In particular, the present invention relates to an isolated EcR or RXR polypeptide comprising a truncation mutation that enhances ligand binding activity or ligand sensitivity of the EcR or RXR polypeptide, wherein the polypeptide is encoded by a polynucleotide comprising a polynucleotide sequence selected from the group consisting of SEQ ID NO: 1 (CfEcR-CDEF), SEQ ID NO: 2 (CfEcR-½CDEF), SEQ ID NO: 3 (CfEcR-DEF), SEQ ID NO: 4 (CfEcR-EF), SEQ ID NO: 5 (CfEcR-DE), SEQ ID NO: 6 (DmEcR-CDEF), SEQ ID NO: 7 (DmEcR-½CDEF), SEQ ID NO: 8 (DmEcR-DEF), SEQ ID NO: 9 (DmEcR-EF), SEQ ID NO: 10 (DmEcR-DE), SEQ ID NO: 21 (MmRXR-CDEF), SEQ ID NO: 22 (MmRXR-DEF), SEQ ID NO: 23 (MmRXR-EF), SEQ ID NO: 24 (MmRXR-truncatedEF), SEQ ID NO: 25 (MmRXR-E), SEQ ID NO: 26 (HsRXR-CDEF), SEQ ID NO: 27 (HsRXR-DEF), SEQ ID NO: 28 (HsRXR-EF), SEQ ID NO: 29 (HsRXR-truncated EF), and SEQ ID NO: 30 (HsRXR-E).

The present invention relates to an isolated EcR or RXR polypeptide comprising a truncation mutation that enhances ligand binding activity or ligand sensitivity of the EcR or RXR polypeptide, wherein the polypeptide comprises an amino acid sequence selected from the group consisting of SEQ ID NO: 11 (CfEcR-CDEF), SEQ ID NO: 12 (CfEcR-½CDEF), SEQ ID NO: 13 (CfEcR-DEF), SEQ ID NO: 14 (CfEcR-EF), SEQ ID NO: 15 (CfEcR-DE), SEQ ID NO: 16 (DmEcR-CDEF), SEQ ID NO: 17 (DmEcR-½CDEF), SEQ ID NO: 18 (DmEcR-DEF), SEQ ID NO: 19 (DmEcR-EF), SEQ ID NO: 20 (DmEcR-DE), SEQ ID NO: 31 (MmRXR-CDEF), SEQ ID NO: 32 (MmRXR-DEF), SEQ ID NO: 33 (MmRXR-EF), SEQ ID NO: 34 (MmRXR-truncatedEF), SEQ ID NO: 35 (MmRXR-E), SEQ ID NO: 36 (HsRXR-CDEF), SEQ ID NO: 37 (HsRXR-DEF), SEQ ID NO: 39 (HsRXR-EF), SEQ ID NO: 39 (HsRXR-truncatedEF), and SEQ ID NO: 40 (HsRXR-E).

The present invention relates to an isolated EcR or RXR polypeptide comprising a truncation mutation that enhances ligand binding activity or ligand sensitivity of the EcR or RXR polypeptide. In a specific embodiment, the present invention relates to an isolated EcR or RXR polypeptide comprising a truncation mutation that enhances steroid binding activity or steroid sensitivity of the EcR or RXR polypeptide. Accordingly, the present invention also relates to an isolated EcR or RXR polypeptide comprising a truncation mutation that enhances steroid binding activity or steroid sensitivity of the EcR or RXR polypeptide.

In another specific embodiment, the present invention relates to an isolated EcR or RXR polypeptide comprising a truncation mutation that enhances non-steroid binding activity or non-steroid sensitivity of the EcR or RXR polypeptide. In a preferred embodiment, the present invention relates to an isolated EcR polypeptide comprising a truncation mutation that enhances non-steroid binding activity or non-steroid sensitivity of the EcR polypeptide, wherein the EcR polypeptide is encoded by a polynucleotide comprising a nucleic acid sequence of SEQ ID NO: 3 (CfEcR-DEF) or SEQ ID NO: 8 (DmEcR-DEF). Accordingly, the present invention also relates to an isolated EcR or RXR polypeptide comprising a truncation mutation that enhances steroid binding activity or steroid sensitivity of the EcR or RXR polypeptide. In a preferred embodiment, the present invention relates to an isolated EcR polypeptide comprising a truncation mutation that enhances non-steroid binding activity or non-steroid sensitivity of the EcR polypeptide, wherein the EcR polynucleotide comprises an amino acid sequence of SEQ ID NO: 13 (CfEcR-DEF) or SEQ ID NO: 18 (DmEcR-DEF).

The present invention also relates to an isolated retinoid X receptor polypeptide comprising a truncation mutation that increases ligand sensitivity of a heterodimer comprising the mutated retinoid X receptor polypeptide and a dimerization partner. Preferably, the isolated retinoid X receptor polypeptide comprising a truncation mutation that increases ligand sensitivity of a heterodimer is encoded by a polynucleotide comprising a nucleic acid sequence selected from the group consisting of SEQ ID NO: 23 (MmRXR-EF), SEQ ID NO: 24 (MmRXR-truncatedEF), SEQ ID NO: 28 (HsRXR-EF), or SEQ ID NO: 29 (HsRXR-truncatedEF). More preferably, the isolated polynucleotide encoding a retinoid X receptor polypeptide comprising a truncation mutation that increases ligand sensitivity of a heterodimer comprises an amino acid sequence selected from the group consisting of SEQ ID NO: 33 (MmRXR-EF), SEQ ID NO: 34 (MmRXR-truncatedEF), SEQ ID NO: 38 (HsRXR-EF), or SEQ ID NO: 39 (HsRXR-truncatedEF).

In a specific embodiment, the dimerization partner is an ecdysone receptor polypeptide. Preferably, the dimerization partner is a truncated EcR polypeptide. More preferably, the dimerization partner is an EcR polypeptide in which domains A/B/C have been deleted. Even more preferably, the dimerization partner is an EcR polypeptide comprising an amino acid sequence of SEQ ID NO: 13 (CfEcR-DEF) or SEQ ID NO: 18 (DmEcR-DEF).

The present invention also relates to compositions comprising an isolated polypeptide according to the invention.

Compositions

The present invention also relates to compositions comprising the isolated polynucleotides or polypeptides according to the invention. Such compositions may comprise a polypeptide or a polynucleotide encoding a polypeptide, as defined above, and an acceptable carrier or vehicle. The compositions of the invention are particularly suitable for formulation of biological material for use in a gene expression modulation system according to the invention. Thus, in a preferred embodiment, the composition comprises a polynucleotide encoding a polypeptide according to the invention. In another preferred embodiment, the composition comprises a polypeptide according to the invention.

The phrase "acceptable" refers to molecular entities and compositions that are physiologically tolerable to the cell or organism when administered. The term "carrier" refers to a diluent, adjuvant, excipient, or vehicle with which the composition is administered. Such carriers can be sterile liquids, such as water and oils, including those of petroleum, animal, vegetable or synthetic origin, such as peanut oil, soybean oil, mineral oil, sesame oil and the like. Examples of acceptable carriers are saline, buffered saline, isotonic saline (e.g., monosodium or disodium phosphate, sodium, potassium, calcium or magnesium chloride, or mixtures of such salts), Ringer's solution, dextrose, water, sterile water, glycerol, ethanol, and combinations thereof. 1,3-butanediol and sterile fixed oils are conveniently employed as solvents or suspending media. Any bland fixed oil can be employed including synthetic mono- or di-glycerides. Fatty acids such as oleic acid also find use in the preparation of injectables. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin. Pharmaceutical compositions of the invention may be formulated for the purpose of topical, oral, parenteral, intranasal, intravenous, intramuscular, subcutaneous, intraocular, and the like, administration.

Preferably, the compositions comprise an acceptable vehicle for an injectable formulation. This vehicle can be, in particular, a sterile, isotonic saline solution (monosodium or disodium phosphate, sodium, potassium, calcium or magnesium chloride, and the like, or mixtures of such salts), or dry, in particular lyophilized, compositions which, on addition, as appropriate, of sterilized water or of physiological saline, enable injectable solutions to be formed. The preferred sterile injectable preparations can be a solution or suspension in a nontoxic parenterally acceptable solvent or diluent.

In yet another embodiment, a composition comprising a polypeptide according to the invention, or polynucleotide encoding the polypeptide, can be delivered in a controlled release system. For example, the polynucleotide or polypeptide may be administered using intravenous infusion, an implantable osmotic pump, a transdermal patch, liposomes, or other modes of administration. Other controlled release systems are discussed in the review by Langer [*Science* 249:1527–1533 (1990)].

Method of Modulating Gene Expression of the Invention

Applicants' invention also relates to methods of modulating gene expression in a host cell using a gene expression modulation system according to the invention. Specifically, Applicants' invention provides a method of modulating the expression of a gene in a host cell comprising the steps of: a) introducing into the host cell a gene expression modulation system according to the invention; and b) introducing into the host cell a ligand; wherein the gene to be modulated is a component of a gene expression cassette comprising: i) a response element comprising a domain recognized by the DNA binding domain of the gene expression system; ii) a promoter that is activated by the transactivation domain of the gene expression system; and iii) a gene whose expression is to be modulated, whereby upon introduction of the ligand into the host cell, expression of the gene is modulated.

The invention also provides a method of modulating the expression of a gene in a host cell comprising the steps of: a) introducing into the host cell a gene expression modulation system according to the invention; b) introducing into the host cell a gene expression cassette according to the invention, wherein the gene expression cassette comprises i) a response element comprising a domain recognized by the DNA binding domain from the gene expression system; ii) a promoter that is activated by the transactivation domain of the gene expression system; and iii) a gene whose expression is to be modulated; and c) introducing into the host cell a ligand; whereby upon introduction of the ligand into the host cell, expression of the gene is modulated.

Applicants' invention also provides a method of modulating the expression of a gene in a host cell comprising a gene expression cassette comprising a response element comprising a domain to which the DNA binding domain from the first hybrid polypeptide of the gene expression modulation system binds; a promoter that is activated by the transactivation domain of the second hybrid polypeptide of the gene expression modulation system; and a gene whose expression is to be modulated; wherein the method comprises the steps of: a) introducing into the host cell a gene expression modulation system according to the invention; and b) introducing into the host cell a ligand; whereby upon introduction of the ligand into the host, expression of the gene is modulated.

Genes of interest for expression in a host cell using Applicants' methods may be endogenous genes or heterologous genes. Nucleic acid or amino acid sequence information for a desired gene or protein can be located in one of many public access databases, for example, GENBANK, EMBL, Swiss-Prot, and PIR, or in many biology related journal publications. Thus, those skilled in the art have access to nucleic acid sequence information for virtually all known genes. Such information can then be used to construct the desired constructs for the insertion of the gene of interest within the gene expression cassettes used in Applicants' methods described herein.

Examples of genes of interest for expression in a host cell using Applicants' methods include, but are not limited to: antigens produced in plants as vaccines, enzymes like alpha-amylase, phytase, glucanes, and xylanse, genes for resistance against insects, nematodes, fungi, bacteria, viruses, and abiotic stresses, nutraceuticals, pharmaceuticals, vitamins, genes for modifying amino acid content, herbicide resistance, cold, drought, and heat tolerance, industrial products, oils, protein, carbohydrates, antioxidants, male sterile plants, flowers, fuels, other output traits, genes encoding therapeutically desirable polypeptides or products that may be used to treat a condition, a disease, a disorder, a dysfunction, a genetic defect, such as monoclonal antibodies, enzymes, proteases, cytokines, interferons, insulin, erthropoietin, clotting factors, other blood factors or components, viral vectors for gene therapy, virus for vaccines, targets for drug discovery, functional genomics, and proteomics analyses and applications, and the like.

Acceptable ligands are any that modulate expression of the gene when binding of the DNA binding domain of the gene expression system according to the invention to the response element in the presence of the ligand results in activation or suppression of expression of the genes. Preferred ligands include an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726; dibenzoylalkyl cyanohydrazines such as those disclosed in European Application No. 461,809; N-alkyl-N,N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; each of which is incorporated herein by reference and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, farnesol, bile acids, 1,1-biphosphonate esters, Juvenile hormone III, and the like.

In a preferred embodiment, the ligand for use in Applicants' method of modulating expression of gene is a compound of the formula:

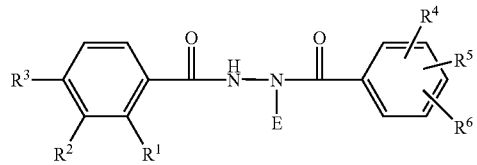

wherein:
E is a $(C_4-C_6)$alkyl containing a tertiary carbon or a cyano$(C_3-C_5)$alkyl containing a tertiary carbon;

$R^1$ is H, Me, Et, i-Pr, F, formyl, $CF_3$, $CHF_2$, $CHCl_2$, $CH_2F$, $CH_2Cl$, $CH_2OH$, $CH_2OMe$, $CH_2CN$, CN, C°CH, 1-propynyl, 2-propynyl, vinyl, OH, OMe, OEt, cyclopropyl, $CF_2CF_3$, CH=CHCN, allyl, azido, SCN, or $SCHF_2$;

$R^2$ is H, Me, Et, n-Pr, i-Pr, formyl, $CF_3$, $CHF_2$, $CHCl_2$, $CH_2F$, $CH_2Cl$, $CH_2OH$, $CH_2OMe$, $CH_2CN$, CN, C°CH, 1-propynyl, 2-propynyl, vinyl, Ac, F, Cl, OH, OMe, OEt, O-n-Pr, OAc, $NMe_2$, $NEt_2$, SMe, SEt, $SOCF_3$, $OCF_2CF_2H$, COEt, cyclopropyl, $CF_2CF_3$, CH=CHCN, allyl, azido, $OCF_3$, $OCHF_2$, O-i-Pr, SCN, $SCHF_2$, SOMe, NH—CN, or joined with $R^3$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon;

$R^3$ is H, Et, or joined with $R^2$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon;

$R^4$, $R^5$, and $R^6$ are independently H, Me, Et, F, Cl, Br, formyl, $CF_3$, $CHF_2$, $CHCl_2$, $CH_2F$, $CH_2Cl$, $CH_2OH$, CN, C°CH, 1-propynyl, 2-propynyl, vinyl, OMe, OEt, SMe, or SEt.

In another preferred embodiment, the ligand for use in Applicants' method of modulating expression of gene is an ecdysone, 20-hydroxyecdysone, ponasterone A, muristerone A, an oxysterol, a 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, farnesol, bile acids, 1,1-biphosphonate esters, or Juvenile hormone III.

In another preferred embodiment, a second ligand may be used in addition to the first ligand discussed above in Applicants' method of modulating expression of a gene. Preferably, this second ligand is 9-cis-retinoic acid or a synthetic analog of retinoic acid.

Host Cells and Non-Human Organisms of the Invention

As described above, the gene expression modulation system of the present invention may be used to modulate gene expression in a host cell. Expression in transgenic host cells may be useful for the expression of various genes of interest. Applicants' invention provides for modulation of gene expression in prokaryotic and eukaryotic host cells. Expression in transgenic host cells is useful for the expression of various polypeptides of interest including but not limited to antigens produced in plants as vaccines, enzymes like alpha-amylase, phytase, glucanes, and xylanse, genes for resistance against insects, nematodes, fungi, bacteria, viruses, and abiotic stresses, antigens, nutraceuticals, pharmaceuticals, vitamins, genes for modifying amino acid content, herbicide resistance, cold, drought, and heat tolerance, industrial products, oils, protein, carbohydrates, antioxidants, male sterile plants, flowers, fuels, other output traits, therapeutic polypeptides, pathway intermediates; for the modulation of pathways already existing in the host for the synthesis of new products heretofore not possible using the host; cell based assays; functional genomics assays, biotherapeutic protein production, proteomics assays, and the like. Additionally the gene products may be useful for conferring higher growth yields of the host or for enabling an alternative growth mode to be utilized.

Thus, Applicants' invention provides an isolated host cell comprising a gene expression system according to the invention. The present invention also provides an isolated host cell comprising a gene expression cassette according to the invention. Applicants' invention also provides an isolated host cell comprising a polynucleotide or a polypeptide according to the invention. The present invention also relates to a host cell transfected with an expression vector according to the invention. The host cell may be a bacterial cell, a fungal cell, a nematode cell, an insect cell, a fish cell, a plant cell, an avian cell, an animal cell, or a mammalian cell. In still another embodiment, the invention relates to a method for producing a nuclear receptor ligand binding domain comprising a substitution mutation, wherein the method comprises culturing the host cell as described above in culture medium under conditions permitting expression of a polynucleotide encoding the nuclear receptor ligand binding domain comprising a substitution mutation, and isolating the nuclear receptor ligand binding domain comprising a substitution mutation from the culture.

In a specific embodiment, the isolated host cell is a prokaryotic host cell or a eukaryotic host cell. In another specific embodiment, the isolated host cell is an invertebrate host cell or a vertebrate host cell. Preferably, the host cell is selected from the group consisting of a bacterial cell, a fungal cell, a yeast cell, a nematode cell, an insect cell, a fish cell, a plant cell, an avian cell, an animal cell, and a mammalian cell. More preferably, the host cell is a yeast cell, a nematode cell, an insect cell, a plant cell, a zebrafish cell, a chicken cell, a hamster cell, a mouse cell, a rat cell, a rabbit cell, a cat cell, a dog cell, a bovine cell, a goat cell, a cow cell, a pig cell, a horse cell, a sheep cell, a simian cell, a monkey cell, a chimpanzee cell, or a human cell. Examples of preferred host cells include, but are not limited to, fungal or yeast species such as *Aspergillus, Trichoderma, Saccharomyces, Pichia, Candida, Hansenula*, or bacterial species such as those in the genera *Synechocystis, Synechococcus, Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium* and *Klebsiella*; plant species selected from the group consisting of an apple, *Arabidopsis*, bajra, banana, barley, beans, beet, blackgram, chickpea, chili, cucumber, eggplant, favabean, maize, melon, millet, mungbean, oat, okra, Panicum, papaya, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat; animal; and mammalian host cells.

In a specific embodiment, the host cell is a yeast cell selected from the group consisting of a Saccharomyces, a Pichia, and a Candida host cell.

In another specific embodiment, the host cell is a *Caenorhabdus elegans* nematode cell.

In another specific embodiment, the host cell is an insect cell.

In another specific embodiment, the host cell is a plant cell selected from the group consisting of an apple, *Arabidopsis*, bajra, banana, barley, beans, beet, blackgram, chickpea, chili, cucumber, eggplant, favabean, maize, melon, millet, mungbean, oat, okra, Panicum, papaya, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat cell.

In another specific embodiment, the host cell is a zebrafish cell.

In another specific embodiment, the host cell is a chicken cell.

In another specific embodiment, the host cell is a mammalian cell selected from the group consisting of a hamster cell, a mouse cell, a rat cell, a rabbit cell, a cat cell, a dog cell, a bovine cell, a goat cell, a cow cell, a pig cell, a horse cell, a sheep cell, a monkey cell, a chimpanzee cell, and a human cell.

Host cell transformation is well known in the art and may be achieved by a variety of methods including but not limited to electroporation, viral infection, plasmid/vector transfection, non-viral vector mediated transfection, *Agrobacterium*-mediated transformation, particle bombardment, and the like. Expression of desired gene products involves culturing the transformed host cells under suitable conditions and inducing expression of the transformed gene. Culture conditions and gene expression protocols in prokaryotic and eukaryotic cells are well known in the art (see General Methods section of Examples). Cells may be harvested and the gene products isolated according to protocols specific for the gene product.

In addition, a host cell may be chosen which modulates the expression of the inserted polynucleotide, or modifies and processes the polypeptide product in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce a non-glycosylated core protein product. However, a polypeptide expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, the polypeptide's activity. Furthermore, different vector/host expression systems may affect processing reactions, such as proteolytic cleavages, to a different extent.

Applicants' invention also relates to a non-human organism comprising an isolated host cell according to the invention. In a specific embodiment, the non-human organism is a prokaryotic organism or a eukaryotic organism. In another specific embodiment, the non-human organism is an invertebrate organism or a vertebrate organism.

Preferably, the non-human organism is selected from the group consisting of a bacterium, a fungus, a yeast, a nematode, an insect, a fish, a plant, a bird, an animal, and a mammal. More preferably, the non-human organism is a yeast, a nematode, an insect, a plant, a zebrafish, a chicken, a hamster, a mouse, a rat, a rabbit, a cat, a dog, a bovine, a goat, a cow, a pig, a horse, a sheep, a simian, a monkey, or a chimpanzee.

In a specific embodiment, the non-human organism is a yeast selected from the group consisting of *Saccharomyces, Pichia*, and *Candida*.

In another specific embodiment, the non-human organism is a *Caenorhabdus elegans* nematode.

In another specific embodiment, the non-human organism is a plant selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum*, papaya, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat.

In another specific embodiment, the non-human organism is a *Mus musculus* mouse.

Measuring Gene Expression/Transcription

One useful measurement of Applicants' methods of the invention is that of the transcriptional state of the cell including the identities and abundances of RNA, preferably mRNA species. Such measurements are conveniently conducted by measuring cDNA abundances by any of several existing gene expression technologies.

Nucleic acid array technology is a useful technique for determining differential mRNA expression. Such technology includes, for example, oligonucleotide chips and DNA microarrays. These techniques rely on DNA fragments or oligonucleotides which correspond to different genes or cDNAs which are immobilized on a solid support and hybridized to probes prepared from total mRNA pools extracted from cells, tissues, or whole organisms and converted to cDNA. Oligonucleotide chips are arrays of oligonucleotides synthesized on a substrate using photolithographic techniques. Chips have been produced which can analyze for up to 1700 genes. DNA microarrays are arrays of DNA samples, typically PCR products, that are robotically printed onto a microscope slide. Each gene is analyzed by a full or partial-length target DNA sequence. Microarrays with up to 10,000 genes are now routinely prepared commercially. The primary difference between these two techniques is that oligonucleotide chips typically utilize 25-mer oligonucleotides which allow fractionation of short DNA molecules whereas the larger DNA targets of microarrays, approximately 1000 base pairs, may provide more sensitivity in fractionating complex DNA mixtures.

Another useful measurement of Applicants' methods of the invention is that of determining the translation state of the cell by measuring the abundances of the constituent protein species present in the cell using processes well known in the art.

Where identification of genes associated with various physiological functions is desired, an assay may be employed in which changes in such functions as cell growth, apoptosis, senescence, differentiation, adhesion, binding to a specific molecules, binding to another cell, cellular organization, organogenesis, intracellular transport, transport facilitation, energy conversion, metabolism, myogenesis, neurogenesis, and/or hematopoiesis is measured.

In addition, selectable marker or reporter gene expression may be used to measure gene expression modulation using Applicants' invention.

Other methods to detect the products of gene expression are well known in the art and include Southern blots (DNA detection), dot or slot blots (DNA, RNA), northern blots (RNA), RT-PCR (RNA), western blots (polypeptide detection), and ELISA (polypeptide) analyses. Although less preferred, labeled proteins can be used to detect a particular nucleic acid sequence to which it hybridizes.

In some cases it is necessary to amplify the amount of a nucleic acid sequence. This may be carried out using one or more of a number of suitable methods including, for example, polymerase chain reaction ("PCR"), ligase chain reaction ("LCR"), strand displacement amplification ("SDA"), transcription-based amplification, and the like. PCR is carried out in accordance with known techniques in which, for example, a nucleic acid sample is treated in the presence of a heat stable DNA polymerase, under hybridizing conditions, with one pair of oligonucleotide primers, with one primer hybridizing to one strand (template) of the specific sequence to be detected. The primers are sufficiently complementary to each template strand of the specific sequence to hybridize therewith. An extension product of each primer is synthesized and is complementary to the nucleic acid template strand to which it hybridized. The extension product synthesized from each primer can also serve as a template for further synthesis of extension products using the same primers. Following a sufficient number of rounds of synthesis of extension products, the sample may be analyzed as described above to assess whether the sequence or sequences to be detected are present.

The present invention may be better understood by reference to the following non-limiting Examples, which are provided as exemplary of the invention.

EXAMPLES

General Methods

Standard recombinant DNA and molecular cloning techniques used herein are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, Greene Publishing Assoc. and Wiley-Interscience (1987).

Methods for plant tissue culture, transformation, plant molecular biology, and plant, general molecular biology may be found in *Plant Tissue Culture Concepts and Laboratory Exercises* edited by RN Trigiano and DJ Gray, $2^{nd}$ edition, 2000, CRC press, New York; *Agrobacterium Protocols* edited by KMA Gartland and MR Davey, 1995, Humana Press, Totowa, N.J.; *Methods in Plant Molecular Biology*, P. Maliga et al., 1995, Cold Spring Harbor Lab Press, New York; and *Molecular Cloning*, J. Sambrook et al., 1989, Cold Spring Harbor Lab Press, New York.

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of host cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences may be accomplished using the suite of programs available from the Genetics Computer Group Inc. (Wisconsin Package Version 9.0, Genetics Computer Group (GCG), Madison, Wis.). Where the GCG program "Pileup" is used the gap creation default value of 12, and the gap extension default value of 4 may be used. Where the CGC "Gap" or "Bestfit" programs is used the default gap creation penalty of 50 and the default gap extension penalty of 3 may be used. In any case where GCG program parameters are not prompted for, in these or any other GCG program, default values may be used.

The meaning of abbreviations is as follows: "h" means hour(s), "min" means minute(s), "sec" means second(s), "d" means day(s), "µl" means microliter(s), "ml" means milliliter(s), "L" means liter(s), "µM" means micromolar, "mM" means millimolar, "µg" means microgram(s), "mg" means milligram(s), "A" means adenine or adenosine, "T" means thymine or thymidine, "G" means guanine or guanosine, "C" means cytidine or cytosine, "x g" means times gravity, "nt" means nucleotide(s), "aa" means amino acid(s), "bp" means base pair(s), "kb" means kilobase(s), "k" means kilo, "µ" means micro, and "° C" means degrees Celsius.

Example 1

Applicants' improved EcR-based inducible gene modulation system was developed for use in various applications including gene therapy, expression of proteins of interest in host cells, production of transgenic organisms, and cell-based assays. This Example describes the construction and evaluation of several gene expression cassettes for use in the EcR-based inducible gene expression system of the invention.

In various cellular backgrounds, including mammalian cells, insect ecdysone receptor (EcR) heterodimerizes with retinoid X receptor (RXR) and, upon binding of ligand, transactivates genes under the control of ecdysone response elements. Applicants constructed several EcR-based gene expression cassettes based on the spruce budworm *Choristoneura fumiferana* EcR ("CfEcR"; full length polynucleotide and amino acid sequences are set forth in SEQ ID NO: 58 and SEQ ID NO: 59, respectively), *C. fumiferana* ultraspiracle ("CfUSP"; full length polynucleotide and amino acid sequences are set forth in SEQ ID NO: 60 and SEQ ID NO: 61, respectively), and mouse *Mus musculus* RXRα (MmRXRα; full length polynucleotide and amino acid sequences are set forth in SEQ ID NO: 62 and SEQ ID NO: 63, respectively). The prepared receptor constructs comprise a ligand binding domain of EcR and of RXR or of USP; a DNA binding domain of GAL4 or of EcR; and an activation domain of VP16. The reporter constructs include a reporter gene, luciferase or LacZ, operably linked to a synthetic promoter construct that comprises either GAL4 or EcR/USP binding sites (response elements). Various combinations of these receptor and reporter constructs were cotransfected into CHO, NIH3T3, CV1 and 293 cells. Gene induction potential (magnitude of induction) and ligand specificity and sensitivity were examined using four different ligands: two steroidal ligands (ponasterone A and muristerone A) and two non-steroidal ligands (N-(2-ethyl-3-methoxybenzoyl)-N'-(3,5-dimethylbenzoyl)-N'-tert-butylhydrazine and N-(3,4-(1,2-ethylenedioxy)-2-methylbenzoyl)-N'-(3,5-dimethylbenzoyl)-N'-tert-butylhydrazine) in a dose-dependent induction of reporter gene expression in the transfected cells. Reporter gene expression activities were assayed at 24 hours or 48 hours after ligand addition.

Gene Expression Cassettes:

Ecdysone receptor-based, chemically inducible gene expression cassettes (switches) were constructed as followed, using standard cloning methods available in the art. The following is brief description of preparation and composition of each switch.

1.1—GAL4EcR/VP16RXR:

The D, E, and F domains from spruce budworm *Choristoneura fumiferana* EcR ("CfEcRDEF"; SEQ ID NO: 3) were fused to GAL4 DNA binding domain ("DNABD"; SEQ ID NO: 43) and placed under the control of an SV40e promoter (SEQ ID NO: 64). The DEF domains from mouse (*Mus musculus*) RXR ("MmRXRDEF"; SEQ ID NO: 22) were fused to the activation domain from VP16 ("VP16AD"; SEQ ID NO: 49) and placed under the control of an SV40e promoter (SEQ ID NO: 64). Five consensus GAL4 binding sites ("5× GAL4RE"; comprising 5, GAL4RE comprising SEQ ID NO: 56) were fused to a synthetic E1b minimal promoter (SEQ ID NO: 65) and placed upstream of the luciferase gene (SEQ ID NO: 66).

1.2—GAL4EcR/VP16USP:

This construct was prepared in the same way as in switch 1.1 above except MmRXRDEF was replaced with the D, E and F domains from spruce budworm USP ("CfUSPDEF"; SEQ ID NO: 67). The constructs used in this example are similar to those disclosed in U.S. Pat. No. 5,880,333 except that *Choristoneura fumiferana* USP rather than *Drosophila melanogaster* USP was utilized.

1.3—GAL4RXR/VP16CfEcR:

MmRXRDEF (SEQ ID NO: 22) was fused to a GAL4DNABD (SEQ ID NO: 43) and CfEcRCDEF (SEQ ID NO: 1) was fused to a VP16AD (SEQ ID NO: 49).

1.4—GAL4RXR/VP16DmEcR:

This construct was prepared in the same way as switch 1.3 except CfEcRCDEF was replaced with DmEcRCDEF (SEQ ID NO: 6).

1.5—GAL4USP/VP16CfEcR:

This construct was prepared in the same way as switch 1.3 except MmRXRDEF was replaced with CfUSPDEF (SEQ ID NO: 67).

1.6—GAL4RXRCfEcRVP16:

This construct was prepared so that both the GAL4 DNABD and the VP16AD were placed on the same molecule. GAL4DNABD (SEQ ID NO: 43) and VP16AD (SEQ ID NO: 49) were fused to CfEcRDEF (SEQ ID NO: 3) at N-and C-termini respectively. The fusion was placed under the control of an SV40e promoter (SEQ ID NO: 64).

1.7—VP16CfEcR:

This construct was prepared such that CfEcRCDEF (SEQ ID NO: 1) was fused to VP16AD (SEQ ID NO: 49) and placed under the control of an SV40e promoter (SEQ ID NO: 64). Six ecdysone response elements ("EcRE"; SEQ ID NO: 55) from the hsp27 gene were placed upstream of the promoter and a luciferase gene (SEQ ID NO: 66). This switch most probably uses endogenous RXR.

1.8—DmVgRXR:

This system was purchased from Invitrogen Corp., Carlsbad, California. It comprises a *Drosophila melanogaster* EcR ("DmEcR") with a modified DNABD fused to VP16AD and placed under the control of a CMV promoter (SEQ ID NO: 68). Full length MmRXR (SEQ ID NO: 62) was placed under the control of the RSV promoter (SEQ ID NO: 69). The reporter, pIND(SP1)LacZ, contains five copies of a modified ecdysone response element ("EcRE", E/GRE), three copies of an SPI enhancer, and a minimal heat shock promoter, all of which were placed upstream to the LacZ reporter gene.

1.9—CfVgRXR:

This example was prepared in the same way as switch 1.8 except DmEcR was replaced with a truncated CfEcR comprising a partial A/B domain and the complete CDEF domains [SEQ ID NO: 70 (polynucleotide) and SEQ ID NO: 71 (polypeptide)].

1.10—CfVgRXRdel:

This example was prepared in the same way as switch 1.9 except MmRXR (SEQ ID NO: 62) was deleted.

Cell Lines:

Four cell lines: CHO, Chinese hamster Cricetulus griseus ovarian cell line; NIH3T3 (3T3) mouse *Mus musculus* cell line; 293 human Homo sapiens kidney cell line, and CV1 African green monkey kidney cell line were used in these experiments. Cells were maintained in their respective media and were subcultured when they reached 60% confluency. Standard methods for culture and maintenance of the cells were followed.

Transfections:

Several commercially available lipofactors as well as electroporation methods were evaluated and the best conditions for transfection of each cell line were developed. CHO, NIH3T3, 293 and CV1 cells were grown to 60% confluency. DNAs corresponding to the various switch constructs outlined in Examples 1.1 through 1.10 were transfected into CHO cells, NIH3T3 cells, 293 cells, or CV1 cells as follows.

CHO Cells:

Cells were harvested when they reach 60–80% confluency and plated in 6- or 12-or 24- well plates at 250,000, 100,000, or 50,000 cells in 2.5, 1.0, or 0.5 ml of growth medium containing 10% Fetal bovine serum respectively. The next day, the cells were rinsed with growth medium and transfected for four hours. LipofectAMINE™ 2000 (Life Technologies Inc,) was found to be the best transfection reagent for these cells. For 12- well plates, 4 µl of LipofectAMINE™ 2000 was mixed with 100 µl of growth medium. 1.0 µg of reporter construct and 0.25 µg of receptor construct(s) were added to the transfection mix. A second reporter construct was added [pTKRL (Promega), 0.1 µg/transfection mix] and comprised a Renilla luciferase gene (SEQ ID NO: 72) operably linked and placed under the control of a thymidine kinase (TK) constitutive promoter and was used for normalization. The contents of the transfection mix were mixed in a vortex mixer and let stand at room temperature for 30 min. At the end of incubation, the transfection mix was added to the cells maintained in 400 µl growth medium. The cells were maintained at 37° C. and 5% $CO_2$ for four hours. At the end of incubation, 500 µl of growth medium containing 20% FBS and either DMSO (control) or a DMSO solution of appropriate ligands were added and the cells were maintained at 37° C. and 5% $CO_2$ for 24–48 hr. The cells were harvested and reporter activity was assayed. The same procedure was followed for 6 and 24 well plates as well except all the reagents were doubled for 6 well plates and reduced to half for 24-well plates.

NIH3T3 Cells:

Superfect™ (Qiagen Inc.) was found to be the best transfection reagent for 3T3 cells. The same procedures described for CHO cells were followed for 3T3 cells as well with two modifications. The cells were plated when they reached 50% confluency. 125,000 or 50,000 or 25,000 cells were plated per well of 6- or 12- or 24-well plates respectively. The GA14EcR/VP16RXR and reporter vector DNAs were transfected into NIH3T3 cells, the transfected cells were grown in medium containing PonA, MurA, N-(2-ethyl-3-methoxybenzoyl)-N'-(3,5-dimethylbenzoyl)-N'-t-butylhydrazine, or N-(3,4-(1,2-ethylenedioxy)-2-methylbenzoyl)-N'-(3,5-dimethylbenzoyl)-N'-tert-butylhydrazine for 48 hr. The ligand treatments were performed as described in the CHO cell section above.

293 Cells:

LipofectAMINE™ 2000 (Life Technologies) was found to be the best lipofactor for 293 cells. The same procedures described for CHO were followed for 293 cells except that the cells were plated in biocoated plates to avoid clumping. The ligand treatments were performed as described in the CHO cell section above.

CV1 Cells:

LipofectAMINE™ plus (Life Technologies) was found to be the best lipofactor for CV1 cells. The same procedures described for NIH3T3 cells were followed for CV1 cells Ligands:

Ponasterone A and Muristerone A were purchased from Invitrogen and Sigma Chemical Company. The two non-steroids N-(2-ethyl-3-methoxybenzoyl)-N'-(3,5-dimethylbenzoyl)-N'-t-butylhydrazine, or N-(3,4-(,12-ethylenedioxy)-2-methylbenzoyl)-N'-(3,5-dimethylbenzoyl)-N'-tert-butylhydrazine are synthetic stable ecdysteroids synthesized at Rohm and Haas Company. All ligands were dissolved in DMSO and the final concentration of DMSO was maintained at 0.1% in both controls and treatments.

Reporter Assays:

Cells were harvested 24–48 hr after adding ligands. 125, 250, or 500 µl of passive lysis buffer (part of Dual-luciferase reporter assay system from Promega Corporation) were added to each well of 24- or 12- or 24-well plates respectively. The plates were placed on a rotary shaker for 15 min. Twenty µl of lysate was assayed. Luciferase activity was measured using Dual-luciferase reporter assay system from Promega Corporation following the manufacturer's instructions. β-Galactosidase was measured using Galacto-Star™ assay kit from TROPIX following the manufacturer's instructions. All luciferase and β-galactosidase activities were normalized using Renilla luciferase as a standard. Fold activities were calculated by dividing normalized relative light units ("RLU") in ligand treated cells with normalized RLU in DMSO treated cells (untreated control).

The results of these experiments are provided in the following tables.

TABLE 1

Transactivation of reporter genes through various switches in CHO cells

| | Composition of Switch | Mean Fold Activation with 50 µM N-(2-ethyl-3-methoxybenzoyl)-N'-(3,5-dimethylbenzoyl)-N'-t-butylhydrazine |
|---|---|---|
| 1.1 | GAL4EcR + VP16RXR pGAL4RELuc | 267 |
| 1.2 | GAL4EcR + VP16USP pGAL4RELuc | 2 |
| 1.3 | GAL4RXR + VP16CfEcR pGAL4RELuc | 85 |
| 1.4 | GAL4RXR + VP16DmEcR pGAL4RELuc | 312 |
| 1.5 | GAL4USP + VP16CfEcR pGAL4RELuc | 2 |
| 1.6 | GAL4CfEcRVP16 pGAL4RELuc | 9 |
| 1.7 | VP16CfEcR pEcRELuc | 36 |
| 1.8 | DmVgRXR + MmRXR pIND(SP1)LacZ | 14 |
| 1.9 | CfVgRXR + MmRXR pIND(SP1)LacZ | 27 |
| 1.10 | CfVgRXR pIND(SP1)LacZ | 29 |

TABLE 2

Transactivation of reporter genes through various switches in 3T3 cells

| | Composition of Switch | Mean Fold Activation Through N-(2-ethyl-3-methoxybenzoyl)-N'-(3,5-dimethylbenzoyl)-N'-t-butylhydrazine |
|---|---|---|
| 1.1 | GAL4EcR + VP16RXR pGAL4RELuc | 1118 |
| 1.2 | GAL4EcR + VP16USP pGAL4RELuc | 2 |
| 1.3 | GAL4RXR + VP16CfEcR pGAL4RELuc | 47 |
| 1.4 | GAL4RXR + VP16DmEcR pGAL4RELuc | 269 |
| 1.5 | GAL4USP + VP16CfEcR pGAL4RELuc | 3 |
| 1.6 | GAL4CfEcRVP16 pGAL4RELuc | 7 |
| 1.7 | VP16CfEcR pEcRELuc | 1 |
| 1.8 | DmVgRXR + MmRXR pIND(SP1)LacZ | 21 |
| 1.9 | CfVgRXR + MmRXR pIND(SP1)LacZ | 19 |
| 1.10 | CfVgRXR pIND(SP1)LacZ | 2 |

TABLE 3

Transactivation of reporter genes through various switches in 293 cells

| | Composition of Switch | Mean Fold Activation Through N-(2-ethyl-3-methoxybenzoyl)-N'-(3,5-dimethylbenzoyl)-N'-t-butylhydrazine |
|---|---|---|
| 1.1 | GAL4EcR + VP16RXR pGAL4RELuc | 125 |
| 1.2 | GAL4EcR + VP16USP pGAL4RELuc | 2 |
| 1.3 | GAL4RXR + VP16CfEcR pGAL4RELuc | 17 |
| 1.4 | GAL4RXR + VP16DmEcR pGAL4RELuc | 3 |
| 1.5 | GAL4USP + VP16CfEcR pGAL4RELuc | 2 |
| 1.6 | GAL4CfEcRVP16 pGAL4RELuc | 3 |
| 1.7 | VP16CfEcR pEcRELuc | 2 |
| 1.8 | DmVgRXR + MmRXR pIND(SP1)LacZ | 21 |
| 1.9 | CfVgRXR + MmRXR pIND(SP1)LacZ | 12 |
| 1.10 | CfVgRXR pIND(SP1)LacZ | 3 |

TABLE 4

Transactivation of reporter genes through various switches in CV1 cells

| | Composition of Switch | Mean Fold Activation Through N-(2-ethyl-3-methoxybenzoyl)-N'-(3,5-dimethylbenzoyl)-N'-t-butylhydrazine |
|---|---|---|
| 1.1 | GAL4EcR + VP16RXR pGAL4RELuc | 279 |
| 1.2 | GAL4EcR + VP16USP pGAL4RELuc | 2 |
| 1.3 | GAL4RXR + VP16CfEcR pGAL4RELuc | 25 |
| 1.4 | GAL4RXR + VP16DmEcR pGAL4RELuc | 80 |
| 1.5 | GAL4USP + VP16CfEcR pGAL4RELuc | 3 |
| 1.6 | GAL4CfEcRVP16 pGAL4RELuc | 6 |
| 1.7 | VP16CfEcR pEcRELuc | 1 |
| 1.8 | DmVgRXR + MmRXR pIND(SP1)LacZ | 12 |
| 1.9 | CfVgRXR + MmRXR pIND(SP1)LacZ | 7 |
| 1.10 | CfVgRXR IND(SP1)LacZ | 1 |

TABLE 5

Transactivation of reporter gene GAL4CfEcRDEF/VP16MmRXRDEF (switch 1.1) through steroids and non-steroids in 3T3 cells.

| Ligand | Mean Fold Induction at 1.0 μM Concentration |
|---|---|
| 1. Ponasterone A | 1.0 |
| 2. Muristerone A | 1.0 |
| 3. N-(2-ethyl-3-methoxybenzoyl)-N'-(3,5-dimethylbenzoyl)-N'-tert-butylhydrazine | 116 |
| 4. N'-(3,4-(1,2-ethylenedioxy-2-methylbenzoyl)-N'-(3,5-dimethylbenzoyl)-N'-tert-butylhydrazine | 601 |

TABLE 6

Transactivation of reporter gene GAL4MmRXRDEF/VP16CfEcRCDEF
(switch 1.3) through steroids and non-steroids in 3T3 cells.

| Ligand | Mean Fold Induction at 1.0 µM Concentration |
|---|---|
| 1. Ponasterone A | 1.0 |
| 2. Muristerone A | 1.0 |
| 3. N-(2-ethyl-3-methoxybenzoyl)-N'-3,5-dimethylbenzoyl)-N'-tert-butylhydrazine | 71 |
| 4. N'-(3,4-(1,2-ethylenedioxy)-2-methylbenzoyl)-N'-(3,5-dimethylbenzoyl)-N'-tert-butylhydrazine | 54 |

Applicants' results demonstrate that the non-steroidal ecdysone agonists, N-(2-ethyl-3-methoxybenzoyl)-N'-(3,5-dimethylbenzoyl)-N'-tert-butylhydrazine and N'-(3,4-(1,2-ethylenedioxy)-2-methylbenzoyl)-N'-(3,5-dimethylbenzoyl)-N'-tert-butylhydrazine, were more potent activators of CfEcR as compared to *Drosophila melanogaster* EcR (DmEcR). (see Tables 1–4). Also, in the mammalian cell lines tested, MmRXR performed better than CfUSP as a heterodimeric partner for CfEcR. (see Tables 1–4). Additionally, Applicants' inducible gene expression modulation system performed better when exogenous MmRXR was used than when the system relied only on endogenous RXR levels (see Tables 1–4).

Applicants' results also show that in a CfEcR-based inducible gene expression system, the non-steroidal ecdysone agonists induced reporter gene expression at a lower concentration (i.e., increased ligand sensitivity) as compared to the steroid ligands, ponasterone A and muristerone A (see Tables 5 and 6).

Out of 10 EcR based gene switches tested, the GAL4EcR/VP16RXR switch (Switch 1.1) performed better than any other switch in all four cell lines examined and was more sensitive to non-steroids than steroids. The results also demonstrate that placing the activation domain (AD) and DNA binding domain (DNABD) on each of the two partners reduced background when compared to placing both AD and DNABD together on one of the two partners. Therefore, a switch format where the AD and DNABD are separated between two partners, works well for EcR-based gene switch applications.

In addition, the MmRXR/EcR-based switches performed better than CfUSP/EcR-based switches, which have a higher background activity than the MmRXR/EcR switches in the absence of ligand.

Finally, the GAL4EcRNP 16RXR switch (Switch 1.1) was more sensitive to non-steroid ligands than to the steroid ligands (see Tables 5 and 6). In particular, steroid ligands initiated transactivation at concentrations of 50 µM, whereas the non-steroid ligands initiated transactivation at less than 1 µM (submicromolar) concentration.

Example 2

This Example describes Applicants' further analysis of truncated EcR and RXR polypeptides in the improved EcR-based inducible gene expression system of the invention. To identify the best combination and length of two receptors that give a switch with a) maximum induction in the presence of ligand; b) minimum background in the absence of ligand; c) highly sensitive to ligand concentration; and d) minimum cross-talk among ligands and receptors, Applicants made and analyzed several truncation mutations of the CfEcR and MmRXR receptor polypeptides in NIH3T3 cells.

Briefly, polynucleotides encoding EcR or RXR receptors were truncated at the junctions of A/B, C, D, E and F domains and fused to either a GAL4 DNA binding domain encoding polynucleotide (SEQ ID NO: 43) for CfEcR, or a VP16 activation domain encoding polynucleotide (SEQ ID NO: 49) for MmRXR as described in Example 1. The resulting receptor truncation/fusion polypeptides were assayed in NIH3T3 cells. Plasmid pFRLUC (Stratagene) encoding a luciferase polypeptide was used as a reporter gene construct and pTKRL (Promega) encoding a Renilla luciferase polypeptide under the control of the constitutive TK promoter was used to normalize the transfections as described above. The analysis was performed in triplicates and mean luciferase counts were determined as described above.

Gene Expression Cassettes Encoding Truncated Ecdysone Receptor Polypeptides

Figure 11:
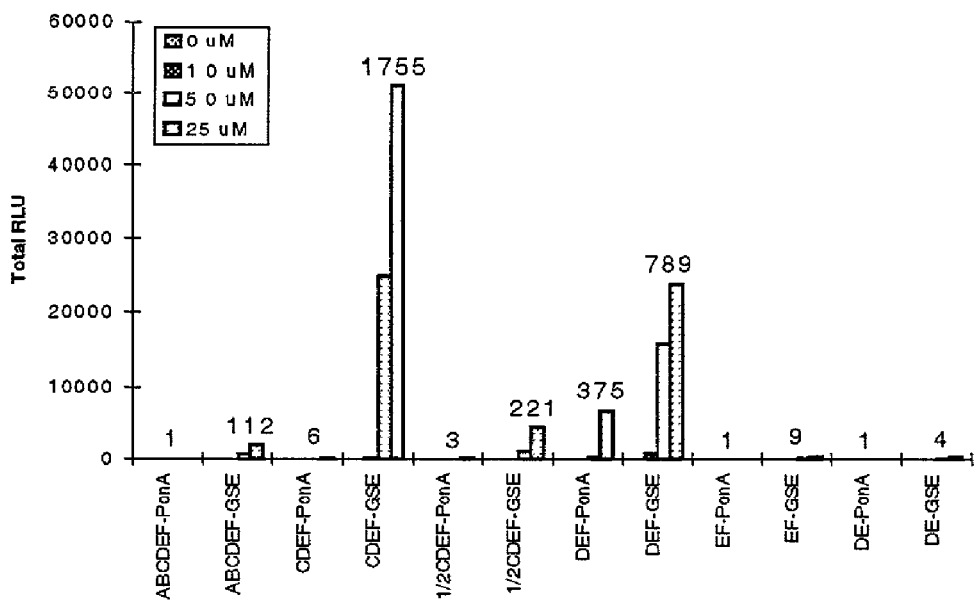
FIG. 11: Expression data of GAL4CfEcRA/BCDEF, GAL4CfEcRCDEF, GAL4CfEcR½CDEF, GAL4CfEcRDEF, GAL4CfEcREF, GAL4CfEcRDE truncation mutants transfected into NIH3T3 cells along with VP16MmRXRDE, pFRLUc and pTKRL plasmid DNAs.
Figure 12:
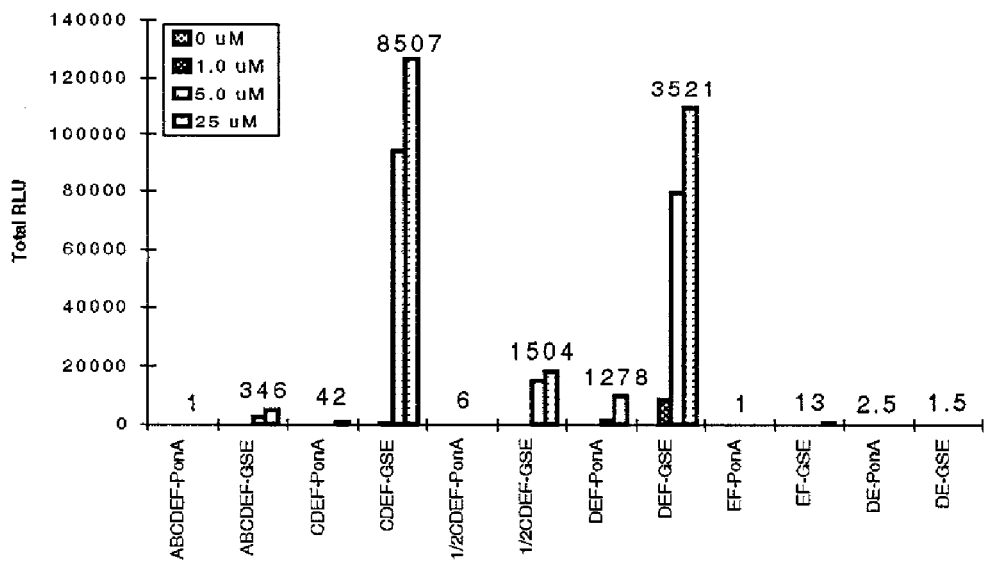
FIG. 12: Expression data of GAL4CfEcRA/BCDEF, GAL4CfEcRCDEF, GAL4CfEcR½CDEF, GAL4CfEcRDEF, GAL4CfEcREF, GAL4CfEcRDE truncation mutants transfected into 3T3 cells along with VP16MmRXRE, pFRLUc and pTKRL plasmid DNAs.

Gene expression cassettes comprising polynucleotides encoding either full length or truncated CfEcR polypeptides fused to a GAL4 DNA binding domain (SEQ ID NO: 43): GAL4CfEcRA/BCDEF (full length CfEcRA/BCDEF; SEQ ID NO: 58), GAL4CfEcRCDEF (CfEcRCDEF; SEQ ID NO: 1), GAL4CfEcR½CDEF (CfEcR½CDEF; SEQ ID NO: 2), GAL4CfEcRDEF (CfEcRDEF; SEQ ID NO: 3), GAL4CfEcREF (CfEcREF; SEQ ID NO: 4), and GAL4CfEcRDE (CfEcRDE; SEQ ID NO: 5) were transfected into NIH3T3 cells along with VP16MmRXRDEF (constructed as in Example 1.1; FIG. 11) or VP16MmRXREF [constructed as in Example 1.1 except that MmRXRDEF was replaced with MmRXREF (SEQ ID NO: 23); FIG. 12], and pFRLUc and pTKRL plasmid DNAs. The transfected cells were grown in the presence 0, 1, 5 or 25 uM of N-(2-ethyl-3-methoxybenzoyl)-N'-(3,5-dimethylbenzoyl)-N'-tert-butylhydrazine or PonA for 48 hr. The cells were harvested, lysed and luciferase reporter activity was measured in the cell lysates. Total fly luciferase relative light units are presented. The number on the top of each bar is the maximum fold induction for that treatment.

Applicants' results show that the EF domain of MmRXR is sufficient and performs better than DEF domains of this receptor (see FIGS. 11 and 12). Applicants have also shown that, in general, EcR/RXR receptor combinations are insensitive to PonA (see FIGS. 11 and 12). As shown in the FIGS. 11 and 12, the GAL4CfEcRCDEF hybrid polypeptide (SEQ ID NO: 7) performed better than any other CfEcR hybrid polypeptide.

Gene Expression Cassettes Encoding Truncated Retinoid X Receptor Polypeptides

Figure 13:
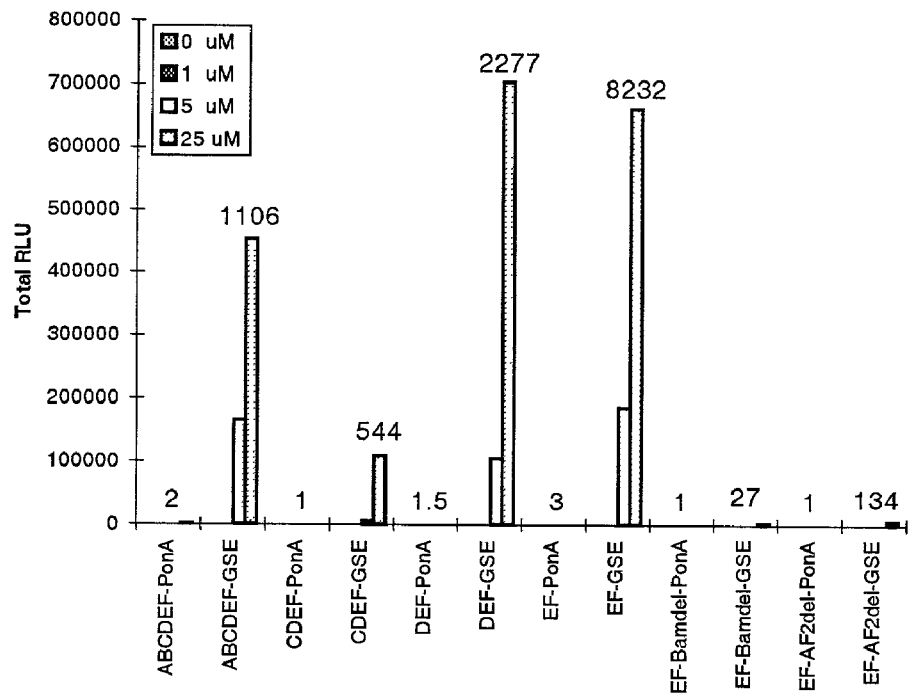
FIG. 13: Expression data of VP16MmRXRA/BCDEF, VP16MmRXRCDEF, VP16MmRXRDEF, VP16MmRXREF, VP16MmRXRBam-EF, VP16MmRXRAF2del constructs transfected into NIH3T3 cells along with GAL4CfEcRCDEF, pFRLUc and pTKRL plasmid DNAs.
Figure 14:
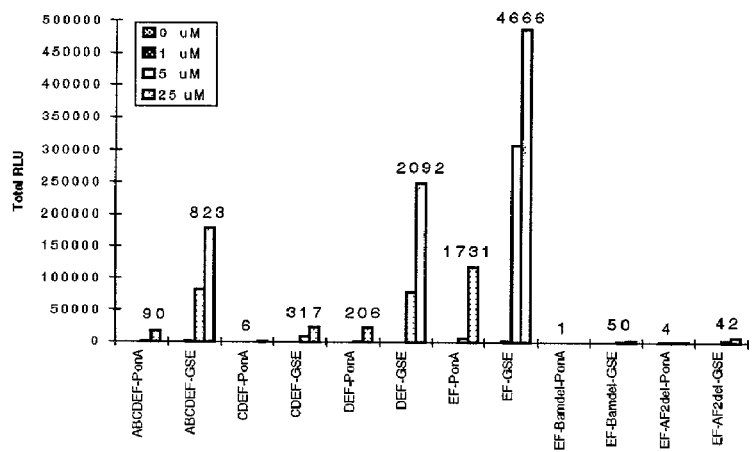
FIG. 14: Expression data of VP16MmRXRA/BCDEF, VP16MmRXRCDEF, VP16MmRXRDEF, VP16MmRXREF, VP16MmRXRBam-EF, VP16MmRXRAF2del constructs transfected into NIH3T3 cells along with GAL4CfEcRDEF, pFRLUc and pTKRL plasmid DNAs.

Gene expression cassettes comprising polynucleotides encoding either full length or truncated MmRXR polypeptides fused to a VP16 transactivation domain (SEQ ID NO: 49): VP16MmRXRA/BCDEF (full length MmRXRA/BCDEF; SEQ ID NO: 62), VP16MmRXRCDEF (MmRXRCDEF; SEQ ID NO: 21), VP16MmRXRDEF (MmRXRDEF; SEQ ID NO: 22), VP16MmRXREF (MmRXREF; SEQ ID NO: 23), VP16MmRXRBam-EF ("MmRXRBam-EF" or "MmRXR-truncatedEF"; SEQ ID NO: 24), and VP16MmRXRAF2del ("MmRXRAF2del" or "MmRXR-E"; SEQ ID NO: 25) constructs were transfected into NIH3T3 cells along with GAL4CfEcRCDEF (constructed as in Example 1.1; FIG. 13) or GAL4CfEcRDEF [constructed as in Example 1.1 except CfEcRCDEF was replaced with CfEcRDEF (SEQ ID NO: 3); FIG. 14], pFRLUc and pTKRL plasmid DNAs as described above. The transfected cells were grown in the presence 0, 1, 5 and 25 uM of N-(2-ethyl-3-methoxybenzoyl)-N'-(3,5-dimethylbenzoyl)-N'-tert-butylhydrazine or PonA for 48 hr. The cells were harvested and lysed and reporter activity was measured in the cell lysate. Total fly luciferase relative light units are presented. The number on top of each bar is the maximum fold induction in that treatment.

Of all the truncations of MmRXR tested, Applicants' results show that the MmRXREF receptor was the best partner for CfEcR (FIGS. 13 and 14). CfEcRCDEF showed better induction than CfEcRDEF using MmRXREF. Deleting AF2 (abbreviated "EF-AF2del") or helices 1–3 of the E domain (abbreviated "EF-Bamdel") resulted in an RXR receptor that reduced gene induction and ligand sensitivity when partnered with either CfEcRCDEF (FIG. 13) or CfEcRDEF (FIG. 14) in NIH3T3 cells. In general, the CfEcR/RXR-based switch was much more sensitive to the nonsteroid N-(2-ethyl-3-methoxybenzoyl)-N'-(3,5-dimethylbenzoyl)-N'-tert-butylhydrazine than to the steroid PonA.

Example 3

This Example describes Applicants' further analysis of gene expression cassettes encoding truncated EcR or RXR receptor polypeptides that affect either ligand binding activity or ligand sensitivity, or both. Briefly, six different combinations of chimeric receptor pairs, constructed as described in Examples 1 and 2, were further analyzed in a single experiment in NIH3T3 cells. These six receptor pair combinations and their corresponding sample numbers are depicted in Table 7.

TABLE 7

CfEcR + MmRXR Truncation Receptor Combinations in NIH3T3 Cells

Figure 15:
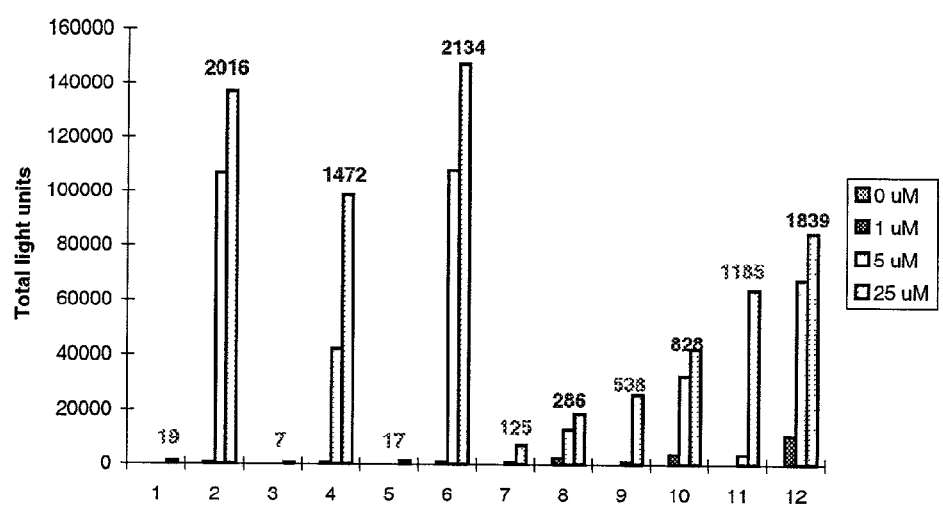
FIG. 15: Expression data of various truncated CfEcR and MmRXR receptor pairs transfected into NIH3T3 cells along with GAL4CfEcRDEF, pFRLUc and pTKRL plasmid DNAs.

| FIG. 15 X-Axis Sample No. | EcR Polypeptide Construct | RXR Polypeptide Construct |
|---|---|---|
| Samples 1 and 2 | GAL4CfEcRCDEF | VP16RXRA/BCDEF (Full length) |
| Samples 3 and 4 | GAL4CfEcRCDEF | VP16RXRDEF |
| Samples 5 and 6 | GAL4CfEcRCDEF | VP16RXREF |
| Samples 7 and 8 | GAL4CfEcRDEF | VP16RXRA/BCDEF (Full length) |
| Samples 9 and 10 | GAL4CfEcRDEF | VP16RXRDEF |
| Samples 11 and 12 | GAL4CfEcRDEF | VP16RXREF |

The above receptor construct pairs, along with the reporter plasmid pFRLuc were transfected into NIH3T3 cells as described above. The six CfEcR truncation receptor combinations were duplicated into two groups and treated with either steroid (odd numbers on x-axis of FIG. 15) or non-steroid (even numbers on x-axis of FIG. 15). In particular, the cells were grown in media containing 0, 1, 5 or 25 uM PonA (steroid) or N-(2-ethyl-3-methoxybenzoyl)-N'-(3,5-dimethylbenzoyl)-N'-tert-butylhydrazine (non-steroid) ligand. The reporter gene activity was measured and total RLU are shown. The number on top of each bar is the maximum fold induction for that treatment and is the mean of three replicates.

As shown in FIG. 15, the CfEcRCDEF/MmRXREF receptor combinations were the best switch pairs both in terms of total RLU and fold induction (compare columns 1–6 to columns 7–12). This confirms Applicants' earlier findings as described in Example 2 (FIGS. 11-14). The same gene expression cassettes encoding the truncated EcR and RXR polypeptides were also assayed in a human lung carcinoma cell line A549 (ATCC) and similar results were observed (data not shown).

Example 4

This Example describes a CfEcR-based yeast two-hybrid assay prepared according to the invention. Briefly, gene expression constructs were prepared as follows:

4.1—CfEcR-DEF in pGLIDA:

The D, E, and F domains from spruce budworm *Choristoneura fumiferana* EcR ("CfEcRDEF"; SEQ ID NO: 3) were fused to a LexA DNA binding domain ("LexA-DNABD"; SEQ ID NO: 45) and placed under the control of a GAL1 promoter (SEQ ID NO: 73) in pGLIDA (CLONTECH). This construct results in a LexA:CfEcRDEF fusion that is expressed under the GAL1 promoter.

4.2—CfEcR-CDEF in pGLIDA:

The C, D, E, and F domains from spruce budworm *Choristoneura fumiferana* EcR ("CfEcRCDEF"; SEQ ID NO: 1) were fused to a LexA DNA binding domain ("LexA-DNABD"; SEQ ID NO: 45) and placed under the control of a GAL1 promoter (SEQ ID NO: 73) in pGLIDA (CLONTECH). This construct results in a LexA:CfEcRCDEF fusion that is expressed under the GAL1 promoter.

4.3—MmRXR-A/BCDEF in pB42AD: The A/B, C, D, E, and F domains from mouse (*Mus musculus*) RXR a ("MmRXRA/BCDEF"; SEQ ID NO: 62) were fused to a B42 transactivation domain ("B42AD"; SEQ ID NO: 53) and placed under the control of a GAL1 promoter (SEQ ID NO: 73) in pB42AD (CLONTECH). This construct results in a B42AD:MmRXR-A/BCDEF fusion that is expressed under the GAL1 promoter.

4.4—MmRXR-DEF in pB42AD:

The D, E, and F domains from mouse (*Mus musculus*) RXR α ("MmRXRDEF"; SEQ ID NO: 22) were fused to a B42 transactivation domain ("B42AD"; SEQ ID NO: 53) and placed under the control of a GAL1 promoter (SEQ ID NO: 73) in pB42AD (CLONTECH). This construct results in a B42AD:MmRXR-DEF fusion that is expressed under the GAL 1 promoter.

4.5—CfuSP-DEF in pB42AD: The D, E, and F domains from spruce budworm *Choristoneura fumiferana* EcR ("CfEcRDEF"; SEQ ID NO: 3) were fused to a B42 transactivation domain ("B42AD"; SEQ ID NO: 53) and placed under the control of a GAL1 promoter (SEQ ID NO: 73) in pB42AD (CLONTECH). This construct results in a B42AD:CfUSP-DEF fusion that is expressed under the GAL1 promoter.

4.6—CfEcR-CDEFV in pGLIDA: The C, D, E, and F domains from spruce budworm *Choristoneura fumiferana*

EcR ("CfEcRCDEF"; SEQ ID NO: 1) were fused to a LexA DNA binding domain ("LexADNABD"; SEQ ID NO: 45) and to a VP16 transactivation domain ("VP16AD"; SEQ ID NO: 49) at N-and C-termini respectively, and placed under the control of a GAL1 promoter (SEQ ID NO: 73) in pGLIDA (CLONTECH). This construct results in a LexA: CfEcR-CDEF/VP16 fusion that is expressed under the GAL1 promoter.

4.7—pSH118:

A reporter plasmid comprising a β-galactosidase gene (LacZ; SEQ ID NO: 74) under the control of an 8XLexA operon response element ("8XlexAop"; SEQ ID NO: 75) operably linked to a minimal TATAA region from the GAL1 promoter (p8op-lacZ from CLONTECH) was used to monitor inducible gene expression.

Yeast Cells:

*Saccharomyces cerevisiae* yeast cells (EGY48; CLONTECH) were used in these experiments. Cells were maintained in liquid culture media with the appropriate drop out amino acids. Standard methods for culture and maintenance of the cells were followed.

Transfections:

DNAs corresponding to the various switch constructs outlined in Examples 4.1 through 4.7 were transfected into the yeast cells following the protocol described by Ito et al., 1983 (J. Bacteriol., 153:163–168).

Ligands:

20-hydroxyecdysone (20E), Ponasterone A (PonA) and Muristerone A (MurA) were purchased from Invitrogen and Sigma Chemical Company. The four non-steroids N-(2-ethyl-3-methoxybenzoyl)-N'-(3,5-dimethylbenzoyl)-N'-t-butylhydrazine (GS™-E), N-tert-butyl-N'-(3-methoxy-2-methylbenzoyl)-N-(3,5-dimethylbenzoyl)hydrazine (RH-2485), N-tert-butyl-N'-(4-ethylbenzoyl)-N-(3,5-dimethylbenzoyl)hydrazine (RH-5992), and N-tert-butyl-N, N'-dibenzoylhydrazine (RH-5849) are synthetic stable ecdysteroids synthesized at Rohm and Haas Company. All ligands were dissolved in DMSO and the final concentration of DMSO was maintained at 0.1% in both controls and treatments.

RESULTS

DNA constructs pSH118, CfEcRDEF, and MmRXRA/BCDEF, MmRXRDEF, or CFUSPDEF were transfected into yeast cells. In addition, DNA constructs pSH118, CfEcRCDEF, and MmRXRA/BCDEF, MmRXRDEF, or CfUSPDEF were transfected into yeast cells. As a control, DNA constructs pSH118 and CfEcRCDEV were also transfected into yeast cells. A colony from each group of transformants was grown in the liquid culture in the presence of 0, 0.04, 0.2, 1, 5 and 25 μM GS™-E. The reporter activity was measured as described above 4 hours after adding ligand. Total RLUs were calculated and the numbers on the bars of FIG. 16 show maximum fold induction observed for that group (see FIGS. 16 and 17).

Figure 16:
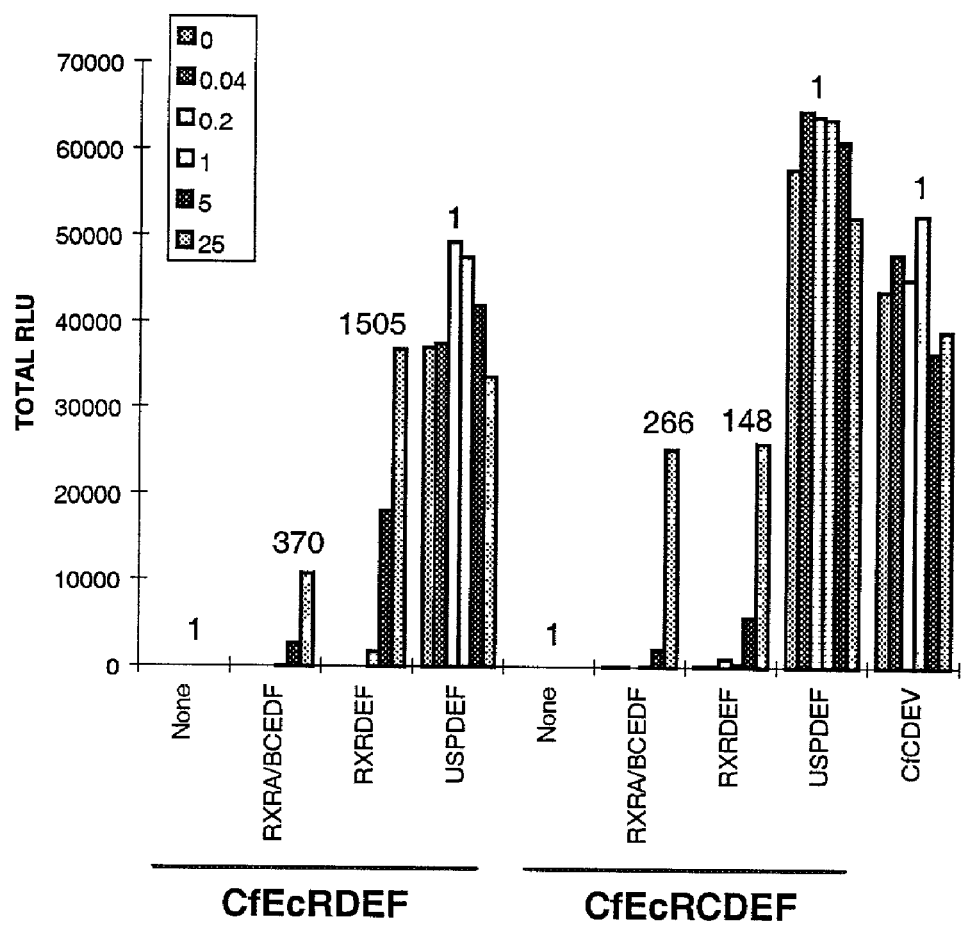
FIG. 16: Expression data of CfEcR-DEF or CfEcR-CDEF in pGLIDA in combination with full length MmRXR, MmRXR-DEF or CfUSP-DEF in pB42AD transfected into yeast cells along with pSH118 reporter plasmid.
Figure 17:
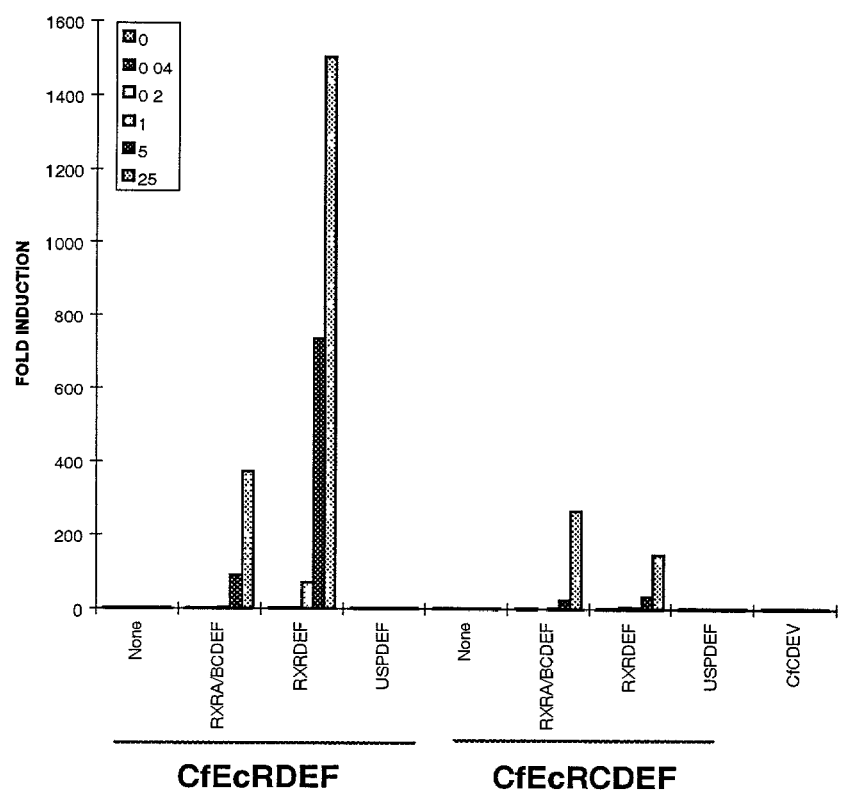
FIG. 17: Fold induction expression data of CfEcR-DEF or CfEcR-CDEF in pGLIDA in combination with full length MmRXR, MmRXR-DEF or CfUSP-DEF in pB42AD transfected into yeast cells along with pSH118 reporter plasmid.

As shown in FIGS. 16 and 17, transactivation by CfEcR: CfUSP and CfEcRCDEFV combinations are ligand independent, whereas CfEcR/MmRXR combinations are ligand dependent. CfEcRDEF/MmRXRDEF performed the best of any combination tested. This yeast assay closely reflects the performance of these switch formats in mammalian cells. The background levels are lower and induced levels are higher, and as a result, the fold induction is high, approximately 1800-fold. This number is much higher than the fold inductions observed by Tran et al., 2001 (Mol. Endo., 15:1140–1153; and International PCT patent application publication WO 01/61350A1). Thus, the dose-response of GS™-E on the gene regulation system described herein in yeast cells appears to be similar to that observed in mammalian cells.

The best performing transformed yeast strain from the analysis above comprising CfEcRDEF:MmRXRDEF was used to determine the induction activity of three steroid ligands (20E, PonA, MurA) and four non-steroid ligands (GS™-E, RH2485, RH5992, RH5849) in this yeast-based format. The yeast cells were cultured in the presence of 0, 0.1, 1, 10, 50 and 100 μM ligands for four hours and the reporter activity was measured as described above. Total RLUs were calculated and the numbers on the top of the bars of FIG. 18 show the maximum fold induction for that group (see FIGS. 18 and 19).

Figure 18:
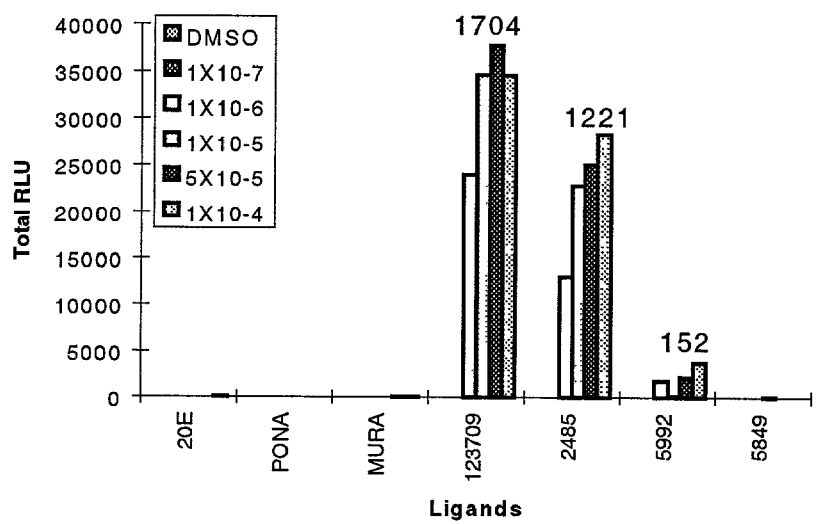
FIG. 18: Expression data of CfEcR-DEF in pGLIDA in combination with MmRXR-DEF in pB42AD transfected into yeast cells along with pSH118 reporter plasmid in the presence of three steroidal ligands and four non-steroidal ligands.
Figure 19:
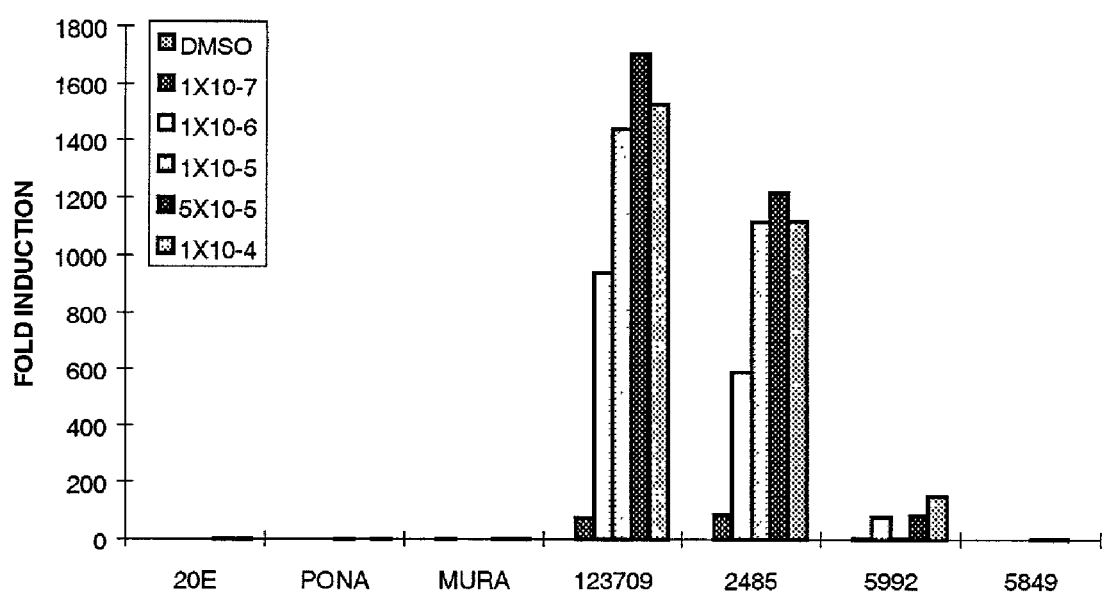
FIG. 19: Fold induction expression data of CfEcR-DEF in pGL1DA in combination with MmRXR-DEF in pB42AD transfected into yeast cells along with pSH118 reporter plasmid in the presence of three steroidal ligands and four non-steroidal ligands.

As shown in FIGS. 18 and 19, in the transformed yeast strain comprising CfEcRDEF:MmRXRDEF, GS™-E was able to induce gene expression better than any other ligand tested, and was followed in performance by RH-2485 and RH5992. The three steroid ligands and the remaining non-steroid ligand RH5849 did not show a significant response. The fold induction activity is similar to that observed by Tran et al., 2001 (Mol. Endo., 15:1140–1153; and International PCT patent application publication WO 01/61350A1) as well as in mammalian cells.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

We claim:

1. A gene expression modulation system comprising:
   a) a first gene expression cassette that is capable of being expressed in a host cell comprising a polynucleotide encoding a first polypeptide comprising:
      i) a DNA-binding domain that recognizes a response element associated with a gene whose expression is to be modulated;
      ii) a ligand binding domain comprising a ligand binding domain from a nuclear receptor,
   b) a second gene expression cassette that is capable of being expressed in the host cell comprising a polynucleotide encoding a second polypeptide comprising:
      i) a transactivation domain; and
      ii) a ligand binding domain comprising a ligand binding domain from a nuclear receptor other than ultraspiracle (USP), wherein the ligand binding domains from the first polypeptide and the second polypeptide are different.

2. The gene expression modulation system according to claim 1, further comprising a third gene expression cassette comprising:
   i) a response element to which the DNA-binding domain of the first polypeptide binds;
   ii) a promoter that is activated by the transactivation domain of the second polypeptide; and
   iii) the gene whose expression is to be modulated.

3. The gene expression modulation system according to claim 1, wherein the ligand binding domain of the first polypeptide is an ecdysone receptor polypeptide.

4. The gene expression modulation system according to claim 1, wherein the ligand binding domain of the second polypeptide is a retinoid X receptor polypeptide.

5. A gene expression modulation system comprising:
   a) a first gene expression cassette that is capable of being expressed in a host cell comprising a polynucleotide encoding a first polypeptide comprising:
      i) a DNA-binding domain that recognizes a response element associated with a gene whose expression is to be modulated; and
      ii) a ligand binding domain comprising a ligand binding domain from an ecdysone receptor; and
   b) a second gene expression cassette that is capable of being expressed in the host cell comprising a polynucleotide encoding a second polypeptide comprising:
      i) a transactivation domain; and
      ii) a ligand binding domain comprising a ligand binding domain from a retinoid X receptor.

6. The gene expression modulation system according to claim 5, further comprising a third gene expression cassette comprising:
   i) a response element to which the DNA-binding domain of the first polypeptide binds;
   ii) a promoter that is activated by the transactivation domain of the second polypeptide; and
   iii) the gene whose expression is to be modulated.

7. The gene expression modulation system according to claim 5, wherein the ligand binding domain of the first polypeoptide is encoded by a polynucleotide comprising the nucleic acid sequence of SEQ ID NO:3.

8. A gene expression modulation system comprising:
a) a first gene expression cassette that is capable of being expressed in a host cell comprising a polynucleotide encoding a first polypeptide comprising:
   i) a DNA-binding domain that recognizes a response element associated with a gene whose expression is to be modulated; and
   ii) a ligand binding domain comprising a ligand binding domain from a retinoid X receptor, and
b) a second gene expression cassette that is capable of being expressed in the host cell comprising a polynucleotide encoding a second polypeptide comprising:
   i) a transactivation domain; and
   ii) a ligand binding domain comprising a ligand binding domain from an ecdysone receptor.

9. The gene expression modulation system according to claim 8, further comprising a third gene expression cassette comprising:
   i) a response element to which the DNA-binding domain of the first polypeptide binds;
   ii) a promoter that is activated by the transactivation domain of the second polypeptide; and
   iii) the gene whose expression is to be modulated.

10. The gene expression modulation system according to claim 8, wherein the ligand binding domain of the second polypeptide is encoded by a polynucleotide comprising the nucleic acid sequence of SEQ ID NO:3.

* * * * *

SEQUENCE LISTING

```
<160> NUMBER OF SEQ ID NOS: 75

<210> SEQ ID NO 1
<211> LENGTH: 1288
<212> TYPE: DNA
<213> ORGANISM: Choristoneura fumiferana
<220> FEATURE:
<221> NAME/KEY: misc_feature
<223> OTHER INFORMATION: Novel Sequence

<400> SEQUENCE: 1
```

```
aagggccctg cgccccgtca gcaagaggaa ctgtgtctgg tatgcgggga cagagcctcc     60
ggataccact acaatgcgct cacgtgtgaa gggtgtaaag ggttcttcag acggagtgtt    120
accaaaaatg cggtttatat ttgtaaattc ggtcacgctt gcgaaatgga catgtacatg    180
cgacggaaat gccaggagtg ccgcctgaag aagtgcttag ctgtaggcat gaggcctgag    240
tgcgtagtac ccgagactca gtgcgccatg aagcggaaag agaagaaagc acagaaggag    300
aaggacaaac tgcctgtcag cacgacgacg gtggacgacc acatgccgcc cattatgcag    360
tgtgaacctc cacctcctga agcagcaagg attcacgaag tggtcccaag gtttctctcc    420
gacaagctgt tggagacaaa ccggcagaaa aacatccccc agttgacagc caaccagcag    480
ttccttatcg ccaggctcat ctggtaccag gacgggtacg agcagccttc tgatgaagat    540
ttgaagagga ttacgcagac gtggcagcaa gcggacgatg aaaacgaaga gtctgacact    600
cccttccgcc agatcacaga gatgactatc ctcacggtcc aacttatcgt ggagttcgcg    660
aagggattgc cagggttcgc caagatctcg cagcctgatc aaattacgct gcttaaggct    720
tgctcaagtg aggtaatgat gctccgagtc gcgcgacgat acgatgcggc ctcagacagt    780
gttctgttcg cgaacaacca agcgtacact cgcgacaact accgcaaggc tggcatggcc    840
tacgtcatcg aggatctact gcacttctgc cggtgcatgt actctatggc gttggacaac    900
atccattacg cgctgctcac ggctgtcgtc atcttttctg accggccagg gttggagcag    960
ccgcaactgg tggaagaaat ccagcggtac tacctgaata cgctccgcat ctatatcctg   1020
aaccagctga gcgggtcggc gcgttcgtcc gtcatatacg gcaagatcct ctcaatcctc   1080
tctgagctac gcacgctcgg catgcaaaac tccaacatgt gcatctccct caagctcaag   1140
aacagaaagc tgccgccttt cctcgaggag atctgggatg tggcggacat gtcgcacacc   1200
caaccgccgc ctatcctcga gtcccccacg aatctctagc cctgcgcgc acgcatcgcc   1260
gatgccgcgt ccggccgcgc tgctctga                                      1288
```

```

<210> SEQ ID NO 2
<211> LENGTH: 1110
<212> TYPE: DNA
<213> ORGANISM: Choristoneura fumiferana
<220> FEATURE:
<221> NAME/KEY: misc_feature
<223> OTHER INFORMATION: Novel Sequence

<400> SEQUENCE: 2

```

```
gcggtttata tttgtaaatt cggtcacgct tgcgaaatgg acatgtacat gcgacggaaa     60
tgccaggagt gccgcctgaa gaagtgctta gctgtaggca tgaggcctga gtgcgtagta    120
cccgagactc agtgcgccat gaagcggaaa gagaagaaag cacagaagga gaaggacaaa    180
ctgcctgtca gcacgacgac ggtggacgac cacatgccgc ccattatgca gtgtgaacct    240
ccacctcctg aagcagcaag gattcacgaa gtggtcccaa ggtttctctc cgacaagctg    300
ttggagacaa accggcagaa aaacatcccc cagttgacag ccaaccagca gttccttatc    360
gccaggctca tctggtacca ggacgggtac gagcagcctt ctgatgaaga tttgaagagg    420
attacgcaga cgtggcagca agcggacgat gaaaacgaag agtctgacac tcccttccgc    480
cagatcacag agatgactat cctcacggtc caacttatcg tggagttcgc gaagggattg    540
ccagggttcg ccaagatctc gcagcctgat caaattacgc tgcttaaggc ttgctcaagt    600
gaggtaatga tgctccgagt cgcgcgacga tacgatgcgg cctcagacag tgttctgttc    660
```

-continued

```
gcgaacaacc aagcgtacac tcgcgacaac taccgcaagg ctggcatggc ctacgtcatc    720
gaggatctac tgcacttctg ccggtgcatg tactctatgg cgttggacaa catccattac    780
gcgctgctca cggctgtcgt catcttttct gaccggccag ggttggagca gccgcaactg    840
gtggaagaaa tccagcggta ctacctgaat acgctccgca tctatatcct gaaccagctg    900
agcgggtcgg cgcgttcgtc cgtcatatac ggcaagatcc tctcaatcct ctctgagcta    960
cgcacgctcg gcatgcaaaa ctccaacatg tgcatctccc tcaagctcaa gaacagaaag   1020
ctgccgcctt tcctcgagga gatctgggat gtggcggaca tgtcgcacac ccaaccgccg   1080
cctatcctcg agtcccccac gaatctctag                                    1110
```

```
<210> SEQ ID NO 3
<211> LENGTH: 1054
<212> TYPE: DNA
<213> ORGANISM: Choristoneura fumiferana
<220> FEATURE:
<221> NAME/KEY: misc_feature
<223> OTHER INFORMATION: Novel Sequence

<400> SEQUENCE: 3
cctgagtgcg tagtacccga gactcagtgc gccatgaagc ggaaagagaa gaaagcacag     60
aaggagaagg acaaactgcc tgtcagcacg acgacggtgg acgaccacat gccgcccatt    120
atgcagtgtg aacctccacc tcctgaagca gcaaggattc acgaagtggt cccaaggttt    180
ctctccgaca agctgttgga gacaaaccgg cagaaaaaca tcccccagtt gacagccaac    240
cagcagttcc ttatcgccag gctcatctgg taccaggacg ggtacgagca gccttctgat    300
gaagatttga agaggattac gcagacgtgg cagcaagcgg acgatgaaaa cgaagagtct    360
gacactccct tccgccagat cacagagatg actatcctca cggtccaact tatcgtggag    420
ttcgcgaagg gattgccagg gttcgccaag atctcgcagc ctgatcaaat tacgctgctt    480
aaggcttgct caagtgaggt aatgatgctc cgagtcgcgc gacgatacga tgcggcctca    540
gacagtgttc tgttcgcgaa caaccaagcg tacactcgcg acaactaccg caaggctggc    600
atggcctacg tcatcgagga tctactgcac ttctgccggt gcatgtactc tatggcgttg    660
gacaacatcc attacgcgct gctcacggct gtcgtcatct tttctgaccg gccagggttg    720
gagcagccgc aactggtgga agaaatccag cggtactacc tgaatacgct ccgcatctat    780
atcctgaacc agctgagcgg gtcggcgcgt tcgtccgtca tatacggcaa gatcctctca    840
atcctctctg agctacgcac gctcggcatg caaaactcca acatgtgcat ctccctcaag    900
ctcaagaaca gaaagctgcc gcctttcctc gaggagatct gggatgtggc ggacatgtcg    960
cacacccaac cgccgcctat cctcgagtcc cccacgaatc tctagcccct gcgcgcacgc   1020
atcgccgatg ccgcgtccgg ccgcgctgct ctga                               1054
```

```
<210> SEQ ID NO 4
<211> LENGTH: 735
<212> TYPE: DNA
<213> ORGANISM: Choristoneura fumiferana
<220> FEATURE:
<221> NAME/KEY: misc_feature
<223> OTHER INFORMATION: Novel Sequence

<400> SEQUENCE: 4
taccaggacg ggtacgagca gccttctgat gaagatttga agaggattac gcagacgtgg     60
cagcaagcgg acgatgaaaa cgaagagtct gacactccct tccgccagat cacagagatg    120
actatcctca cggtccaact tatcgtggag ttcgcgaagg gattgccagg gttcgccaag    180
```

```
atctcgcagc ctgatcaaat tacgctgctt aaggcttgct caagtgaggt aatgatgctc      240
cgagtcgcgc gacgatacga tgcggcctca gacagtgttc tgttcgcgaa caaccaagcg      300
tacactcgcg acaactaccg caaggctggc atggcctacg tcatcgagga tctactgcac      360
ttctgccggt gcatgtactc tatggcgttg acaacatcc attacgcgct gctcacggct       420
gtcgtcatct tttctgaccg gccagggttg gagcagccgc aactggtgga agaaatccag      480
cggtactacc tgaatacgct ccgcatctat atcctgaacc agctgagcgg gtcggcgcgt      540
tcgtccgtca tacggcaa gatcctctca atcctctctg agctacgcac gctcggcatg         600
caaaactcca acatgtgcat ctccctcaag ctcaagaaca gaaagctgcc gccttcctc       660 gaggagatct gggatgtggc ggacatgtcg cacacccaac cgccgcctat cctcgagtcc      720
cccacgaatc tctag                                                       735

<210> SEQ ID NO 5
<211> LENGTH: 960
<212> TYPE: DNA
<213> ORGANISM: Choristoneura fumiferana
<220> FEATURE:
<221> NAME/KEY: misc_feature
<223> OTHER INFORMATION: Novel Sequence

<400> SEQUENCE: 5
cctgagtgcg tagtacccga gactcagtgc gccatgaagc ggaaagagaa gaaagcacag      60
aaggagaagg acaaactgcc tgtcagcacg acgacggtgg acgaccacat gccgcccatt      120
atgcagtgtg aacctccacc tcctgaagca gcaaggattc acgaagtggt cccaaggttt      180
ctctccgaca agctgttgga gacaaaccgg cagaaaaaca tccccagtt gacagccaac       240 cagcagttcc ttatcgccag gctcatctgg taccaggacg ggtacgagca gccttctgat      300
gaagatttga gaggattac gcagacgtgg cagcaagcgg acgatgaaaa cgaagagtct       360
gacactccct tccgccagat cacagagatg actatcctca cggtccaact tatcgtggag      420
ttcgcgaagg gattgccagg gttcgccaag atctcgcagc ctgatcaaat tacgctgctt      480
aaggcttgct caagtgaggt aatgatgctc cgagtcgcgc gacgatacga tgcggcctca      540
gacagtgttc tgttcgcgaa caaccaagcg tacactcgcg acaactaccg caaggctggc      600
atggcctacg tcatcgagga tctactgcac ttctgccggt gcatgtactc tatggcgttg      660 acaacatcc attacgcgct gctcacggct gtcgtcatct tttctgaccg gccagggttg       720
gagcagccgc aactggtgga agaaatccag cggtactacc tgaatacgct ccgcatctat      780
atcctgaacc agctgagcgg gtcggcgcgt tcgtccgtca tacggcaa gatcctctca         840 atcctctctg agctacgcac gctcggcatg caaaactcca acatgtgcat ctccctcaag      900
ctcaagaaca gaaagctgcc gccttcctc gaggagatct gggatgtggc ggacatgtcg      960

<210> SEQ ID NO 6
<211> LENGTH: 1878
<212> TYPE: DNA
<213> ORGANISM: Drosophila melanogaster
<220> FEATURE:
<221> NAME/KEY: misc_feature
<223> OTHER INFORMATION: Novel Sequence

<400> SEQUENCE: 6
ggacctgcgc cacgggtgca agaggagctg tgcctggttt gcggcgacag ggcctccggc      60
taccactaca acgccctcac ctgtgagggc tgcaaggggt tctttcgacg cagcgttacg     120
```

-continued

```
aagagcgccg tctactgctg caagttcggg cgcgcctgcg aaatggacat gtacatgagg      180
cgaaagtgtc aggagtgccg cctgaaaaag tgcctggccg tgggtatgcg gccggaatgc      240
gtcgtcccgg agaaccaatg tgcgatgaag cggcgcgaaa agaaggccca aggagaag       300 gacaaaatga ccacttcgcc gagctctcag catggcggca atggcagctt ggcctctggt      360
ggcggccaag actttgttaa gaaggagatt cttgacctta tgacatgcga gccgccccag      420
catgccacta ttccgctact acctgatgaa atattggcca agtgtcaagc gcgcaatata      480
ccttccttaa cgtacaatca gttggccgtt atatacaagt taatttggta ccaggatggc      540
tatgagcagc atctgaaga ggatctcagg cgtataatga gtcaacccga tgagaacgag       600
agccaaacgg acgtcagctt tcggcatata accgagataa ccatactcac ggtccagttg      660
attgttgagt ttgctaaagg tctaccagcg tttacaaaga taccccagga ggaccagatc      720
acgttactaa aggcctgctc gtcggaggtg atgatgctgc gtatggcacg acgctatgac      780
cacagctcgg actcaatatt cttcgcgaat aatagatcat atacgcggga ttcttacaaa      840
atggccggaa tggctgataa cattgaagac ctgctgcatt tctgccgcca aatgttctcg      900
atgaaggtgg acaacgtcga atacgcgctt ctcactgcca ttgtgatctt ctcggaccgg      960
ccgggcctgg agaaggccca actagtcgaa gcgatccaga gctactacat cgacacgcta      1020
cgcatttata tactcaaccg ccactgcggc gactcaatga gcctcgtctt ctacgcaaag      1080
ctgctctcga tcctcaccga gctgcgtacg ctgggcaacc agaacgccga gatgtgtttc      1140
tcactaaagc tcaaaaaccg caaactgccc aagttcctcg aggagatctg ggacgttcat      1200
gccatcccgc catcggtcca gtcgcacctt cagattaccc aggaggagaa cgagcgtctc      1260
gagcgggctg agcgtatgcg ggcatcggtt gggggcgcca ttaccgccgg cattgattgc      1320
gactctgcct ccacttcggc ggcggcagcc gcggcccagc atcagcctca gcctcagccc      1380
cagccccaac cctcctccct gacccagaac gattcccagc accagacaca gccgcagcta      1440
caacctcagc taccacctca gctgcaaggt caactgcaac cccagctcca accacagctt      1500
cagacgcaac tccagccaca gattcaacca cagccacagc tccttcccgt ctccgctccc      1560
gtgcccgcct ccgtaaccgc acctggttcc ttgtccgcgg tcagtacgag cagcgaatac      1620
atgggcggaa gtgcggccat aggacccatc acgccggcaa ccaccagcag tatcacggct      1680
gccgttaccg ctagctccac cacatcagcg gtaccgatgg gcaacggagt tggagtcggt      1740
gttggggtgg gcggcaacgt cagcatgtat gcgaacgccc agacggcgat ggccttgatg      1800
ggtgtagccc tgcattcgca ccaagagcag cttatcgggg gagtggcggt taagtcggag      1860
cactcgacga ctgcatag                                                   1878
```

<210> SEQ ID NO 7
<211> LENGTH: 1752
<212> TYPE: DNA
<213> ORGANISM: Drosophila melanogaster
<220> FEATURE:
<221> NAME/KEY: misc_feature
<223> OTHER INFORMATION: Novel Sequence

<400> SEQUENCE: 7

```
gccgtctact gctgcaagtt cgggcgcgcc tgcgaaatgg acatgtacat gaggcgaaag      60
tgtcaggagt gccgcctgaa aaagtgcctg gccgtgggta tgcggccgga atgcgtcgtc     120
ccggagaacc aatgtgcgat gaagcggcgc gaaaagaagg cccagaagga aggacaaa      180 atgaccactt cgccgagctc tcagcatggc ggcaatggca gcttggcctc tggtggcggc     240
```

-continued

```
caagactttg ttaagaagga gattcttgac cttatgacat gcgagccgcc ccagcatgcc      300
actattccgc tactacctga tgaaatattg gccaagtgtc aagcgcgcaa tataccttcc      360
ttaacgtaca atcagttggc cgttatatac aagttaattt ggtaccagga tggctatgag      420
cagccatctg aagaggatct caggcgtata atgagtcaac ccgatgagaa cgagagccaa      480
acggacgtca gctttcggca tataaccgag ataaccatac tcacggtcca gttgattgtt      540
gagtttgcta aaggtctacc agcgtttaca agataccccc aggaggacca gatcacgtta      600
ctaaaggcct gctcgtcgga ggtgatgatg ctgcgtatgg cacgacgcta tgaccacagc      660
tcggactcaa tattcttcgc gaataataga tcatatacgc gggattctta caaaatggcc      720
ggaatggctg ataacattga agacctgctg catttctgcc gccaaatgtt ctcgatgaag      780
gtggacaacg tcgaatacgc gcttctcact gccattgtga tcttctcgga ccggccgggc      840
ctggagaagg cccaactagt cgaagcgatc cagagctact acatcgacac gctacgcatt      900
tatatactca accgccactg cggcgactca atgagcctcg tcttctacgc aaagctgctc      960
tcgatcctca ccgagctgcg tacgctgggc aaccagaacg ccgagatgtg tttctcacta     1020
aagctcaaaa accgcaaact gcccaagttc ctcgaggaga tctgggacgt tcatgccatc     1080
ccgccatcgg tccagtcgca ccttcagatt acccaggagg agaacgagcg tctcgagcgg     1140
gctgagcgta tgcgggcatc ggttggggc gccattaccg ccggcattga ttgcgactct     1200
gcctccactt cggcggcggc agccgcggcc cagcatcagc ctcagcctca gcccagccc     1260 caaccctcct ccctgaccca gaacgattcc cagcaccaga cacagccgca gctacaacct     1320
cagctaccac ctcagctgca aggtcaactg caaccccagc tccaaccaca gcttcagacg     1380
caactccagc cacagattca accacagcca cagctccttc ccgtctccgc tcccgtgccc     1440
gcctccgtaa ccgcacctgg ttccttgtcc gcggtcagta cgagcagcga atacatgggc     1500
ggaagtgcgg ccataggacc catcacgccg gcaaccacca gcagtatcac ggctgccgtt     1560
accgctagct ccaccacatc agcggtaccg atgggcaacg gagttggagt cggtgttggg     1620
gtgggcggca acgtcagcat gtatgcgaac gcccagacgg cgatggcctt gatgggtgta     1680
gccctgcatt cgcaccaaga gcagcttatc gggggagtgg cggttaagtc ggagcactcg     1740
acgactgcat ag                                                          1752
```

<210> SEQ ID NO 8
<211> LENGTH: 1650
<212> TYPE: DNA
<213> ORGANISM: Drosophila melanogaster
<220> FEATURE:
<221> NAME/KEY: misc_feature
<223> OTHER INFORMATION: Novel Sequence

<400> SEQUENCE: 8

```
cggccggaat gcgtcgtccc ggagaaccaa tgtgcgatga agcggcgcga aaagaaggcc       60
cagaaggaga aggacaaaat gaccacttcg ccgagctctc agcatggcgg caatggcagc      120
ttggcctctg gtggcggcca agactttgtt aagaaggaga ttcttgacct tatgacatgc      180
gagccgcccc agcatgccac tattccgcta ctacctgatg aaatattggc caagtgtcaa      240
gcgcgcaata taccttcctt aacgtacaat cagttggccg ttatatacaa gttaatttgg      300
taccaggatg gctatgagca gccatctgaa gaggatctca ggcgtataat gagtcaaccc      360
gatgagaacg agagccaaac ggacgtcagc tttcggcata taaccgagat aaccatactc      420
acggtccagt tgattgttga gtttgctaaa ggtctaccag cgtttacaaa gataccccag      480
```

| | |
|---|---|
| gaggaccaga tcacgttact aaaggcctgc tcgtcggagg tgatgatgct gcgtatggca | 540 |
| cgacgctatg accacagctc ggactcaata ttcttcgcga ataatagatc atatacgcgg | 600 |
| gattcttaca aaatgccgg aatggctgat aacattgaag acctgctgca tttctgccgc | 660 |
| caaatgttct cgatgaaggt ggacaacgtc gaatacgcgc ttctcactgc cattgtgatc | 720 |
| ttctcggacc ggccgggcct ggagaaggcc caactagtcg aagcgatcca gagctactac | 780 |
| atcgacacgc tacgcattta tactcaaac cgccactgcg gcgactcaat gagcctcgtc | 840 |
| ttctacgcaa agctgctctc gatcctcacc gagctgcgta cgctgggcaa ccagaacgcc | 900 |
| gagatgtgtt tctcactaaa gctcaaaaac cgcaaactgc ccaagttcct cgaggagatc | 960 |
| tgggacgttc atgccatccc gccatcggtc cagtcgcacc ttcagattac ccaggaggag | 1020 |
| aacgagcgtc tcgagcgggc tgagcgtatg cgggcatcgg ttggggggcgc cattaccgcc | 1080 |
| ggcattgatt gcgactctgc ctccacttcg gcggcggcag ccgcggccca gcatcagcct | 1140 |
| cagcctcagc cccagcccca accctcctcc ctgacccaga acgattccca gcaccagaca | 1200 |
| cagccgcagc tacaacctca gctaccacct cagctgcaag gtcaactgca accccagctc | 1260 |
| caaccacagc ttcagacgca actccagcca cagattcaac cacagccaca gctccttccc | 1320 |
| gtctccgctc ccgtgcccgc ctccgtaacc gcacctggtt ccttgtccgc ggtcagtacg | 1380 |
| agcagcgaat acatgggcgg aagtgcggcc ataggaccca tcacgccggc aaccaccagc | 1440 |
| agtatcacgg ctgccgttac cgctagctcc accacatcag cggtaccgat gggcaacgga | 1500 |
| gttggagtcg gtgttggggt gggcggcaac gtcagcatgt atgcgaacgc ccagacggcg | 1560 |
| atggccttga tgggtgtagc cctgcattcg caccaagagc agcttatcgg gggagtggcg | 1620 |
| gttaagtcgg agcactcgac gactgcatag | 1650 |

<210> SEQ ID NO 9
<211> LENGTH: 1338
<212> TYPE: DNA
<213> ORGANISM: Drosophila melanogaster
<220> FEATURE:
<221> NAME/KEY: misc_feature
<223> OTHER INFORMATION: Novel Sequence

<400> SEQUENCE: 9

| | |
|---|---|
| tatgagcagc catctgaaga ggatctcagg cgtataatga gtcaacccga tgagaacgag | 60 |
| agccaaacgg acgtcagctt tcggcatata accgagataa ccatactcac ggtccagttg | 120 |
| attgttgagt ttgctaaagg tctaccagcg tttacaaaga taccccagga ggaccagatc | 180 |
| acgttactaa aggcctgctc gtcggaggtg atgatgctgc gtatggcacg acgctatgac | 240 |
| cacagctcgg actcaatatt cttcgcgaat aatagatcat atacgcggga ttcttacaaa | 300 |
| atggccggaa tggctgataa cattgaagac ctgctgcatt tctgccgcca aatgttctcg | 360 |
| atgaaggtgg acaacgtcga atacgcgctt ctcactgcca ttgtgatctt ctcggaccgg | 420 |
| ccgggcctgg agaaggccca actagtcgaa gcgatccaga gctactacat cgacacgcta | 480 |
| cgcatttata ctcaaccg ccactgcggc gactcaatga gcctcgtctt ctacgcaaag | 540 |
| ctgctctcga tcctcaccga gctgcgtacg ctgggcaacc agaacgccga gatgtgtttc | 600 |
| tcactaaagc tcaaaaaccg caaactgccc aagttcctcg aggagatctg gacgttcat | 660 |
| gccatcccgc catcggtcca gtcgcacctt cagattaccc aggaggagaa cgagcgtctc | 720 |
| gagcgggctg agcgtatgcg ggcatcggtt ggggcgcca ttaccgccgg cattgattgc | 780 |
| gactctgcct ccacttcggc ggcggcagcc gcggcccagc atcagcctca gcctcagccc | 840 |

```
cagccccaac cctcctccct gacccagaac gattcccagc accagacaca gccgcagcta    900
caacctcagc taccacctca gctgcaaggt caactgcaac cccagctcca accacagctt    960
cagacgcaac tccagccaca gattcaacca cagccacagc tccttcccgt ctccgctccc   1020
gtgcccgcct ccgtaaccgc acctggttcc ttgtccgcgg tcagtacgag cagcgaatac   1080
atgggcggaa gtgcggccat aggacccatc acgccgcaa ccaccagcag tatcacggct   1140
gccgttaccg ctagctccac cacatcagcg gtaccgatgg gcaacggagt ggagtcggt    1200 gttggggtgg gcggcaacgt cagcatgtat gcgaacgccc agacggcgat ggccttgatg   1260
ggtgtagccc tgcattcgca ccaagagcag cttatcgggg gagtggcggt taagtcggag   1320
cactcgacga ctgcatag                                                 1338
```

<210> SEQ ID NO 10
<211> LENGTH: 969
<212> TYPE: DNA
<213> ORGANISM: Drosophila melanogaster
<220> FEATURE:
<221> NAME/KEY: misc_feature
<223> OTHER INFORMATION: Novel Sequence

<400> SEQUENCE: 10

```
cggccggaat gcgtcgtccc ggagaaccaa tgtgcgatga agcggcgcga aaagaaggcc     60
cagaaggaga aggacaaaat gaccacttcg ccgagctctc agcatggcgg caatggcagc    120
ttggcctctg gtggcggcca agactttgtt aagaaggaga ttcttgacct tatgacatgc    180
gagccgcccc agcatgccac tattccgcta ctacctgatg aaatattggc caagtgtcaa    240
gcgcgcaata taccttcctt aacgtacaat cagttggccg ttatatacaa gttaatttgg    300
taccaggatg gctatgagca gccatctgaa gaggatctca ggcgtataat gagtcaaccc    360
gatgagaacg agagccaaac ggacgtcagc tttcggcata taaccgagat aaccatactc    420
acggtccagt tgattgttga gtttgctaaa ggtctaccag cgtttacaaa gatacccag    480 gaggaccaga tcacgttact aaaggcctgc tcgtcggagg tgatgatgct gcgtatggca    540
cgacgctatg accacagctc ggactcaata ttcttcgcga ataatagatc atatacgcgg    600
gattcttaca aaatggccgg aatggctgat aacattgaag acctgctgca tttctgccgc    660
caaatgttct cgatgaaggt ggacaacgtc gaatacgcgc ttctcactgc cattgtgatc    720
ttctcggacc ggccgggcct ggagaaggcc caactagtcg aagcgatcca gagctactac    780
atcgacacgc tacgcattta tatactcaac cgccactgcg gcgactcaat gagcctcgtc    840
ttctacgcaa agctgctctc gatcctcacc gagctgcgta cgctgggcaa ccagaacgcc    900
gagatgtgtt tctcactaaa gctcaaaaac cgcaaactgc ccaagttcct cgaggagatc    960
tgggacgtt                                                            969
```

<210> SEQ ID NO 11
<211> LENGTH: 412
<212> TYPE: PRT
<213> ORGANISM: Choristoneura fumiferana
<220> FEATURE:
<221> NAME/KEY: misc_feature
<223> OTHER INFORMATION: Novel Sequence

<400> SEQUENCE: 11

Lys Gly Pro

```
                 20                  25                  30
Lys Gly Phe Phe Arg Arg Ser Val Thr Lys Asn Ala Val Tyr Ile Cys
             35                  40                  45

Lys Phe Gly His Ala Cys Glu Met Asp Met Tyr Met Arg Arg Lys Cys
         50                  55                  60

Gln Glu Cys Arg Leu Lys Lys Cys Leu Ala Val Gly Met Arg Pro Glu
 65                  70                  75                  80

Cys Val Val Pro Glu Thr Gln Cys Ala Met Lys Arg Lys Glu Lys Lys
                 85                  90                  95

Ala Gln Lys Glu Lys Asp Lys Leu Pro Val Ser Thr Thr Val Asp
            100                 105                 110

Asp His Met Pro Pro Ile Met Gln Cys Glu Pro Pro Pro Glu Ala
            115                 120                 125

Ala Arg Ile His Glu Val Val Pro Arg Phe Leu Ser Asp Lys Leu Leu
            130                 135                 140

Glu Thr Asn Arg Gln Lys Asn Ile Pro Gln Leu Thr Ala Asn Gln Gln
145                 150                 155                 160

Phe Leu Ile Ala Arg Leu Ile Trp Tyr Gln Asp Gly Tyr Glu Gln Pro
                165                 170                 175

Ser Asp Glu Asp Leu Lys Arg Ile Thr Gln Thr Trp Gln Gln Ala Asp
            180                 185                 190

Asp Glu Asn Glu Glu Ser Asp Thr Pro Phe Arg Gln Ile Thr Glu Met
            195                 200                 205

Thr Ile Leu Thr Val Gln Leu Ile Val Glu Phe Ala Lys Gly Leu Pro
210                 215                 220

Gly Phe Ala Lys Ile Ser Gln Pro Asp Gln Ile Thr Leu Leu Lys Ala
225                 230                 235                 240

Cys Ser Ser Glu Val Met Met Leu Arg Val Ala Arg Arg Tyr Asp Ala
                245                 250                 255

Ala Ser Asp Ser Val Leu Phe Ala Asn Asn Gln Ala Tyr Thr Arg Asp
            260                 265                 270

Asn Tyr Arg Lys Ala Gly Met Ala Tyr Val Ile Glu Asp Leu Leu His
        275                 280                 285

Phe Cys Arg Cys Met Tyr Ser Met Ala Leu Asp Asn Ile His Tyr Ala
290                 295                 300

Leu Leu Thr Ala Val Val Ile Phe Ser Asp Arg Pro Gly Leu Glu Gln
305                 310                 315                 320

Pro Gln Leu Val Glu Glu Ile Gln Arg Tyr Tyr Leu Asn Thr Leu Arg
                325                 330                 335

Ile Tyr Ile Leu Asn Gln Leu Ser Gly Ser Ala Arg Ser Ser Val Ile
            340                 345                 350

Tyr Gly Lys Ile Leu Ser Ile Leu Ser Glu Leu Arg Thr Leu Gly Met
        355                 360                 365

Gln Asn Ser Asn Met Cys Ile Ser Leu Lys Leu Lys Asn Arg Lys Leu
        370                 375                 380

Pro Pro Phe Leu Glu Glu Ile Trp Asp Val Ala Asp Met Ser His Thr
385                 390                 395                 400

Gln Pro Pro Pro Ile Leu Glu Ser Pro Thr Asn Leu
                405                 410

<210> SEQ ID NO 12
<211> LENGTH: 412
<212> TYPE: PRT
<213> ORGANISM: Choristoneura fumiferana
```

```
<220> FEATURE:
<221> NAME/KEY: misc_feature
<223> OTHER INFORMATION: Novel Sequence

<400> SEQUENCE: 12

Lys Gly Pro Ala Pro Arg Gln Gln Glu Glu Leu Cys Leu Val Cys Gly
1               5                   10                  15

Asp Arg Ala Ser Gly Tyr His Tyr Asn Ala Leu Thr Cys Glu Gly Cys
            20                  25                  30

Lys Gly Phe Phe Arg Arg Ser Val Thr Lys Asn Ala Val Tyr Ile Cys
        35                  40                  45

Lys Phe Gly His Ala Cys Glu Met Asp Met Tyr Met Arg Arg Lys Cys
    50                  55                  60

Gln Glu Cys Arg Leu Lys Lys Cys Leu Ala Val Gly Met Arg Pro Glu
65                  70                  75                  80

Cys Val Val Pro Glu Thr Gln Cys Ala Met Lys Arg Lys Glu Lys Lys
                85                  90                  95

Ala Gln Lys Glu Lys Asp Lys Leu Pro Val Ser Thr Thr Thr Val Asp
            100                 105                 110

Asp His Met Pro Pro Ile Met Gln Cys Glu Pro Pro Pro Pro Glu Ala
        115                 120                 125

Ala Arg Ile His Glu Val Val Pro Arg Phe Leu Ser Asp Lys Leu Leu
    130                 135                 140

Glu Thr Asn Arg Gln Lys Asn Ile Pro Gln Leu Thr Ala Asn Gln Gln
145                 150                 155                 160

Phe Leu Ile Ala Arg Leu Ile Trp Tyr Gln Asp Gly Tyr Glu Gln Pro
                165                 170                 175

Ser Asp Glu Asp Leu Lys Arg Ile Thr Gln Thr Trp Gln Gln Ala Asp
            180                 185                 190

Asp Glu Asn Glu Glu Ser Asp Thr Pro Phe Arg Gln Ile Thr Glu Met
        195                 200                 205

Thr Ile Leu Thr Val Gln Leu Ile Val Glu Phe Ala Lys Gly Leu Pro
210                 215                 220

Gly Phe Ala Lys Ile Ser Gln Pro Asp Gln Ile Thr Leu Leu Lys Ala
225                 230                 235                 240

Cys Ser Ser Glu Val Met Met Leu Arg Val Ala Arg Arg Tyr Asp Ala
                245                 250                 255

Ala Ser Asp Ser Val Leu Phe Ala Asn Asn Gln Ala Tyr Thr Arg Asp
            260                 265                 270

Asn Tyr Arg Lys Ala Gly Met Ala Tyr Val Ile Glu Asp Leu Leu His
        275                 280                 285

Phe Cys Arg Cys Met Tyr Ser Met Ala Leu Asp Asn Ile His Tyr Ala
    290                 295                 300

Leu Leu Thr Ala Val Val Ile Phe Ser Asp Arg Pro Gly Leu Glu Gln
305                 310                 315                 320

Pro Gln Leu Val Glu Glu Ile Gln Arg Tyr Tyr Leu Asn Thr Leu Arg
                325                 330                 335

Ile Tyr Ile Leu Asn Gln Leu Ser Gly Ser Ala Arg Ser Ser Val Ile
            340                 345                 350

Tyr Gly Lys Ile Leu Ser Ile Leu Ser Glu Leu Arg Thr Leu Gly Met
        355                 360                 365

Gln Asn Ser Asn Met Cys Ile Ser Leu Lys Leu Lys Asn Arg Lys Leu
    370                 375                 380

Pro Pro Phe Leu Glu Glu Ile Trp Asp Val Ala Asp Met Ser His Thr
```

```
                385                 390                 395                 400
Gln Pro Pro Ile Leu Glu Ser Pro Thr Asn Leu
                405                 410
```

<210> SEQ ID NO 13
<211> LENGTH: 334
<212> TYPE: PRT
<213> ORGANISM: Choristoneura fumiferana
<220> FEATURE:
<221> NAME/KEY: misc_feature
<223> OTHER INFORMATION: Novel Sequence

<400> SEQUENCE: 13

```
Pro Glu Cys Val Val Pro Glu Thr Gln Cys Ala Met Lys Arg Lys Glu
1               5                   10                  15

Lys Lys Ala Gln Lys Glu Lys Asp Lys Leu Pro Val Ser Thr Thr Thr
            20                  25                  30

Val Asp Asp His Met Pro Pro Ile Met Gln Cys Glu Pro Pro Pro Pro
        35                  40                  45

Glu Ala Ala Arg Ile His Glu Val Val Pro Arg Phe Leu Ser Asp Lys
    50                  55                  60

Leu Leu Glu Thr Asn Arg Gln Lys Asn Ile Pro Gln Leu Thr Ala Asn
65                  70                  75                  80

Gln Gln Phe Leu Ile Ala Arg Leu Ile Trp Tyr Gln Asp Gly Tyr Glu
                85                  90                  95

Gln Pro Ser Asp Glu Asp Leu Lys Arg Ile Thr Gln Thr Trp Gln Gln
            100                 105                 110

Ala Asp Asp Glu Asn Glu Glu Ser Asp Thr Pro Phe Arg Gln Ile Thr
        115                 120                 125

Glu Met Thr Ile Leu Thr Val Gln Leu Ile Val Glu Phe Ala Lys Gly
    130                 135                 140

Leu Pro Gly Phe Ala Lys Ile Ser Gln Pro Asp Gln Ile Thr Leu Leu
145                 150                 155                 160

Lys Ala Cys Ser Ser Glu Val Met Met Leu Arg Val Ala Arg Arg Tyr
                165                 170                 175

Asp Ala Ala Ser Asp Ser Val Leu Phe Ala Asn Asn Gln Ala Tyr Thr
            180                 185                 190

Arg Asp Asn Tyr Arg Lys Ala Gly Met Ala Tyr Val Ile Glu Asp Leu
        195                 200                 205

Leu His Phe Cys Arg Cys Met Tyr Ser Met Ala Leu Asp Asn Ile His
    210                 215                 220

Tyr Ala Leu Leu Thr Ala Val Ile Phe Ser Asp Arg Pro Gly Leu
225                 230                 235                 240

Glu Gln Pro Gln Leu Val Glu Ile Gln Arg Tyr Tyr Leu Asn Thr
                245                 250                 255

Leu Arg Ile Tyr Ile Leu Asn Gln Leu Ser Gly Ser Ala Arg Ser Ser
            260                 265                 270

Val Ile Tyr Gly Lys Ile Leu Ser Ile Leu Ser Glu Leu Arg Thr Leu
        275                 280                 285

Gly Met Gln Asn Ser Asn Met Cys Ile Ser Leu Lys Leu Lys Asn Arg
    290                 295                 300

Lys Leu Pro Pro Phe Leu Glu Glu Ile Trp Asp Val Ala Asp Met Ser
305                 310                 315                 320

His Thr Gln Pro Pro Ile Leu Glu Ser Pro Thr Asn Leu
                325                 330
```

```
<210> SEQ ID NO 14
<211> LENGTH: 244
<212> TYPE: PRT
<213> ORGANISM: Choristoneura fumiferana
<220> FEATURE:
<221> NAME/KEY: misc_feature
<223> OTHER INFORMATION: Novel Sequence

<400> SEQUENCE: 14
```

Tyr G

```
                    50                  55                  60

Leu Leu Glu Thr Asn Arg Gln Lys Asn Ile Pro Gln Leu Thr Ala Asn
 65                  70                  75                  80

Gln Gln Phe Leu Ile Ala Arg Leu Ile Trp Tyr Gln Asp Gly Tyr Glu
                     85                  90                  95

Gln Pro Ser Asp Glu Asp Leu Lys Arg Ile Thr Gln Thr Trp Gln Gln
                100                 105                 110

Ala Asp Asp Glu Asn Glu Ser Asp Thr Pro Phe Arg Gln Ile Thr
                115                 120                 125

Glu Met Thr Ile Leu Thr Val Gln Leu Ile Val Glu Phe Ala Lys Gly
130                 135                 140

Leu Pro Gly Phe Ala Lys Ile Ser Gln Pro Asp Gln Ile Thr Leu Leu
145                 150                 155                 160

Lys Ala Cys Ser Ser Glu Val Met Met Leu Arg Val Ala Arg Arg Tyr
                165                 170                 175

Asp Ala Ala Ser Asp Ser Val Leu Phe Ala Asn Asn Gln Ala Tyr Thr
                180                 185                 190

Arg Asp Asn Tyr Arg Lys Ala Gly Met Ala Tyr Val Ile Glu Asp Leu
                195                 200                 205

Leu His Phe Cys Arg Cys Met Tyr Ser Met Ala Leu Asp Asn Ile His
                210                 215                 220

Tyr Ala Leu Leu Thr Ala Val Val Ile Phe Ser Asp Arg Pro Gly Leu
225                 230                 235                 240

Glu Gln Pro Gln Leu Val Glu Glu Ile Gln Arg Tyr Tyr Leu Asn Thr
                245                 250                 255

Leu Arg Ile Tyr Ile Leu Asn Gln Leu Ser Gly Ser Ala Arg Ser Ser
                260                 265                 270

Val Ile Tyr Gly Lys Ile Leu Ser Ile Leu Ser Glu Leu Arg Thr Leu
                275                 280                 285

Gly Met Gln Asn Ser Asn Met Cys Ile Ser Leu Lys Leu Lys Asn Arg
                290                 295                 300

Lys Leu Pro Pro Phe Leu Glu Glu Ile Trp Asp Val Ala Asp Met Ser
305                 310                 315                 320

<210> SEQ ID NO 16
<211> LENGTH: 625
<212> TYPE: PRT
<213> ORGANISM: Drosophila melanogaster
<220> FEATURE:
<221> NAME/KEY: misc_feature
<223> OTHER INFORMATION: Novel Sequence

<400> SEQUENCE: 16

Gly Pro Ala Pro Arg Val Gln Glu Glu Leu Cys Leu Val Cys Gly Asp
 1               5                  10                  15

Arg Ala Ser Gly Tyr His Tyr Asn Ala Leu Thr Cys Glu Gly Cys Lys
                20                  25                  30

Gly Phe Phe Arg Arg Ser Val Thr Lys Ser Ala Val Tyr Cys Cys Lys
                35                  40                  45

Phe Gly Arg Ala Cys Glu Met Asp Met Tyr Met Arg Arg Lys Cys Gln
 50                  55                  60

Glu Cys Arg Leu Lys Lys Cys Leu Ala Val Gly Met Arg Pro Glu Cys
 65                  70                  75                  80

Val Val Pro Glu Asn Gln Cys Ala Met Lys Arg Arg Glu Lys Lys Ala
                85                  90                  95
```

-continued

```
Gln Lys Glu Lys Asp Lys Met Thr Thr Ser Pro Ser Gln His Gly
            100                 105                 110
Gly Asn Gly Ser Leu Ala Ser Gly Gly Gln Asp Phe Val Lys Lys
            115                 120                 125
Glu Ile Leu Asp Leu Met Thr Cys Glu Pro Pro Gln His Ala Thr Ile
    130                 135                 140
Pro Leu Leu Pro Asp Glu Ile Leu Ala Lys Cys Gln Ala Arg Asn Ile
145                 150                 155                 160
Pro Ser Leu Thr Tyr Asn Gln Leu Ala Val Ile Tyr Lys Leu Ile Trp
                165                 170                 175
Tyr Gln Asp Gly Tyr Glu Gln Pro Ser Glu Asp Leu Arg Arg Ile
                180                 185                 190
Met Ser Gln Pro Asp Glu Asn Glu Ser Gln Thr Asp Val Ser Phe Arg
            195                 200                 205
His Ile Thr Glu Ile Thr Ile Leu Thr Val Gln Leu Ile Val Glu Phe
    210                 215                 220
Ala Lys Gly Leu Pro Ala Phe Thr Lys Ile Pro Gln Glu Asp Gln Ile
225                 230                 235                 240
Thr Leu Leu Lys Ala Cys Ser Ser Glu Val Met Met Leu Arg Met Ala
                245                 250                 255
Arg Arg Tyr Asp His Ser Ser Asp Ser Ile Phe Phe Ala Asn Asn Arg
            260                 265                 270
Ser Tyr Thr Arg Asp Ser Tyr Lys Met Ala Gly Met Ala Asp Asn Ile
            275                 280                 285
Glu Asp Leu Leu His Phe Cys Arg Gln Met Phe Ser Met Lys Val Asp
    290                 295                 300
Asn Val Glu Tyr Ala Leu Leu Thr Ala Ile Val Ile Phe Ser Asp Arg
305                 310                 315                 320
Pro Gly Leu Glu Lys Ala Gln Leu Val Glu Ala Ile Gln Ser Tyr Tyr
                325                 330                 335
Ile Asp Thr Leu Arg Ile Tyr Ile Leu Asn Arg His Cys Gly Asp Ser
                340                 345                 350
Met Ser Leu Val Phe Tyr Ala Lys Leu Leu Ser Ile Leu Thr Glu Leu
            355                 360                 365
Arg Thr Leu Gly Asn Gln Asn Ala Glu Met Cys Phe Ser Leu Lys Leu
    370                 375                 380
Lys Asn Arg Lys Leu Pro Lys Phe Leu Glu Glu Ile Trp Asp Val His
385                 390                 395                 400
Ala Ile Pro Pro Ser Val Gln Ser His Leu Gln Ile Thr Gln Glu Glu
                405                 410                 415
Asn Glu Arg Leu Glu Arg Ala Glu Arg Met Arg Ala Ser Val Gly Gly
            420                 425                 430
Ala Ile Thr Ala Gly Ile Asp Cys Asp Ser Ala Ser Thr Ser Ala Ala
    435                 440                 445
Ala Ala Ala Ala Gln His Gln Pro Gln Pro Gln Pro Gln Pro Gln Pro
450                 455                 460
Ser Ser Leu Thr Gln Asn Asp Ser Gln His Gln Thr Gln Pro Gln Leu
465                 470                 475                 480
Gln Pro Gln Leu Pro Pro Gln Leu Gln Gly Gln Leu Gln Pro Gln Leu
                485                 490                 495
Gln Pro Gln Leu Gln Thr Gln Leu Gln Pro Gln Ile Gln Pro Gln Pro
            500                 505                 510
Gln Leu Leu Pro Val Ser Ala Pro Val Pro Ala Ser Val Thr Ala Pro
```

```
                    515                 520                 525
Gly Ser Leu Ser Ala Val Ser Thr Ser Ser Glu Tyr Met Gly Gly Ser
        530                 535                 540

Ala Ala Ile Gly Pro Ile Thr Pro Ala Thr Thr Ser Ser Ile Thr Ala
545                 550                 555                 560

Ala Val Thr Ala Ser Ser Thr Thr Ser Ala Val Pro Met Gly Asn Gly
                565                 570                 575

Val Gly Val Gly Val Gly Val Gly Gly Asn Val Ser Met Tyr Ala Asn
            580                 585                 590

Ala Gln Thr Ala Met Ala Leu Met Gly Val Ala Leu His Ser His Gln
        595                 600                 605

Glu Gln Leu Ile Gly Gly Val Ala Val Lys Ser Glu His Ser Thr Thr
    610                 615                 620

Ala
625

<210> SEQ ID NO 17
<211> LENGTH: 583
<212> TYPE: PRT
<213> ORGANISM: Drosophila melanogaster
<220> FEATURE:
<221> NAME/KEY: misc_feature
<223> OTHER INFORMATION: Novel Sequence

<400> SEQUENCE: 17

Ala Val Tyr Cys Cys Lys Phe Gly Arg Ala Cys Glu Met Asp Met Tyr
1               5                   10                  15

Met Arg Arg Lys Cys Gln Glu Cys Arg Leu Lys Lys Cys Leu Ala Val
                20                  25                  30

Gly Met Arg Pro Glu Cys Val Val Pro Glu Asn Gln Cys Ala Met Lys
            35                  40                  45

Arg Arg Glu Lys Lys Ala Gln Lys Glu Lys Asp Lys Met Thr Thr Ser
        50                  55                  60

Pro Ser Ser Gln His Gly Gly Asn Gly Ser Leu Ala Ser Gly Gly Gly
65                  70                  75                  80

Gln Asp Phe Val Lys Lys Glu Ile Leu Asp Leu Met Thr Cys Glu Pro
                85                  90                  95

Pro Gln His Ala Thr Ile Pro Leu Leu Pro Asp Glu Ile Leu Ala Lys
            100                 105                 110

Cys Gln Ala Arg Asn Ile Pro Ser Leu Thr Tyr Asn Gln Leu Ala Val
        115                 120                 125

Ile Tyr Lys Leu Ile Trp Tyr Gln Asp Gly Tyr Glu Gln Pro Ser Glu
    130                 135                 140

Glu Asp Leu Arg Arg Ile Met Ser Gln Pro Asp Glu Asn Glu Ser Gln
145                 150                 155                 160

Thr Asp Val Ser Phe Arg His Ile Thr Glu Ile Thr Ile Leu Thr Val
                165                 170                 175

Gln Leu Ile Val Glu Phe Ala Lys Gly Leu Pro Ala Phe Thr Lys Ile
            180                 185                 190

Pro Gln Glu Asp Gln Ile Thr Leu Leu Lys Ala Cys Ser Ser Glu Val
        195                 200                 205

Met Met Leu Arg Met Ala Arg Arg Tyr Asp His Ser Ser Asp Ser Ile
    210                 215                 220

Phe Phe Ala Asn Asn Arg Ser Tyr Thr Arg Asp Ser Tyr Lys Met Ala
225                 230                 235                 240
```

```
Gly Met Ala Asp Asn Ile Glu Asp Leu Leu His Phe Cys Arg Gln Met
                245                 250                 255

Phe Ser Met Lys Val Asp Asn Val Glu Tyr Ala Leu Leu Thr Ala Ile
            260                 265                 270

Val Ile Phe Ser Asp Arg Pro Gly Leu Glu Lys Ala Gln Leu Val Glu
        275                 280                 285

Ala Ile Gln Ser Tyr Tyr Ile Asp Thr Leu Arg Ile Tyr Ile Leu Asn
    290                 295                 300

Arg His Cys Gly Asp Ser Met Ser Leu Val Phe Tyr Ala Lys Leu Leu
305                 310                 315                 320

Ser Ile Leu Thr Glu Leu Arg Thr Leu Gly Asn Gln Asn Ala Glu Met
                325                 330                 335

Cys Phe Ser Leu Lys Leu Lys Asn Arg Lys Leu Pro Lys Phe Leu Glu
            340                 345                 350

Glu Ile Trp Asp Val His Ala Ile Pro Pro Ser Val Gln Ser His Leu
        355                 360                 365

Gln Ile Thr Gln Glu Glu Asn Glu Arg Leu Glu Arg Ala Glu Arg Met
    370                 375                 380

Arg Ala Ser Val Gly Gly Ala Ile Thr Ala Gly Ile Asp Cys Asp Ser
385                 390                 395                 400

Ala Ser Thr Ser Ala Ala Ala Ala Ala Gln His Gln Pro Gln Pro
                405                 410                 415

Gln Pro Gln Pro Gln Pro Ser Ser Leu Thr Gln Asn Asp Ser Gln His
            420                 425                 430

Gln Thr Gln Pro Gln Leu Gln Pro Gln Leu Pro Gln Leu Gln Gly
        435                 440                 445

Gln Leu Gln Pro Gln Leu Gln Pro Gln Leu Gln Thr Gln Leu Gln Pro
    450                 455                 460

Gln Ile Gln Pro Gln Pro Gln Leu Leu Pro Val Ser Ala Pro Val Pro
465                 470                 475                 480

Ala Ser Val Thr Ala Pro Gly Ser Leu Ser Ala Val Ser Thr Ser Ser
                485                 490                 495

Glu Tyr Met Gly Gly Ser Ala Ala Ile Gly Pro Ile Thr Pro Ala Thr
            500                 505                 510

Thr Ser Ser Ile Thr Ala Ala Val Thr Ala Ser Ser Thr Thr Ser Ala
        515                 520                 525

Val Pro Met Gly Asn Gly Val Gly Val Gly Val Gly Val Gly Gly Asn
    530                 535                 540

Val Ser Met Tyr Ala Asn Ala Gln Thr Ala Met Ala Leu Met Gly Val
545                 550                 555                 560

Ala Leu His Ser His Gln Glu Gln Leu Ile Gly Gly Val Ala Val Lys
                565                 570                 575

Ser Glu His Ser Thr Thr Ala
            580

<210> SEQ ID NO 18
<211> LENGTH: 549
<212> TYPE: PRT
<213> ORGANISM: Drosophila melanogaster
<220> FEATURE:
<221> NAME/KEY: misc_feature
<223> OTHER INFORMATION: Novel Sequence

<400> SEQUENCE: 18

Arg Pro Glu Cys Val Val Pro Glu Asn Gln Cys Ala Met Lys Arg Arg
1               5                   10                  15
```

```
Glu Lys Lys Ala Gln Lys Glu Lys Asp Lys Met Thr Thr Ser Pro Ser
                20              25                  30

Ser Gln His Gly Gly Asn Gly Ser Leu Ala Ser Gly Gly Gly Gln Asp
            35                  40                  45

Phe Val Lys Lys Glu Ile Leu Asp Leu Met Thr Cys Glu Pro Pro Gln
         50                  55                  60

His Ala Thr Ile Pro Leu Leu Pro Asp Glu Ile Leu Ala Lys Cys Gln
 65                  70                  75                  80

Ala Arg Asn Ile Pro Ser Leu Thr Tyr Asn Gln Leu Ala Val Ile Tyr
                 85                  90                  95

Lys Leu Ile Trp Tyr Gln Asp Gly Tyr Glu Gln Pro Ser Glu Glu Asp
                100                 105                 110

Leu Arg Arg Ile Met Ser Gln Pro Asp Glu Asn Glu Ser Gln Thr Asp
                115                 120                 125

Val Ser Phe Arg His Ile Thr Glu Ile Thr Ile Leu Thr Val Gln Leu
    130                 135                 140

Ile Val Glu Phe Ala Lys Gly Leu Pro Ala Phe Thr Lys Ile Pro Gln
145                 150                 155                 160

Glu Asp Gln Ile Thr Leu Leu Lys Ala Cys Ser Ser Glu Val Met Met
                165                 170                 175

Leu Arg Met Ala Arg Arg Tyr Asp His Ser Ser Asp Ser Ile Phe Phe
                180                 185                 190

Ala Asn Asn Arg Ser Tyr Thr Arg Asp Ser Tyr Lys Met Ala Gly Met
                195                 200                 205

Ala Asp Asn Ile Glu Asp Leu Leu His Phe Cys Arg Gln Met Phe Ser
210                 215                 220

Met Lys Val Asp Asn Val Glu Tyr Ala Leu Leu Thr Ala Ile Val Ile
225                 230                 235                 240

Phe Ser Asp Arg Pro Gly Leu Glu Lys Ala Gln Leu Val Glu Ala Ile
                245                 250                 255

Gln Ser Tyr Tyr Ile Asp Thr Leu Arg Ile Tyr Ile Leu Asn Arg His
                260                 265                 270

Cys Gly Asp Ser Met Ser Leu Val Phe Tyr Ala Lys Leu Leu Ser Ile
    275                 280                 285

Leu Thr Glu Leu Arg Thr Leu Gly Asn Gln Asn Ala Glu Met Cys Phe
    290                 295                 300

Ser Leu Lys Leu Lys Asn Arg Lys Leu Pro Lys Phe Leu Glu Glu Ile
305                 310                 315                 320

Trp Asp Val His Ala Ile Pro Pro Ser Val Gln Ser His Leu Gln Ile
                325                 330                 335

Thr Gln Glu Glu Asn Glu Arg Leu Glu Arg Ala Glu Arg Met Arg Ala
                340                 345                 350

Ser Val Gly Gly Ala Ile Thr Ala Gly Ile Asp Cys Asp Ser Ala Ser
    355                 360                 365

Thr Ser Ala Ala Ala Ala Ala Gln His Gln Pro Gln Pro Gln Pro Gln
370                 375                 380

Gln Pro Gln Pro Ser Ser Leu Thr Gln Asn Asp Ser Gln His Gln Thr
385                 390                 395                 400

Gln Pro Gln Leu Gln Pro Gln Leu Pro Pro Gln Leu Gly Gln Leu
                405                 410                 415

Gln Pro Gln Leu Gln Pro Gln Leu Gln Thr Gln Leu Gln Pro Gln Ile
                420                 425                 430
```

```
Gln Pro Gln Pro Gln Leu Leu Pro Val Ser Ala Pro Val Pro Ala Ser
        435                 440                 445

Val Thr Ala Pro Gly Ser Leu Ser Ala Val Ser Thr Ser Ser Glu Tyr
    450                 455                 460

Met Gly Gly Ser Ala Ala Ile Gly Pro Ile Thr Pro Ala Thr Thr Ser
465                 470                 475                 480

Ser Ile Thr Ala Ala Val Thr Ala Ser Ser Thr Thr Ser Ala Val Pro
                485                 490                 495

Met Gly Asn Gly Val Gly Val Gly Val Gly Val Gly Gly Asn Val Ser
                500                 505                 510

Met Tyr Ala Asn Ala Gln Thr Ala Met Ala Leu Met Gly Val Ala Leu
            515                 520                 525

His Ser His Gln Glu Gln Leu Ile Gly Gly Val Ala Val Lys Ser Glu
    530                 535                 540

His Ser Thr Thr Ala
545

<210> SEQ ID NO 19
<211> LENGTH: 445
<212> TYPE: PRT
<213> ORGANISM: Drosophila melanogaster
<220> FEATURE:
<221> NAME/KEY: misc_feature
<223> OTHER INFORMATION: Novel Sequence

<400> SEQUENCE: 19

Tyr Glu Gln Pro Ser Glu Glu Asp Leu Arg Arg Ile Met Ser Gln Pro
1               5                   10                  15

Asp Glu Asn Glu Ser Gln Thr Asp Val Ser Phe Arg His Ile Thr Glu
            20                  25                  30

Ile Thr Ile Leu Thr Val Gln Leu Ile Val Glu Phe Ala Lys Gly Leu
        35                  40                  45

Pro Ala Phe Thr Lys Ile Pro Gln Glu Asp Gln Ile Thr Leu Leu Lys
    50                  55                  60

Ala Cys Ser Ser Glu Val Met Met Leu Arg Met Ala Arg Arg Tyr Asp
65                  70                  75                  80

His Ser Ser Asp Ser Ile Phe Phe Ala Asn Asn Arg Ser Tyr Thr Arg
                85                  90                  95

Asp Ser Tyr Lys Met Ala Gly Met Ala Asp Asn Ile Glu Asp Leu Leu
            100                 105                 110

His Phe Cys Arg Gln Met Phe Ser Met Lys Val Asp Asn Val Glu Tyr
        115                 120                 125

Ala Leu Leu Thr Ala Ile Val Ile Phe Ser Asp Arg Pro Gly Leu Glu
    130                 135                 140

Lys Ala Gln Leu Val Glu Ala Ile Gln Ser Tyr Tyr Ile Asp Thr Leu
145                 150                 155                 160

Arg Ile Tyr Ile Leu Asn Arg His Cys Gly Asp Ser Met Ser Leu Val
                165                 170                 175

Phe Tyr Ala Lys Leu Leu Ser Ile Leu Thr Glu Leu Arg Thr Leu Gly
            180                 185                 190

Asn Gln Asn Ala Glu Met Cys Phe Ser Leu Lys Leu Lys Asn Arg Lys
        195                 200                 205

Leu Pro Lys Phe Leu Glu Glu Ile Trp Asp Val His Ala Ile Pro Pro
    210                 215                 220

Ser Val Gln Ser His Leu Gln Ile Thr Gln Glu Glu Asn Glu Arg Leu
225                 230                 235                 240
```

```
Glu Arg Ala Glu Arg Met Arg Ala Ser Val Gly Gly Ala Ile Thr Ala
                245                 250                 255

Gly Ile Asp Cys Asp Ser Ala Ser Thr Ser Ala Ala Ala Ala Ala Ala
            260                 265                 270

Gln His Gln Pro Gln Pro Gln Pro Gln Pro Gln Pro Ser Ser Leu Thr
        275                 280                 285

Gln Asn Asp Ser Gln His Gln Thr Gln Pro Gln Leu Gln Pro Gln Leu
    290                 295                 300

Pro Pro Gln Leu Gln Gly Gln Leu Gln Pro Gln Leu Gln Pro Gln Leu
305                 310                 315                 320

Gln Thr Gln Leu Gln Pro Gln Ile Gln Pro Gln Pro Gln Leu Leu Pro
                325                 330                 335

Val Ser Ala Pro Val Pro Ala Ser Val Thr Ala Pro Gly Ser Leu Ser
            340                 345                 350

Ala Val Ser Thr Ser Ser Glu Tyr Met Gly Gly Ser Ala Ala Ile Gly
        355                 360                 365

Pro Ile Thr Pro Ala Thr Thr Ser Ser Ile Thr Ala Ala Val Thr Ala
    370                 375                 380

Ser Ser Thr Thr Ser Ala Val Pro Met Gly Asn Gly Val Gly Val Gly
385                 390                 395                 400

Val Gly Val Gly Gly Asn Val Ser Met Tyr Ala Asn Ala Gln Thr Ala
                405                 410                 415

Met Ala Leu Met Gly Val Ala Leu His Ser His Gln Glu Gln Leu Ile
            420                 425                 430

Gly Gly Val Ala Val Lys Ser Glu His Ser Thr Thr Ala
        435                 440                 445

<210> SEQ ID NO 20
<211> LENGTH: 323
<212> TYPE: PRT
<213> ORGANISM: Drosophila melanogaster
<220> FEATURE:
<221> NAME/KEY: misc_feature
<223> OTHER INFORMATION: Novel Sequence

<400> SEQUENCE: 20

Arg Pro Glu Cys Val Val Pro Glu Asn Gln Cys Ala Met Lys Arg Arg
1               5                   10                  15

Glu Lys Lys Ala Gln Lys Glu Lys Asp Lys Met Thr Thr Ser Pro Ser
            20                  25                  30

Ser Gln His Gly Gly Asn Gly Ser Leu Ala Ser Gly Gly Gly Gln Asp
        35                  40                  45

Phe Val Lys Lys Glu Ile Leu Asp Leu Met Thr Cys Glu Pro Pro Gln
    50                  55                  60

His Ala Thr Ile Pro Leu Leu Pro Asp Glu Ile Leu Ala Lys Cys Gln
65                  70                  75                  80

Ala Arg Asn Ile Pro Ser Leu Thr Tyr Asn Gln Leu Ala Val Ile Tyr
                85                  90                  95

Lys Leu Ile Trp Tyr Gln Asp Gly Tyr Glu Gln Pro Ser Glu Glu Asp
            100                 105                 110

Leu Arg Arg Ile Met Ser Gln Pro Asp Glu Asn Glu Ser Gln Thr Asp
        115                 120                 125

Val Ser Phe Arg His Ile Thr Glu Ile Thr Ile Leu Thr Val Gln Leu
    130                 135                 140

Ile Val Glu Phe Ala Lys Gly Leu Pro Ala Phe Thr Lys Ile Pro Gln
```

```
                145                 150                 155                 160
Glu Asp Gln Ile Thr Leu Leu Lys Ala Cys Ser Ser Glu Val Met Met
                    165                 170                 175

Leu Arg Met Ala Arg Arg Tyr Asp His Ser Ser Asp Ser Ile Phe Phe
            180                 185                 190

Ala Asn Asn Arg Ser Tyr Thr Arg Asp Ser Tyr Lys Met Ala Gly Met
                195                 200                 205

Ala Asp Asn Ile Glu Asp Leu Leu His Phe Cys Arg Gln Met Phe Ser
        210                 215                 220

Met Lys Val Asp Asn Val Glu Tyr Ala Leu Leu Thr Ala Ile Val Ile
225                 230                 235                 240

Phe Ser Asp Arg Pro Gly Leu Glu Lys Ala Gln Leu Val Glu Ala Ile
                245                 250                 255

Gln Ser Tyr Tyr Ile Asp Thr Leu Arg Ile Tyr Ile Leu Asn Arg His
            260                 265                 270

Cys Gly Asp Ser Met Ser Leu Val Phe Tyr Ala Lys Leu Leu Ser Ile
        275                 280                 285

Leu Thr Glu Leu Arg Thr Leu Gly Asn Gln Asn Ala Glu Met Cys Phe
    290                 295                 300

Ser Leu Lys Leu Lys Asn Arg Lys Leu Pro Lys Phe Leu Glu Glu Ile
305                 310                 315                 320

Trp Asp Val
```

<210> SEQ ID NO 21
<211> LENGTH: 987
<212> TYPE: DNA
<213> ORGANISM: Mus musculus
<220> FEATURE:
<221> NAME/KEY: misc_feature
<223> OTHER INFORMATION: Novel Sequence

<400> SEQUENCE: 21

```
tgtgctatct gtggggaccg ctcctcaggc aaacactatg gggtatacag ttgtgagggc      60
tgcaagggct tcttcaagag gacagtacgc aaagacctga cctacacctg ccagacaac      120
aaggactgcc tgatcgacaa gagacagcgg aaccggtgtc agtactgccg ctaccagaag     180
tgcctggcca tggcatgaa gcgggaagct gtgcaggagg agcggcagcg gggcaaggac      240
cggaatgaga acgaggtgga gtccaccagc agtgccaacg aggacatgcc tgtagagaag     300
attctggaag ccgagcttgc tgtcgagccc aagactgaga catacgtgga ggcaaacatg     360
gggctgaacc ccagctcacc aaatgaccct gttaccaaca tctgtcaagc agcagacaag     420
cagctcttca ctcttgtgga gtgggccaag aggatcccac acttttctga gctgcccta      480
gacgaccagg tcatcctgct acgggcaggc tggaacgagc tgctgatcgc ctccttctcc     540
caccgctcca tagctgtgaa agatgggatt ctcctggcca ccggcctgca cgtacaccgg     600
aacagcgctc acagtgctgg ggtgggcgcc atctttgaca gggtgctaac agagctggtg     660
tctaagatgc gtgacatgca gatggacaag acggagctgg gctgcctgcg agccattgtc     720
ctgttcaacc ctgactctaa ggggctctca accctgctg aggtggaggc gttgagggag      780
aaggtgtatg cgtcactaga agcgtactgc aaacacaagt accctgagca gccgggcagg     840
tttgccaagc tgctgctccg cctgcctgca ctgcgttcca tcgggctcaa gtgcctggag     900
cacctgttct tcttcaagct catcggggac acgcccatcg acaccttcct catggagatg     960
ctggaggcac acatcaagc caacctag                                          987
```

<210> SEQ ID NO 22
<211> LENGTH: 789
<212> TYPE: DNA
<213> ORGANISM: Mus musculus
<220> FEATURE:
<221> NAME/KEY: misc_feature
<223> OTHER INFORMATION: Novel Sequence

<400> SEQUENCE: 22

| | | | | | |
|---|---|---|---|---|---|
| aagcgggaag | ctgtgcagga | ggagcggcag | cggggcaagg | accggaatga | gaacgaggtg | 60 |
| gagtccacca | gcagtgccaa | cgaggacatg | cctgtagaga | agattctgga | agccgagctt | 120 |
| gctgtcgagc | ccaagactga | gacatacgtg | gaggcaaaca | tggggctgaa | ccccagctca | 180 |
| ccaaatgacc | ctgttaccaa | catctgtcaa | gcagcagaca | agcagctctt | cactcttgtg | 240 |
| gagtgggcca | agaggatccc | acactttttct | gagctgcccc | tagacgacca | ggtcatcctg | 300 |
| ctacgggcag | ctggaacga | gctgctgatc | gcctccttct | cccaccgctc | catagctgtg | 360 |
| aaagatggga | ttctcctggc | caccggcctg | cacgtacacc | ggaacagcgc | tcacagtgct | 420 |
| ggggtgggcg | ccatctttga | cagggtgcta | acagagctgg | tgtctaagat | gcgtgacatg | 480 |
| cagatggaca | agacggagct | gggctgcctg | cgagccattg | tcctgttcaa | ccctgactct | 540 |
| aagggctct | caaaccctgc | tgaggtggag | gcgttgaggg | agaaggtgta | tgcgtcacta | 600 |
| gaagcgtact | gcaaacacaa | gtaccctgag | cagccgggca | ggtttgccaa | gctgctgctc | 660 |
| cgcctgcctg | cactgcgttc | catcgggctc | aagtgcctgg | agcacctgtt | cttcttcaag | 720 |
| ctcatcgggg | acacgcccat | cgacaccttc | ctcatggaga | tgctggaggc | accacatcaa | 780 |
| gccacctag | | | | | | 789 |

<210> SEQ ID NO 23
<211> LENGTH: 714
<212> TYPE: DNA
<213> ORGANISM: Mus musculus
<220> FEATURE:
<221> NAME/KEY: misc_feature
<223> OTHER INFORMATION: Novel Sequence

<400> SEQUENCE: 23

| | | | | | |
|---|---|---|---|---|---|
| gccaacgagg | acatgcctgt | agagaagatt | ctggaagccg | agcttgctgt | cgagcccaag | 60 |
| actgagacat | acgtggaggc | aaacatgggg | ctgaacccca | gctcaccaaa | tgaccctgtt | 120 |
| accaacatct | gtcaagcagc | agacaagcag | ctcttcactc | ttgtggagtg | ggccaagagg | 180 |
| atcccacact | tttctgagct | gcccctagac | gaccaggtca | tcctgctacg | ggcaggctgg | 240 |
| aacgagctgc | tgatcgcctc | cttctcccac | cgctccatag | ctgtgaaaga | tgggattctc | 300 |
| ctggccaccg | gcctgcacgt | acaccggaac | agcgctcaca | gtgctgggt | gggcgccatc | 360 |
| tttgacaggg | tgctaacaga | gctggtgtct | aagatgcgtg | acatgcagat | ggacaagacg | 420 |
| gagctgggct | gcctgcgagc | cattgtcctg | ttcaaccctg | actctaaggg | gctctcaaac | 480 |
| cctgctgagg | tggaggcgtt | gagggagaag | gtgtatgcgt | cactagaagc | gtactgcaaa | 540 |
| cacaagtacc | ctgagcagcc | gggcaggttt | gccaagctgc | tgctccgcct | gcctgcactg | 600 |
| cgttccatcg | ggctcaagtg | cctggagcac | ctgttcttct | tcaagctcat | cggggacacg | 660 |
| cccatcgaca | ccttcctcat | ggagatgctg | gaggcaccac | atcaagccac | ctag | 714 |

<210> SEQ ID NO 24
<211> LENGTH: 536
<212> TYPE: DNA
<213> ORGANISM: Mus musculus
<220> FEATURE:
<221> NAME/KEY: misc_feature
<223> OTHER INFORMATION: Novel Sequence

<400> SEQUENCE: 24

| | | | | | |
|---|---|---|---|---|---|
| ggatcccaca | cttttctgag | ctgcccctag | acgaccaggt | catcctgcta | cgggcaggct | 60 |
| ggaacgagct | gctgatcgcc | tccttctccc | accgctccat | agctgtgaaa | gatgggattc | 120 |
| tcctggccac | cggcctgcac | gtacaccgga | acagcgctca | cagtgctggg | gtgggcgcca | 180 |
| tctttgacag | ggtgctaaca | gagctggtgt | ctaagatgcg | tgacatgcag | atggacaaga | 240 |
| cggagctggg | ctgcctgcga | gccattgtcc | tgttcaaccc | tgactctaag | ggctctcaa | 300 |
| accctgctga | ggtggaggcg | ttgagggaga | aggtgtatgc | gtcactagaa | gcgtactgca | 360 |
| aacacaagta | ccctgagcag | ccgggcaggt | ttgccaagct | gctgctccgc | ctgcctgcac | 420 |
| tgcgttccat | cgggctcaag | tgcctggagc | acctgttctt | cttcaagctc | atcggggaca | 480 |
| cgcccatcga | caccttcctc | atggagatgc | tggaggcacc | acatcaagcc | acctag | 536 |

<210> SEQ ID NO 25
<211> LENGTH: 672
<212> TYPE: DNA
<213> ORGANISM: Mus musculus
<220> FEATURE:
<221> NAME/KEY: misc_feature
<223> OTHER INFORMATION: Novel Sequence

<400> SEQUENCE: 25

| | | | | | |
|---|---|---|---|---|---|
| gccaacgagg | acatgcctgt | agagaagatt | ctggaagccg | agcttgctgt | cgagcccaag | 60 |
| actgagacat | acgtggaggc | aaacatgggg | ctgaacccca | gctcaccaaa | tgaccctgtt | 120 |
| accaacatct | gtcaagcagc | agacaagcag | ctcttcactc | ttgtggagtg | ggccaagagg | 180 |
| atcccacact | tttctgagct | gcccctagac | gaccaggtca | tcctgctacg | ggcaggctgg | 240 |
| aacgagctgc | tgatcgcctc | cttctcccac | cgctccatag | ctgtgaaaga | tgggattctc | 300 |
| ctggccaccg | gcctgcacgt | acaccggaac | agcgctcaca | gtgctggggt | gggcgccatc | 360 |
| tttgacaggg | tgctaacaga | gctggtgtct | aagatgcgtg | acatgcagat | ggacaagacg | 420 |
| gagctgggct | gcctgcgagc | cattgtcctg | ttcaaccctg | actctaaggg | ctctcaaac | 480 |
| cctgctgagg | tggaggcgtt | gagggagaag | gtgtatgcgt | cactagaagc | gtactgcaaa | 540 |
| cacaagtacc | ctgagcagcc | gggcaggttt | gccaagctgc | tgctccgcct | gcctgcactg | 600 |
| cgttccatcg | ggctcaagtg | cctggagcac | ctgttcttct | tcaagctcat | cggggacacg | 660 |
| cccatcgaca | cc | | | | | 672 |

<210> SEQ ID NO 26
<211> LENGTH: 1123
<212> TYPE: DNA
<213> ORGANISM: Homo sapiens
<220> FEATURE:
<221> NAME/KEY: misc_feature
<223> OTHER INFORMATION: Novel Sequence

<400> SEQUENCE: 26

| | | | | | |
|---|---|---|---|---|---|
| tgcgccatct | gcggggaccg | ctcctcaggc | aagcactatg | gagtgtacag | ctgcgagggg | 60 |
| tgcaagggct | tcttcaagcg | gacggtgcgc | aaggacctga | cctacacctg | ccgcgacaac | 120 |
| aaggactgcc | tgattgacaa | gcggcagcgg | aaccggtgcc | agtactgccg | ctaccagaag | 180 |
| tgcctggcca | tgggcatgaa | gcgggaagcc | gtgcaggagg | agcggcagcg | tggcaaggac | 240 |
| cggaacgaga | atgaggtgga | gtcgaccagc | agcgccaacg | aggacatgcc | ggtggagagg | 300 |

```
atcctggagg ctgagctggc cgtggagccc aagaccgaga cctacgtgga ggcaaacatg    360
gggctgaacc ccagctcgcc gaacgaccct gtcaccaaca tttgccaagc agccgacaaa    420
cagcttttca ccctggtgga gtgggccaag cggatcccac acttctcaga gctgcccctg    480
gacgaccagg tcatcctgct gcgggcaggc tggaatgagc tgctcatcgc ctccttctcc    540
caccgctcca tcgccgtgaa ggacgggatc tccctggcca ccgggctgca cgtccaccgg    600
aacagcgccc acagcgcagg ggtgggcgcc atctttgaca gggtgctgac ggagcttgtg    660
tccaagatgc gggacatgca gatggacaag acggagctgg gctgcctgcg cgccatcgtc    720
ctctttaacc ctgactccaa ggggctctcg aacccggccg aggtggaggc gctgagggag    780
aaggtctatg cgtccttgga ggcctactgc aagcacaagt acccagagca gccgggaagg    840
ttcgctaagc tcttgctccg cctgccggct ctgcgctcca tcgggctcaa atgcctggaa    900
catctcttct tcttcaagct catcgggac acacccattg acaccttcct tatggagatg    960
ctggaggcgc cgcaccaaat gacttaggcc tgcgggccca tcctttgtgc ccacccgttc   1020
tggccaccct gcctggacgc cagctgttct tctcagcctg agccctgtcc ctgcccttct   1080
ctgcctggcc tgtttggact ttggggcaca gcctgtcact gct                    1123

<210> SEQ ID NO 27
<211> LENGTH: 925
<212> TYPE: DNA
<213> ORGANISM: Homo sapiens
<220> FEATURE:
<221> NAME/KEY: misc_feature
<223> OTHER INFORMATION: Novel Sequence

<400> SEQUENCE: 27
aagcgggaag ccgtgcagga ggagcggcag cgtggcaagg accggaacga gaatgaggtg     60
gagtcgacca gcagcgccaa cgaggacatg ccggtggaga ggatcctgga ggctgagctg    120
gccgtggagc ccaagaccga gacctacgtg gaggcaaaca tggggctgaa ccccagctcg    180
ccgaacgacc ctgtcaccaa catttgccaa gcagccgaca acagcttttt caccctggtg    240
gagtgggcca agcggatccc acacttctca gagctgcccc tggacgacca ggtcatcctg    300
ctgcgggcag gctggaatga gctgctcatc gcctccttct cccaccgctc catcgccgtg    360
aaggacggga tcctcctggc caccgggctg cacgtccacc ggaacagcgc ccacagcgca    420
ggggtgggcg ccatctttga cagggtgctg acggagcttg tgtccaagat gcgggacatg    480
cagatggaca agacggagct gggctgcctg cgcgccatcg tcctctttaa ccctgactcc    540
aaggggctct cgaacccggc cgaggtggag gcgctgaggg agaaggtcta tgcgtccttg    600
gaggcctact gcaagcacaa gtacccagag cagccgggaa ggttcgctaa gctcttgctc    660
cgcctgccgg ctctgcgctc catcgggctc aaatgcctgg aacatctctt cttcttcaag    720
ctcatcgggg acacacccat tgacaccttc cttatggaga tgctggaggc gccgcaccaa    780
atgacttagg cctgcgggcc catcctttgt gcccacccgt tctggccacc ctgcctggac    840
gccagctgtt cttctcagcc tgagcccgtg cctgccctt ctctgcctgg cctgtttgga    900
ctttggggca gcctgtca ctgct                                            925

<210> SEQ ID NO 28
<211> LENGTH: 850
<212> TYPE: DNA
<213> ORGANISM: Homo sapiens
<220> FEATURE:
<221> NAME/KEY: misc_feature
```

<223> OTHER INFORMATION: Novel Sequence

<400> SEQUENCE: 28

| gccaacgagg | acatgccggt | ggagaggatc | ctggaggctg | agctggccgt | ggagcccaag | 60 |
| accgagacct | acgtggaggc | aaacatgggg | ctgaacccca | gctcgccgaa | cgaccctgtc | 120 |
| accaacattt | gccaagcagc | cgacaaacag | cttttcaccc | tggtggagtg | ggccaagcgg | 180 |
| atcccacact | tctcagagct | gcccctggac | gaccaggtca | tcctgctgcg | ggcaggctgg | 240 |
| aatgagctgc | tcatcgcctc | cttctcccac | cgctccatcg | ccgtgaagga | cgggatcctc | 300 |
| ctggccaccg | ggctgcacgt | ccaccggaac | agcgcccaca | gcgcaggggt | gggcgccatc | 360 |
| tttgacaggg | tgctgacgga | gcttgtgtcc | aagatgcggg | acatgcagat | ggacaagacg | 420 |
| gagctgggct | gcctgcgcgc | catcgtcctc | tttaaccctg | actccaaggg | gctctcgaac | 480 |
| ccggccgagg | tggaggcgct | gagggagaag | gtctatgcgt | ccttggaggc | ctactgcaag | 540 |
| cacaagtacc | cagagcagcc | gggaaggttc | gctaagctct | tgctccgcct | gccggctctg | 600 |
| cgctccatcg | ggctcaaatg | cctggaacat | ctcttcttct | tcaagctcat | cggggacaca | 660 |
| cccattgaca | ccttccttat | ggagatgctg | gaggcgccgc | accaaatgac | ttaggcctgc | 720 |
| gggcccatcc | tttgtgccca | cccgttctgg | ccaccctgcc | tggacgccag | ctgttcttct | 780 |
| cagcctgagc | cctgtccctg | cccttctctg | cctggcctgt | ttggactttg | gggcacagcc | 840 |
| tgtcactgct | | | | | | 850 |

<210> SEQ ID NO 29
<211> LENGTH: 670
<212> TYPE: DNA
<213> ORGANISM: Homo sapiens
<220> FEATURE:
<221> NAME/KEY: misc_feature
<223> OTHER INFORMATION: Novel Sequence

<400> SEQUENCE: 29

| atcccacact | tctcagagct | gcccctggac | gaccaggtca | tcctgctgcg | ggcaggctgg | 60 |
| aatgagctgc | tcatcgcctc | cttctcccac | cgctccatcg | ccgtgaagga | cgggatcctc | 120 |
| ctggccaccg | ggctgcacgt | ccaccggaac | agcgcccaca | gcgcaggggt | gggcgccatc | 180 |
| tttgacaggg | tgctgacgga | gcttgtgtcc | aagatgcggg | acatgcagat | ggacaagacg | 240 |
| gagctgggct | gcctgcgcgc | catcgtcctc | tttaaccctg | actccaaggg | gctctcgaac | 300 |
| ccggccgagg | tggaggcgct | gagggagaag | gtctatgcgt | ccttggaggc | ctactgcaag | 360 |
| cacaagtacc | cagagcagcc | gggaaggttc | gctaagctct | tgctccgcct | gccggctctg | 420 |
| cgctccatcg | ggctcaaatg | cctggaacat | ctcttcttct | tcaagctcat | cggggacaca | 480 |
| cccattgaca | ccttccttat | ggagatgctg | gaggcgccgc | accaaatgac | ttaggcctgc | 540 |
| gggcccatcc | tttgtgccca | cccgttctgg | ccaccctgcc | tggacgccag | ctgttcttct | 600 |
| cagcctgagc | cctgtccctg | cccttctctg | cctggcctgt | ttggactttg | gggcacagcc | 660 |
| tgtcactgct | | | | | | 670 |

<210> SEQ ID NO 30
<211> LENGTH: 672
<212> TYPE: DNA
<213> ORGANISM: Homo sapiens
<220> FEATURE:
<221> NAME/KEY: misc_feature
<223> OTHER INFORMATION: Novel Sequence

<400> SEQUENCE: 30

```
gccaacgagg acatgccggt ggagaggatc ctggaggctg agctggccgt ggagcccaag    60
accgagacct acgtggaggc aaacatgggg ctgaacccca gctcgccgaa cgaccctgtc   120
accaacattt gccaagcagc cgacaaacag cttttcaccc tggtggagtg ggccaagcgg   180
atcccacact tctcagagct gcccctggac gaccaggtca tcctgctgcg ggcaggctgg   240
aatgagctgc tcatcgcctc cttctcccac cgctccatcg ccgtgaagga cgggatcctc   300
ctggccaccg ggctgcacgt ccaccggaac agcgcccaca gcgcaggggt gggcgccatc   360
tttgacaggg tgctgacgga gcttgtgtcc aagatgcggg acatgcagat ggacaagacg   420
gagctgggct gcctgcgcgc catcgtcctc tttaaccctg actccaaggg gctctcgaac   480
ccggccgagg tggaggcgct gagggagaag gtctatgcgt ccttggaggc ctactgcaag   540
cacaagtacc agagcagcc gggaaggttc gctaagctct tgctccgcct gccggctctg   600
cgctccatcg ggctcaaatg cctggaacat ctcttcttct tcaagctcat cggggacaca   660
cccattgaca cc                                                      672
```

<210> SEQ ID NO 31
<211> LENGTH: 328
<212> TYPE: PRT
<213> ORGANISM: Mus musculus
<220> FEATURE:
<221> NAME/KEY: misc_feature
<223> OTHER INFORMATION: Novel Sequence

<400> SEQUENCE: 31

```
Cys Ala Ile Cys Gly Asp Arg Ser Ser Gly Lys His Tyr Gly Val Tyr
1               5                   10                  15

Ser Cys Glu Gly Cys Lys Gly Phe Phe Lys Arg Thr Val Arg Lys Asp
            20                  25                  30

Leu Thr Tyr Thr Cys Arg Asp Asn Lys Asp Cys Leu Ile Asp Lys Arg
        35                  40                  45

Gln Arg Asn Arg Cys Gln Tyr Cys Arg Tyr Gln Lys Cys Leu Ala Met
    50                  55                  60

Gly Met Lys Arg Glu Ala Val Gln Glu Glu Arg Gln Arg Gly Lys Asp
65                  70                  75                  80

Arg Asn Glu Asn Glu Val Glu Ser Thr Ser Ser Ala Asn Glu Asp Met
                85                  90                  95

Pro Val Glu Lys Ile Leu Glu Ala Glu Leu Ala Val Glu Pro Lys Thr
            100                 105                 110

Glu Thr Tyr Val Glu Ala Asn Met Gly Leu Asn Pro Ser Ser Pro Asn
        115                 120                 125

Asp Pro Val Thr Asn Ile Cys Gln Ala Ala Asp Lys Gln Leu Phe Thr
    130                 135                 140

Leu Val Glu Trp Ala Lys Arg Ile Pro His Phe Ser Glu Leu Pro Leu
145                 150                 155                 160

Asp Asp Gln Val Ile Leu Leu Arg Ala Gly Trp Asn Glu Leu Leu Ile
                165                 170                 175

Ala Ser Phe Ser His Arg Ser Ile Ala Val Lys Asp Gly Ile Leu Leu
            180                 185                 190

Ala Thr Gly Leu His Val His Arg Asn Ser Ala His Ser Ala Gly Val
        195                 200                 205

Gly Ala Ile Phe Asp Arg Val Leu Thr Glu Leu Val Ser Lys Met Arg
    210                 215                 220

Asp Met Gln Met Asp Lys Thr Glu Leu Gly Cys Leu Arg Ala Ile Val
```

-continued

```
            225                 230                 235                 240
Leu Phe Asn Pro Asp Ser Lys Gly Leu Ser Asn Pro Ala Glu Val Glu
                245                 250                 255
Ala Leu Arg Glu Lys Val Tyr Ala Ser Leu Glu Ala Tyr Cys Lys His
            260                 265                 270
Lys Tyr Pro Glu Gln Pro Gly Arg Phe Ala Lys Leu Leu Arg Leu
            275                 280                 285
Pro Ala Leu Arg Ser Ile Gly Leu Lys Cys Leu Glu His Leu Phe Phe
            290                 295                 300
Phe Lys Leu Ile Gly Asp Thr Pro Ile Asp Thr Phe Leu Met Glu Met
305                 310                 315                 320
Leu Glu Ala Pro His Gln Ala Thr
                325
```

<210> SEQ ID NO 32
<211> LENGTH: 262
<212> TYPE: PRT
<213> ORGANISM: Mus musculus
<220> FEATURE:
<221> NAME/KEY: misc_feature
<223> OTHER INFORMATION: Novel Sequence

<400> SEQUENCE: 32

```
Lys Arg Glu Ala Val Gln Glu Arg Gln Arg Gly Lys Asp Arg Asn
1               5                   10                  15
Glu Asn Glu Val Glu Ser Thr Ser Ser Ala Asn Glu Asp Met Pro Val
            20                  25                  30
Glu Lys Ile Leu Glu Ala Glu Leu Ala Val Glu Pro Lys Thr Glu Thr
            35                  40                  45
Tyr Val Glu Ala Asn Met Gly Leu Asn Pro Ser Ser Pro Asn Asp Pro
            50                  55                  60
Val Thr Asn Ile Cys Gln Ala Ala Asp Lys Gln Leu Phe Thr Leu Val
65                  70                  75                  80
Glu Trp Ala Lys Arg Ile Pro His Phe Ser Glu Leu Pro Leu Asp Asp
                85                  90                  95
Gln Val Ile Leu Leu Arg Ala Gly Trp Asn Glu Leu Leu Ile Ala Ser
            100                 105                 110
Phe Ser His Arg Ser Ile Ala Val Lys Asp Gly Ile Leu Leu Ala Thr
            115                 120                 125
Gly Leu His Val His Arg Asn Ser Ala His Ser Ala Gly Val Gly Ala
            130                 135                 140
Ile Phe Asp Arg Val Leu Thr Glu Leu Val Ser Lys Met Arg Asp Met
145                 150                 155                 160
Gln Met Asp Lys Thr Glu Leu Gly Cys Leu Arg Ala Ile Val Leu Phe
                165                 170                 175
Asn Pro Asp Ser Lys Gly Leu Ser Asn Pro Ala Glu Val Glu Ala Leu
            180                 185                 190
Arg Glu Lys Val Tyr Ala Ser Leu Glu Ala Tyr Cys Lys His Lys Tyr
            195                 200                 205
Pro Glu Gln Pro Gly Arg Phe Ala Lys Leu Leu Leu Arg Leu Pro Ala
            210                 215                 220
Leu Arg Ser Ile Gly Leu Lys Cys Leu Glu His Leu Phe Phe Phe Lys
225                 230                 235                 240
Leu Ile Gly Asp Thr Pro Ile Asp Thr Phe Leu Met Glu Met Leu Glu
                245                 250                 255
```

```
Ala Pro His Gln Ala Thr
            260
```

```
<210> SEQ ID NO 33
<211> LENGTH: 237
<212> TYPE: PRT
<213> ORGANISM: Mus musculus
<220> FEATURE:
<221> NAME/KEY: misc_feature
<223> OTHER INFORMATION: Novel Sequence

<400> SEQUENCE: 33
```

```
Ala Asn Glu Asp Met Pro Val Glu Lys Ile Leu Glu Ala Glu Leu Ala
1               5                   10                  15

Val Glu Pro Lys Thr Glu Thr Tyr Val Glu Ala Asn Met Gly Leu Asn
            20                  25                  30

Pro Ser Ser Pro Asn Asp Pro Val Thr Asn Ile Cys Gln Ala Ala Asp
        35                  40                  45

Lys Gln Leu Phe Thr Leu Val Glu Trp Ala Lys Arg Ile Pro His Phe
    50                  55                  60

Ser Glu Leu Pro Leu Asp Asp Gln Val Ile Leu Leu Arg Ala Gly Trp
65                  70                  75                  80

Asn Glu Leu Leu Ile Ala Ser Phe Ser His Arg Ser Ile Ala Val Lys
                85                  90                  95

Asp Gly Ile Leu Leu Ala Thr Gly Leu His Val His Arg Asn Ser Ala
            100                 105                 110

His Ser Ala Gly Val Gly Ala Ile Phe Asp Arg Val Leu Thr Glu Leu
        115                 120                 125

Val Ser Lys Met Arg Asp Met Gln Met Asp Lys Thr Glu Leu Gly Cys
    130                 135                 140

Leu Arg Ala Ile Val Leu Phe Asn Pro Asp Ser Lys Gly Leu Ser Asn
145                 150                 155                 160

Pro Ala Glu Val Glu Ala Leu Arg Glu Lys Val Tyr Ala Ser Leu Glu
                165                 170                 175

Ala Tyr Cys Lys His Lys Tyr Pro Glu Gln Pro Gly Arg Phe Ala Lys
            180                 185                 190

Leu Leu Leu Arg Leu Pro Ala Leu Arg Ser Ile Gly Leu Lys Cys Leu
        195                 200                 205

Glu His Leu Phe Phe Phe Lys Leu Ile Gly Asp Thr Pro Ile Asp Thr
    210                 215                 220

Phe Leu Met Glu Met Leu Glu Ala Pro His Gln Ala Thr
225                 230                 235
```

```
<210> SEQ ID NO 34
<211> LENGTH: 177
<212> TYPE: PRT
<213> ORGANISM: Mus musculus
<220> FEATURE:
<221> NAME/KEY: misc_feature
<223> OTHER INFORMATION: Novel Sequence

<400> SEQUENCE: 34
```

```
Ile Pro His Phe Ser Glu Leu Pro Leu Asp Asp Gln Val Ile Leu Leu
1               5                   10                  15

Arg Ala Gly Trp Asn Glu Leu Leu Ile Ala Ser Phe Ser His Arg Ser
            20                  25                  30

Ile Ala Val Lys Asp Gly Ile Leu Leu Ala Thr Gly Leu His Val His
        35                  40                  45
```

```
Arg Asn Ser Ala His Ser Ala Gly Val Gly Ala Ile Phe Asp Arg Val
    50                  55                  60

Leu Thr Glu Leu Val Ser Lys Met Arg Asp Met Gln Met Asp Lys Thr
65                  70                  75                  80

Glu Leu Gly Cys Leu Arg Ala Ile Val Leu Phe Asn Pro Asp Ser Lys
                85                  90                  95

Gly Leu Ser Asn Pro Ala Glu Val Glu Ala Leu Arg Glu Lys Val Tyr
                100                 105                 110

Ala Ser Leu Glu Ala Tyr Cys Lys His Lys Tyr Pro Glu Gln Pro Gly
                115                 120                 125

Arg Phe Ala Lys Leu Leu Leu Arg Leu Pro Ala Leu Arg Ser Ile Gly
    130                 135                 140

Leu Lys Cys Leu Glu His Leu Phe Phe Phe Lys Leu Ile Gly Asp Thr
145                 150                 155                 160

Pro Ile Asp Thr Phe Leu Met Glu Met Leu Glu Ala Pro His Gln Ala
                165                 170                 175

Thr
```

<210> SEQ ID NO 35
<211> LENGTH: 224
<212> TYPE: PRT
<213> ORGANISM: Mus musculus
<220> FEATURE:
<221> NAME/KEY: misc_feature
<223> OTHER INFORMATION: Novel Sequence

<400> SEQUENCE: 35

```
Ala Asn Glu Asp Met Pro Val Glu Lys Ile Leu Glu Ala Glu Leu Ala
1               5                   10                  15

Val Glu Pro Lys Thr Glu Thr Tyr Val Glu Ala Asn Met Gly Leu Asn
                20                  25                  30

Pro Ser Ser Pro Asn Asp Pro Val Thr Asn Ile Cys Gln Ala Ala Asp
                35                  40                  45

Lys Gln Leu Phe Thr Leu Val Glu Trp Ala Lys Arg Ile Pro His Phe
    50                  55                  60

Ser Glu Leu Pro Leu Asp Asp Gln Val Ile Leu Leu Arg Ala Gly Trp
65                  70                  75                  80

Asn Glu Leu Leu Ile Ala Ser Phe Ser His Arg Ser Ile Ala Val Lys
                85                  90                  95

Asp Gly Ile Leu Leu Ala Thr Gly Leu His Val His Arg Asn Ser Ala
                100                 105                 110

His Ser Ala Gly Val Gly Ala Ile Phe Asp Arg Val Leu Thr Glu Leu
                115                 120                 125

Val Ser Lys Met Arg Asp Met Gln Met Asp Lys Thr Glu Leu Gly Cys
    130                 135                 140

Leu Arg Ala Ile Val Leu Phe Asn Pro Asp Ser Lys Gly Leu Ser Asn
145                 150                 155                 160

Pro Ala Glu Val Glu Ala Leu Arg Glu Lys Val Tyr Ala Ser Leu Glu
                165                 170                 175

Ala Tyr Cys Lys His Lys Tyr Pro Glu Gln Pro Gly Arg Phe Ala Lys
                180                 185                 190

Leu Leu Leu Arg Leu Pro Ala Leu Arg Ser Ile Gly Leu Lys Cys Leu
    195                 200                 205

Glu His Leu Phe Phe Phe Lys Leu Ile Gly Asp Thr Pro Ile Asp Thr
210                 215                 220
```

-continued

```
<210> SEQ ID NO 36
<211> LENGTH: 328
<212> TYPE: PRT
<213> ORGANISM: Homo sapiens
<220> FEATURE:
<221> NAME/KEY: misc_feature
<223> OTHER INFORMATION: Novel Sequence

<400> SEQUENCE: 36

Cys Ala Ile Cys Gly Asp Arg Ser Ser Gly Lys His Tyr Gly Val Tyr
 1               5                  10                  15

Ser Cys Glu Gly Cys Lys Gly Phe Phe Lys Arg Thr Val Arg Lys Asp
            20                  25                  30

Leu Thr Tyr Thr Cys Arg Asp Asn Lys Asp Cys Leu Ile Asp Lys Arg
        35                  40                  45

Gln Arg Asn Arg Cys Gln Tyr Cys Arg Tyr Gln Lys Cys Leu Ala Met
    50                  55                  60

Gly Met Lys Arg Glu Ala Val Gln Glu Glu Arg Gln Arg Gly Lys Asp
65                  70                  75                  80

Arg Asn Glu Asn Glu Val Glu Ser Thr Ser Ser Ala Asn Glu Asp Met
                85                  90                  95

Pro Val Glu Arg Ile Leu Glu Ala Glu Leu Ala Val Glu Pro Lys Thr
            100                 105                 110

Glu Thr Tyr Val Glu Ala Asn Met Gly Leu Asn Pro Ser Ser Pro Asn
        115                 120                 125

Asp Pro Val Thr Asn Ile Cys Gln Ala Ala Asp Lys Gln Leu Phe Thr
    130                 135                 140

Leu Val Glu Trp Ala Lys Arg Ile Pro His Phe Ser Glu Leu Pro Leu
145                 150                 155                 160

Asp Asp Gln Val Ile Leu Leu Arg Ala Gly Trp Asn Glu Leu Leu Ile
                165                 170                 175

Ala Ser Phe Ser His Arg Ser Ile Ala Val Lys Asp Gly Ile Leu Leu
            180                 185                 190

Ala Thr Gly Leu His Val His Arg Asn Ser Ala His Ser Ala Gly Val
        195                 200                 205

Gly Ala Ile Phe Asp Arg Val Leu Thr Glu Leu Val Ser Lys Met Arg
    210                 215                 220

Asp Met Gln Met Asp Lys Thr Glu Leu Gly Cys Leu Arg Ala Ile Val
225                 230                 235                 240

Leu Phe Asn Pro Asp Ser Lys Gly Leu Ser Asn Pro Ala Glu Val Glu
                245                 250                 255

Ala Leu Arg Glu Lys Val Tyr Ala Ser Leu Glu Ala Tyr Cys Lys His
            260                 265                 270

Lys Tyr Pro Glu Gln Pro Gly Arg Phe Ala Lys Leu Leu Leu Arg Leu
        275                 280                 285

Pro Ala Leu Arg Ser Ile Gly Leu Lys Cys Leu Glu His Leu Phe Phe
    290                 295                 300

Phe Lys Leu Ile Gly Asp Thr Pro Ile Asp Thr Phe Leu Met Glu Met
305                 310                 315                 320

Leu Glu Ala Pro His Gln Met Thr
                325

<210> SEQ ID NO 37
<211> LENGTH: 262
<212> TYPE: PRT
<213> ORGANISM: Homo sapiens
```

```
<220> FEATURE:
<221> NAME/KEY: misc_feature
<223> OTHER INFORMATION: Novel Sequence

<400> SEQUENCE: 37

Lys Arg Glu Ala Val Gln Glu Arg Gln Arg Gly Lys Asp Arg Asn
1               5                   10                  15

Glu Asn Glu Val Glu Ser Thr Ser Ser Ala Asn Glu Asp Met Pro Val
                20                  25                  30

Glu Arg Ile Leu Glu Ala Glu Leu Ala Val Glu Pro Lys Thr Glu Thr
            35                  40                  45

Tyr Val Glu Ala Asn Met Gly Leu Asn Pro Ser Ser Pro Asn Asp Pro
    50                  55                  60

Val Thr Asn Ile Cys Gln Ala Asp Lys Gln Leu Phe Thr Leu Val
65                  70                  75                  80

Glu Trp Ala Lys Arg Ile Pro His Phe Ser Glu Leu Pro Leu Asp Asp
                85                  90                  95

Gln Val Ile Leu Leu Arg Ala Gly Trp Asn Glu Leu Leu Ile Ala Ser
            100                 105                 110

Phe Ser His Arg Ser Ile Ala Val Lys Asp Gly Ile Leu Leu Ala Thr
        115                 120                 125

Gly Leu His Val His Arg Asn Ser Ala His Ser Ala Gly Val Gly Ala
    130                 135                 140

Ile Phe Asp Arg Val Leu Thr Glu Leu Val Ser Lys Met Arg Asp Met
145                 150                 155                 160

Gln Met Asp Lys Thr Glu Leu Gly Cys Leu Arg Ala Ile Val Leu Phe
                165                 170                 175

Asn Pro Asp Ser Lys Gly Leu Ser Asn Pro Ala Glu Val Glu Ala Leu
            180                 185                 190

Arg Glu Lys Val Tyr Ala Ser Leu Glu Ala Tyr Cys Lys His Lys Tyr
        195                 200                 205

Pro Glu Gln Pro Gly Arg Phe Ala Lys Leu Leu Leu Arg Leu Pro Ala
    210                 215                 220

Leu Arg Ser Ile Gly Leu Lys Cys Leu Glu His Leu Phe Phe Phe Lys
225                 230                 235                 240

Leu Ile Gly Asp Thr Pro Ile Asp Thr Phe Leu Met Glu Met Leu Glu
                245                 250                 255

Ala Pro His Gln Met Thr
            260

<210> SEQ ID NO 38
<211> LENGTH: 237
<212> TYPE: PRT
<213> ORGANISM: Homo sapiens
<220> FEATURE:
<221> NAME/KEY: misc_feature
<223> OTHER INFORMATION: Novel Sequence

<400> SEQUENCE: 38

Ala Asn Glu Asp Met Pro Val Glu Arg Ile Leu Glu Ala Glu Leu Ala
1               5                   10                  15

Val Glu Pro Lys Thr Glu Thr Tyr Val Glu Ala Asn Met Gly Leu Asn
                20                  25                  30

Pro Ser Ser Pro Asn Asp Pro Val Thr Asn Ile Cys Gln Ala Ala Asp
            35                  40                  45

Lys Gln Leu Phe Thr Leu Val Glu Trp Ala Lys Arg Ile Pro His Phe
        50                  55                  60
```

```
Ser Glu Leu Pro Leu Asp Asp Gln Val Ile Leu Leu Arg Ala Gly Trp
 65                  70                  75                  80

Asn Glu Leu Leu Ile Ala Ser Phe Ser His Arg Ser Ile Ala Val Lys
                 85                  90                  95

Asp Gly Ile Leu Leu Ala Thr Gly Leu His Val His Arg Asn Ser Ala
            100                 105                 110

His Ser Ala Gly Val Gly Ala Ile Phe Asp Arg Val Leu Thr Glu Leu
        115                 120                 125

Val Ser Lys Met Arg Asp Met Gln Met Asp Lys Thr Glu Leu Gly Cys
    130                 135                 140

Leu Arg Ala Ile Val Leu Phe Asn Pro Asp Ser Lys Gly Leu Ser Asn
145                 150                 155                 160

Pro Ala Glu Val Glu Ala Leu Arg Glu Lys Val Tyr Ala Ser Leu Glu
                165                 170                 175

Ala Tyr Cys Lys His Lys Tyr Pro Glu Gln Pro Gly Arg Phe Ala Lys
            180                 185                 190

Leu Leu Leu Arg Leu Pro Ala Leu Arg Ser Ile Gly Leu Lys Cys Leu
        195                 200                 205

Glu His Leu Phe Phe Phe Lys Leu Ile Gly Asp Thr Pro Ile Asp Thr
    210                 215                 220

Phe Leu Met Glu Met Leu Glu Ala Pro His Gln Met Thr
225                 230                 235

<210> SEQ ID NO 39
<211> LENGTH: 177
<212> TYPE: PRT
<213> ORGANISM: Homo sapiens
<220> FEATURE:
<221> NAME/KEY: misc_feature
<223> OTHER INFORMATION: Novel Sequence

<400> SEQUENCE: 39

Ile Pro His Phe Ser Glu Leu Pro Leu Asp Asp Gln Val Ile Leu Leu
 1               5                  10                  15

Arg Ala Gly Trp Asn Glu Leu Leu Ile Ala Ser Phe Ser His Arg Ser
            20                  25                  30

Ile Ala Val Lys Asp Gly Ile Leu Leu Ala Thr Gly Leu His Val His
        35                  40                  45

Arg Asn Ser Ala His Ser Ala Gly Val Gly Ala Ile Phe Asp Arg Val
 50                  55                  60

Leu Thr Glu Leu Val Ser Lys Met Arg Asp Met Gln Met Asp Lys Thr
 65                  70                  75                  80

Glu Leu Gly Cys Leu Arg Ala Ile Val Leu Phe Asn Pro Asp Ser Lys
                 85                  90                  95

Gly Leu Ser Asn Pro Ala Glu Val Glu Ala Leu Arg Glu Lys Val Tyr
            100                 105                 110

Ala Ser Leu Glu Ala Tyr Cys Lys His Lys Tyr Pro Glu Gln Pro Gly
        115                 120                 125

Arg Phe Ala Lys Leu Leu Leu Arg Leu Pro Ala Leu Arg Ser Ile Gly
    130                 135                 140

Leu Lys Cys Leu Glu His Leu Phe Phe Phe Lys Leu Ile Gly Asp Thr
145                 150                 155                 160

Pro Ile Asp Thr Phe Leu Met Glu Met Leu Glu Ala Pro His Gln Met
                165                 170                 175

Thr
```

<210> SEQ ID NO 40
<211> LENGTH: 224
<212> TYPE: PRT
<213> ORGANISM: Homo sapiens
<220> FEATURE:
<221> NAME/KEY: misc_feature
<223> OTHER INFORMATION: Novel Sequence

<400> SEQUENCE: 40

```
Ala Asn Glu Asp Met Pro Val Glu Arg Ile Leu Glu Ala Glu Leu Ala
1               5                   10                  15

Val Glu Pro Lys Thr Glu Thr Tyr Val Glu Ala Asn Met Gly Leu Asn
            20                  25                  30

Pro Ser Ser Pro Asn Asp Pro Val Thr Asn Ile Cys Gln Ala Ala Asp
        35                  40                  45

Lys Gln Leu Phe Thr Leu Val Glu Trp Ala Lys Arg Ile Pro His Phe
    50                  55                  60

Ser Glu Leu Pro Leu Asp Asp Gln Val Ile Leu Leu Arg Ala Gly Trp
65                  70                  75                  80

Asn Glu Leu Leu Ile Ala Ser Phe Ser His Arg Ser Ile Ala Val Lys
                85                  90                  95

Asp Gly Ile Leu Leu Ala Thr Gly Leu His Val His Arg Asn Ser Ala
            100                 105                 110

His Ser Ala Gly Val Gly Ala Ile Phe Asp Arg Val Leu Thr Glu Leu
        115                 120                 125

Val Ser Lys Met Arg Asp Met Gln Met Asp Lys Thr Glu Leu Gly Cys
    130                 135                 140

Leu Arg Ala Ile Val Leu Phe Asn Pro Asp Ser Lys Gly Leu Ser Asn
145                 150                 155                 160

Pro Ala Glu Val Glu Ala Leu Arg Glu Lys Val Tyr Ala Ser Leu Glu
                165                 170                 175

Ala Tyr Cys Lys His Lys Tyr Pro Glu Gln Pro Gly Arg Phe Ala Lys
            180                 185                 190

Leu Leu Leu Arg Leu Pro Ala Leu Arg Ser Ile Gly Leu Lys Cys Leu
        195                 200                 205

Glu His Leu Phe Phe Phe Lys Leu Ile Gly Asp Thr Pro Ile Asp Thr
    210                 215                 220
```

<210> SEQ ID NO 41
<211> LENGTH: 198
<212> TYPE: DNA
<213> ORGANISM: Choristoneura fumiferana

<400> SEQUENCE: 41

```
tgtctggtat gcggggacag agcctccgga taccactaca atgcgctcac gtgtgaaggg      60
tgtaaagggt tcttcagacg gagtgttacc aaaaatgcgg tttatatttg taaattcggt     120
cacgcttgcg aaatggacat gtacatgcga cggaaatgcc aggagtgccg cctgaagaag     180
tgcttagctg taggcatg                                                   198
```

<210> SEQ ID NO 42
<211> LENGTH: 66
<212> TYPE: PRT
<213> ORGANISM: Choristoneura fumiferana

<400> SEQUENCE: 42

Cys Leu Val Cys Gly Asp Arg Ala Ser Gly Tyr His Tyr Asn Ala Leu

```
                    1               5                  10                  15
Thr Cys Glu Gly Cys Lys Gly Phe Phe Arg Arg Ser Val Thr Lys Asn
                   20                  25                  30

Ala Val Tyr Ile Cys Lys Phe Gly His Ala Cys Glu Met Asp Met Tyr
                   35                  40              45

Met Arg Arg Lys Cys Gln Glu Cys Arg Leu Lys Lys Cys Leu Ala Val
         50                  55                  60

Gly Met
65

<210> SEQ ID NO 43
<211> LENGTH: 441
<212> TYPE: DNA
<213> ORGANISM: Saccharomyces cerevisiae
<220> FEATURE:
<221> NAME/KEY: misc_feature
<223> OTHER INFORMATION: Novel Sequence

<400> SEQUENCE: 43
atgaagctac tgtcttctat cgaacaagca tgcgatattt gccgacttaa aaagctcaag      60
tgctccaaag aaaaaccgaa gtgcgccaag tgtctgaaga caactgggga gtgtcgctac     120
tctcccaaaa ccaaaaggtc tccgctgact agggcacatc tgacagaagt ggaatcaagg     180
ctagaaagac tggaacagct atttctactg atttttcctc gagaagacct tgacatgatt     240
ttgaaaatgg attctttaca ggatataaaa gcattgttaa caggattatt tgtacaagat     300
aatgtgaata aagatgccgt cacagataga ttggcttcag tggagactga tatgcctcta     360
acattgagac agcatagaat aagtgcgaca tcatcatcgg aagagagtag taacaaaggt     420
caaagacagt tgactgtatc g                                               441

<210> SEQ ID NO 44
<211> LENGTH: 147
<212> TYPE: PRT
<213> ORGANISM: Saccharomyces cerevisiae
<220> FEATURE:
<221> NAME/KEY: misc_feature
<223> OTHER INFORMATION: Novel Sequence

<400> SEQUENCE: 44

Met Lys Leu Leu Ser Ser Ile Glu Gln Ala Cys Asp Ile Cys Arg Leu
1               5                  10                  15

Lys Lys Leu Lys Cys Ser Lys Glu Lys Pro Lys Cys Ala Lys Cys Leu
                   20                  25                  30

Lys Asn Asn Trp Glu Cys Arg Tyr Ser Pro Lys Thr Lys Arg Ser Pro
                   35                  40                  45

Leu Thr Arg Ala His Leu Thr Glu Val Glu Ser Arg Leu Glu Arg Leu
         50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
                  100                 105                 110

Ser Val Glu Thr Asp Met Pro Leu Thr Leu Arg Gln His Arg Ile Ser
                 115                 120                 125

Ala Thr Ser Ser Ser Glu Glu Ser Ser Asn Lys Gly Gln Arg Gln Leu
         130                 135                 140
```

Thr Val Ser
145

<210> SEQ ID NO 45
<211> LENGTH: 606
<212> TYPE: DNA
<213> ORGANISM: Escherichia coli
<220> FEATURE:
<221> NAME/KEY: misc_feature
<223> OTHER INFORMATION: Novel Sequence

<400> SEQUENCE: 45

```
atgaaagcgt taacggccag gcaacaagag gtgtttgatc tcatccgtga tcacatcagc    60
cagacaggta tgccgccgac gcgtgcggaa atcgcgcagc gtttggggtt ccgttcccca   120
aacgcggctg aagaacatct gaaggcgctg gcacgcaaag gcgttattga aattgtttcc   180
ggcgcatcac gcgggattcg tctgttgcag gaagaggaag aagggttgcc gctggtaggt   240
cgtgtggctg ccggtgaacc acttctggcg caacagcata ttgaaggtca ttatcaggtc   300
gatccttcct tattcaagcc gaatgctgat ttcctgctgc gcgtcagcgg gatgtcgatg   360
aaagatatcg gcattatgga tggtgacttg ctggcagtgc ataaaactca ggatgtacgt   420
aacggtcagg tcgttgtcgc acgtattgat gacgaagtta ccgttaagcg cctgaaaaaa   480
cagggcaata aagtcgaact gttgccagaa aatagcgagt ttaaaccaat tgtcgtagat   540
cttcgtcagc agagcttcac cattgaaggg ctggcggttg gggttattcg caacggcgac   600
tggctg                                                              606
```

<210> SEQ ID NO 46
<211> LENGTH: 202
<212> TYPE: PRT
<213> ORGANISM: Escherichia coli
<220> FEATURE:
<221> NAME/KEY: misc_feature
<223> OTHER INFORMATION: Novel Sequence

<400> SEQUENCE: 46

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu
        195                 200

<210> SEQ ID NO 47
<211> LENGTH: 420
<212> TYPE: DNA
<213> ORGANISM: Choristoneura fumiferana

<400> SEQUENCE: 47
atgagacgcc gctggtccaa caacgggggc ttccagacgc tgcgaatgct cgaggagagc      60
tcgtccgaag tgacgtcgtc ctcagctctg ggtctgccgg ccgcgatggt tatgtctccg     120
gagtcgctcg cctcgccaga gtacggcggg ctcgagctct ggggatacga cgatgggttg     180
tcatacaaca cggcgcagtc cttgctgggc aatacttgca cgatgcagca gcagcaacag     240
acgcagccgc tgccgtcgat gccgttgcct atgccgccga ccacgccgaa gtctgaaaac     300
gagtctattt cctcaggccg tgaggaactg tcgccagctt caagtataaa tgggtgcagt     360
acagatggcg aggcacgacg tcagaagaag ggccctgcgc ccgtcagca agaggaactg     420

<210> SEQ ID NO 48
<211> LENGTH: 140
<212> TYPE: PRT
<213> ORGANISM: Choristoneura fumiferana

<400> SEQUENCE: 48

Met Arg Arg Arg Trp Ser Asn Asn Gly Gly Phe Gln Thr Leu Arg Met
1               5                  10                  15

Leu Glu Glu Ser Ser Ser Glu Val Thr Ser Ser Ser Ala Leu Gly Leu
            20                  25                  30

Pro Ala Ala Met Val Met Ser Pro Glu Ser Leu Ala Ser Pro Glu Tyr
        35                  40                  45

Gly Gly Leu Glu Leu Trp Gly Tyr Asp Asp Gly Leu Ser Tyr Asn Thr
    50                  55                  60

Ala Gln Ser Leu Leu Gly Asn Thr Cys Thr Met Gln Gln Gln Gln Gln
65                  70                  75                  80

Thr Gln Pro Leu Pro Ser Met Pro Leu Pro Met Pro Pro Thr Thr Pro
                85                  90                  95

Lys Ser Glu Asn Glu Ser Ile Ser Ser Gly Arg Glu Glu Leu Ser Pro
            100                 105                 110

Ala Ser Ser Ile Asn Gly Cys Ser Thr Asp Gly Glu Ala Arg Arg Gln
        115                 120                 125

Lys Lys Gly Pro Ala Pro Arg Gln Gln Glu Glu Leu
    130                 135                 140

<210> SEQ ID NO 49
<211> LENGTH: 271
<212> TYPE: DNA
<213> ORGANISM: herpes simplex virus 7
<220> FEATURE:
<221> NAME/KEY: misc_feature
<223> OTHER INFORMATION: Novel Sequence

<400> SEQUENCE: 49
atgggcccta aaagaagcg taaagtcgcc cccccgaccg atgtcagcct ggggggacgag      60 ctccacttag acggcgagga cgtggcgatg gcgcatgccg acgcgctaga cgatttcgat     120

```
ctggacatgt tgggggacgg ggattccccg gggccgggat ttaccccca cgactccgcc    180 ccctacggcg ctctggatat ggccgacttc gagtttgagc agatgtttac cgatgccctt   240
ggaattgacg agtacggtgg ggaattcccg g                                  271
```

<210> SEQ ID NO 50
<211> LENGTH: 90
<212> TYPE: PRT
<213> ORGANISM: herpes simplex virus 7
<220> FEATURE:
<221> NAME/KEY: misc_feature
<223> OTHER INFORMATION: Novel Sequence

<400> SEQUENCE: 50

```
Met Gly Pro Lys Lys Arg Lys Val Ala Pro Pro Thr Asp Val Ser
1               5                   10                  15

Leu Gly Asp Glu Leu His Leu Asp Gly Glu Asp Val Ala Met Ala His
                20                  25                  30

Ala Asp Ala Leu Asp Asp Phe Asp Leu Asp Met Leu Gly Asp Gly Asp
            35                  40                  45

Ser Pro Gly Pro Gly Phe Thr Pro His Asp Ser Ala Pro Tyr Gly Ala
50                  55                  60

Leu Asp Met Ala Asp Phe Glu Phe Glu Gln Met Phe Thr Asp Ala Leu
65                  70                  75                  80

Gly Ile Asp Glu Tyr Gly Gly Glu Phe Pro
                85                  90
```

<210> SEQ ID NO 51
<211> LENGTH: 307
<212> TYPE: DNA
<213> ORGANISM: Saccharomyces cerevisiae

<400> SEQUENCE: 51

```
atgggtgctc ctccaaaaaa gaagagaaag gtagctggta tcaataaaga tatcgaggag    60
tgcaatgcca tcattgagca gtttatcgac tacctgcgca ccggacagga gatgccgatg   120
gaaatggcgg atcaggcgat taacgtggtg ccgggcatga cgccgaaaac cattcttcac   180
gccgggccgc cgatccagcc tgactggctg aaatcgaatg gttttcatga aattgaagcg   240
gatgttaacg ataccagcct cttgctgagt ggagatgcct cctaccctta tgatgtgcca   300
gattatg                                                             307
```

<210> SEQ ID NO 52
<211> LENGTH: 102
<212> TYPE: PRT
<213> ORGANISM: Saccharomyces cerevisiae

<400> SEQUENCE: 52

```
Met Gly Ala Pro Pro Lys Lys Lys Arg Lys Val Ala Gly Ile Asn Lys
1               5                   10                  15

Asp Ile Glu Glu Cys Asn Ala Ile Ile Glu Gln Phe Ile Asp Tyr Leu
                20                  25                  30

Arg Thr Gly Gln Glu Met Pro Met Glu Met Ala Asp Gln Ala Ile Asn
            35                  40                  45

Val Val Pro Gly Met Thr Pro Lys Thr Ile Leu His Ala Gly Pro Pro
50                  55                  60

Ile Gln Pro Asp Trp Leu Lys Ser Asn Gly Phe His Glu Ile Glu Ala
65                  70                  75                  80

Asp Val Asn Asp Thr Ser Leu Leu Leu Ser Gly Asp Ala Ser Tyr Pro
```

-continued

```
                        85                  90                  95
Tyr Asp Val Pro Asp Tyr
                100

<210> SEQ ID NO 53
<211> LENGTH: 807
<212> TYPE: DNA
<213> ORGANISM: Homo sapiens

<400> SEQUENCE: 53
cccatggaat tccagtacct gccagataca gacgatcgtc accggattga ggagaaacgt    60
aaaaggacat atgagacctt caagagcatc atgaagaaga gtcctttcag cggacccacc   120 gaccccggc ctccacctcg acgcattgct gtgccttccc gcagctcagc ttctgtcccc    180
aagccagcac cccagccta tccctttacg tcatccctga gcaccatcaa ctatgatgag    240
tttcccacca tggtgtttcc ttctgggcag atcagccagg cctcggcctt ggccccggcc   300
cctccccaag tcctgcccca ggctccagcc cctgcccctg ctccagccat ggtatcagct   360
ctggcccagg ccccagcccc tgtcccagtc ctagccccag ccctcctca ggctgtggcc    420 ccacctgccc ccaagcccac ccaggctggg aaggaacgc tgtcagaggc cctgctgcag    480
ctgcagtttg atgatgaaga cctgggggcc ttgcttggca acagcacaga cccagctgtg   540
ttcacagacc tggcatccgt cgacaactcc gagtttcagc agctgctgaa ccagggcata   600
cctgtggccc cccacacaac tgagcccatg ctgatggagt accctgaggc tataactcgc   660
ctagtgacag gggcccagag gcccccgac ccagctcctg ctccactggg ggccccgggg    720
ctccccaatg gcctcctttc aggagatgaa gacttctcct ccattgcgga catggacttc   780
tcagccctgc tgagtcagat cagctcc                                       807

<210> SEQ ID NO 54
<211> LENGTH: 269
<212> TYPE: PRT
<213> ORGANISM: Homo sapiens

<400> SEQUENCE: 54

Pro Met Glu Phe Gln Tyr Leu Pro Asp Thr Asp Asp Arg His Arg Ile
1               5                   10                  15

Glu Glu Lys Arg Lys Arg Thr Tyr Glu Thr Phe Lys Ser Ile Met Lys
                20                  25                  30

Lys Ser Pro Phe Ser Gly Pro Thr Asp Pro Arg Pro Pro Pro Arg Arg
            35                  40                  45

Ile Ala Val Pro Ser Arg Ser Ser Ala Ser Val Pro Lys Pro Ala Pro
        50                  55                  60

Gln Pro Tyr Pro Phe Thr Ser Ser Leu Ser Thr Ile Asn Tyr Asp Glu
65                  70                  75                  80

Phe Pro Thr Met Val Phe Pro Ser Gly Gln Ile Ser Gln Ala Ser Ala
                85                  90                  95

Leu Ala Pro Ala Pro Pro Gln Val Leu Pro Gln Ala Pro Ala Pro Ala
                100                 105                 110

Pro Ala Pro Ala Met Val Ser Ala Leu Ala Gln Ala Pro Ala Pro Val
            115                 120                 125

Pro Val Leu Ala Pro Gly Pro Pro Gln Ala Val Ala Pro Pro Ala Pro
        130                 135                 140

Lys Pro Thr Gln Ala Gly Glu Gly Thr Leu Ser Glu Ala Leu Leu Gln
145                 150                 155                 160
```

```
Leu Gln Phe Asp Asp Glu Asp Leu Gly Ala Leu Leu Gly Asn Ser Thr
                165                 170                 175

Asp Pro Ala Val Phe Thr Asp Leu Ala Ser Val Asp Asn Ser Glu Phe
            180                 185                 190

Gln Gln Leu Leu Asn Gln Gly Ile Pro Val Ala Pro His Thr Thr Glu
        195                 200                 205

Pro Met Leu Met Glu Tyr Pro Glu Ala Ile Thr Arg Leu Val Thr Gly
    210                 215                 220

Ala Gln Arg Pro Pro Asp Pro Ala Pro Ala Pro Leu Gly Ala Pro Gly
225                 230                 235                 240

Leu Pro Asn Gly Leu Leu Ser Gly Asp Glu Asp Phe Ser Ser Ile Ala
                245                 250                 255

Asp Met Asp Phe Ser Ala Leu Leu Ser Gln Ile Ser Ser
                260                 265
```

<210> SEQ ID NO 55
<211> LENGTH: 225
<212> TYPE: DNA
<213> ORGANISM: Drosophila melanogaster
<220> FEATURE:
<221> NAME/KEY: misc_feature
<223> OTHER INFORMATION: Novel Sequence

<400> SEQUENCE: 55

| | | | | | |
|---|---|---|---|---|---|
| tcgacattgg | acaagtgcat | tgaacccttg | tctctcgaga | gacaagggg | ttcaatgcac | 60 |
| ttgtccaatg | tcgagagaca | aggggttca | atgcacttgt | ccaatgtcga | gagacaaggg | 120 |
| ggttcaatgc | acttgtccaa | tgtcgagaga | caagggggtt | caatgcactt | gtccaatgtc | 180 |
| gagagacaag | ggggttcaat | gcacttgtcc | aatgtcgact | ctaga | | 225 |

<210> SEQ ID NO 56
<211> LENGTH: 19
<212> TYPE: DNA
<213> ORGANISM: Saccharomyces cerevisiae
<220> FEATURE:
<221> NAME/KEY: misc_feature
<223> OTHER INFORMATION: Novel Sequence

<400> SEQUENCE: 56
ggagtactgt cctccgagc                                                   19

<210> SEQ ID NO 57
<211> LENGTH: 666
<212> TYPE: DNA
<213> ORGANISM: Escherichia coli
<220> FEATURE:
<221> NAME/KEY: misc_feature
<223> OTHER INFORMATION: Novel Sequence

<400> SEQUENCE: 57

| | | | | | |
|---|---|---|---|---|---|
| ggatcccag | cttggaattc | gacaggttat | cagcaacaac | acagtcatat | ccattctcaa | 60 |
| ttagctctac | cacagtgtgt | gaaccaatgt | atccagcacc | acctgtaacc | aaaacaattt | 120 |
| tagaagtact | tcactttgt | aactgagctg | tcatttatat | tgaattttca | aaaattctta | 180 |
| cttttttttt | ggatggacgc | aaagaagttt | aataatcata | ttacatggca | ttaccaccat | 240 |
| atacatatcc | atatacatat | ccatatctaa | tcttacctcg | actgctgtat | ataaaaccag | 300 |
| tggttatatg | tacagtactg | ctgtatataa | aaccagtggt | tatatgtaca | gtacgtcgac | 360 |
| tgctgtatat | aaaaccagtg | gttatatgta | cagtactgct | gtatataaaa | ccagtggtta | 420 |
| tatgtacagt | acgtcgaggg | atgataatgc | gattagtttt | ttagccttat | ttctggggta | 480 |

```
attaatcagc gaagcgatga tttttgatct attaacagat atataaatgc aaaaactgca      540
taaccacttt aactaatact ttcaacattt tcggtttgta ttacttctta ttcaaatgta      600
ataaaagtat caacaaaaaa ttgttaatat acctctatac tttaacgtca aggagaaaaa      660
actata                                                                 666
```

<210> SEQ ID NO 58
<211> LENGTH: 1542
<212> TYPE: DNA
<213> ORGANISM: Choristoneura fumiferana
<220> FEATURE:
<221> NAME/KEY: misc_feature
<223> OTHER INFORMATION: Novel Sequence

<400> SEQUENCE: 58

```
ctggacctga aacacgaagt ggcttaccga ggggtgctcc caggccaggt gaaggccgaa       60 ccggggtcc acaacggcca ggtcaacggc cacgtgaggg actggatggc aggcggcgct      120
ggtgccaatt cgccgtctcc gggagcggtg gctcaacccc agcctaacaa tgggtattcg      180
tcgccactct cctcgggaag ctacgggccc tacagtccaa atgggaaaat aggccgtgag      240
gaactgtcgc cagcttcaag tataaatggg tgcagtacag atgcgaggc acgacgtcag       300 aagaagggcc ctgcgccccg tcagcaagag gaactgtgtc tggtatgcgg ggacagagcc      360
tccggatacc actacaatgc gctcacgtgt gaaggtgta aggggttctt cagacggagt       420
gttaccaaaa atgcggttta tatttgtaaa ttcggtcacg cttgcgaaat ggacatgtac      480
atgcgacgga aatgccagga gtgccgcctg aagaagtgct tagctgtagg catgaggcct      540
gagtgcgtag tacccgagac tcagtgcgcc atgaagcgga aagagaagaa agcacagaag      600
gagaaggaca aactgcctgt cagcacgacg acggtggacg accacatgcc gcccattatg      660
cagtgtgaac ctccacctcc tgaagcagca aggattcacg aagtggtccc aaggtttctc      720
tccgacaagc tgttggagac aaaccggcag aaaaacatcc cccagttgac agccaaccag      780
cagttcctta tcgccaggct catctggtac caggacgggt acgagcagcc ttctgatgaa      840
gatttgaaga ggattacgca gacgtggcag caagcggacg atgaaaacga agtctgac       900 actcccttcc gccagatcac agagatgact atcctcacgg tccaacttat cgtggagttc      960
gcgaagggat tgccagggtt cgccaagatc tcgcagcctg atcaaattac gctgcttaag     1020
gcttgctcaa gtgaggtaat gatgctccga gtcgcgcgac gatacgatgc ggcctcagac     1080
agtgttctgt tcgcgaacaa ccaagcgtac actcgcgaca actaccgcaa ggctggcatg     1140
gcctacgtca tcgaggatct actgcacttc tgccggtgca tgtactctat ggcgttggac     1200
aacatccatt acgcgctgct cacggctgtc gtcatctttt ctgaccggcc agggttggag     1260
cagccgcaac tggtggaaga aatccagcgg tactacctga atacgctccg catctatatc     1320
ctgaaccagc tgagcgggtc ggcgcgttcg tccgtcatat acggcaagat cctctcaatc     1380
ctctctgagc tacgcacgct cggcatgcaa aactccaaca tgtgcatctc cctcaagctc     1440
aagaacagaa agctgccgcc tttcctcgag gagatctggg atgtggcgga catgtcgcac     1500
acccaaccgc cgcctatcct cgagtccccc acgaatctct ag                        1542
```

<210> SEQ ID NO 59
<211> LENGTH: 513
<212> TYPE: PRT
<213> ORGANISM: Choristoneura fumiferana
<220> FEATURE:
<221> NAME/KEY: misc_feature -continued
<223> OTHER INFORMATION: Novel Sequence

<400> SEQUENCE: 59

```
Leu Asp Leu Lys His Glu Val Ala Tyr Arg Gly Val Leu Pro Gly Gln
  1               5                  10                 15

Val Lys Ala Glu Pro Gly Val His Asn Gly Gln Val Asn Gly His Val
             20                  25                  30

Arg Asp Trp Met Ala Gly Ala Gly Ala Asn Ser Pro Ser Pro Gly
         35                  40                  45

Ala Val Ala Gln Pro Gln Pro Asn Asn Gly Tyr Ser Ser Pro Leu Ser
         50                  55                  60

Ser Gly Ser Tyr Gly Pro Tyr Ser Pro Asn Gly Lys Ile Gly Arg Glu
 65                  70                  75                  80

Glu Leu Ser Pro Ala Ser Ser Ile Asn Gly Cys Ser Thr Asp Gly Glu
                 85                  90                  95

Ala Arg Arg Gln Lys Lys Gly Pro Ala Pro Arg Gln Gln Glu Glu Leu
            100                 105                 110

Cys Leu Val Cys Gly Asp Arg Ala Ser Gly Tyr His Tyr Asn Ala Leu
            115                 120                 125

Thr Cys Glu Gly Cys Lys Gly Phe Phe Arg Arg Ser Val Thr Lys Asn
        130                 135                 140

Ala Val Tyr Ile Cys Lys Phe Gly His Ala Cys Glu Met Asp Met Tyr
145                 150                 155                 160

Met Arg Arg Lys Cys Gln Glu Cys Arg Leu Lys Lys Cys Leu Ala Val
                165                 170                 175

Gly Met Arg Pro Glu Cys Val Val Pro Glu Thr Gln Cys Ala Met Lys
            180                 185                 190

Arg Lys Glu Lys Lys Ala Gln Lys Glu Lys Asp Lys Leu Pro Val Ser
        195                 200                 205

Thr Thr Thr Val Asp Asp His Met Pro Pro Ile Met Gln Cys Glu Pro
210                 215                 220

Pro Pro Pro Glu Ala Ala Arg Ile His Glu Val Val Pro Arg Phe Leu
225                 230                 235                 240

Ser Asp Lys Leu Leu Glu Thr Asn Arg Gln Lys Asn Ile Pro Gln Leu
                245                 250                 255

Thr Ala Asn Gln Gln Phe Leu Ile Ala Arg Leu Ile Trp Tyr Gln Asp
            260                 265                 270

Gly Tyr Glu Gln Pro Ser Asp Glu Asp Leu Lys Arg Ile Thr Gln Thr
        275                 280                 285

Trp Gln Gln Ala Asp Asp Glu Asn Glu Glu Ser Asp Thr Pro Phe Arg
290                 295                 300

Gln Ile Thr Glu Met Thr Ile Leu Thr Val Gln Leu Ile Val Glu Phe
305                 310                 315                 320

Ala Lys Gly Leu Pro Gly Phe Ala Lys Ile Ser Gln Pro Asp Gln Ile
                325                 330                 335

Thr Leu Leu Lys Ala Cys Ser Ser Glu Val Met Met Leu Arg Val Ala
            340                 345                 350

Arg Arg Tyr Asp Ala Ala Ser Asp Ser Val Leu Phe Ala Asn Asn Gln
        355                 360                 365

Ala Tyr Thr Arg Asp Asn Tyr Arg Lys Ala Gly Met Ala Tyr Val Ile
    370                 375                 380

Glu Asp Leu Leu His Phe Cys Arg Cys Met Tyr Ser Met Ala Leu Asp
385                 390                 395                 400
```

-continued

```
Asn Ile His Tyr Ala Leu Leu Thr Ala Val Val Ile Phe Ser Asp Arg
                405                 410                 415
Pro Gly Leu Glu Gln Pro Gln Leu Val Glu Glu Ile Gln Arg Tyr Tyr
            420                 425                 430
Leu Asn Thr Leu Arg Ile Tyr Ile Leu Asn Gln Leu Ser Gly Ser Ala
        435                 440                 445
Arg Ser Ser Val Ile Tyr Gly Lys Ile Leu Ser Ile Leu Ser Glu Leu
    450                 455                 460
Arg Thr Leu Gly Met Gln Asn Ser Asn Met Cys Ile Ser Leu Lys Leu
465                 470                 475                 480
Lys Asn Arg Lys Leu Pro Pro Phe Leu Glu Glu Ile Trp Asp Val Ala
                485                 490                 495

Asp Met Ser His Thr Gln Pro Pro Pro Ile Leu Glu Ser Pro Thr Asn
            500                 505                 510

Leu

<210> SEQ ID NO 60
<211> LENGTH: 4375
<212> TYPE: DNA
<213> ORGANISM: Choristoneura fumiferana
<220> FEATURE:
<221> NAME/KEY: misc_feature
<223> OTHER INFORMATION: Novel Sequence

<400> SEQUENCE: 60
tgtaattttg atgggcgccg tgatgcaccg tgtgccatat tgccatccag tcgaatagaa      60
aaaaaaaaaa aaaaaaaaat atcagttgtt ttgtccctcg ctcgctttcg agtgtattcg     120
gaatattaga cgtcataatt cacgagtgtc ttttaaattt atatagcgat tagcggggcc     180
gtttgttgga cgtgcgcttg cgtttagtgg agtgcaggga tagtgaggcg agtatggtag     240
ttcgtggtca tgtcaagtgt ggcgaagaaa gacaagccga cgatgtcggt gacggcgctg     300
atcaactggg cgcggccggc gccgccaggc ccgccgcagc cgcagtcagc gtcgcctgcg     360
ccggcagcca tgctgcagca gctcccgacg cagtcaatgc agtcgttaaa ccacatccca     420
actgtcgatt gctcgctcga tatgcagtgg cttaatttag aacctggatt catgtcgcct     480
atgtcacctc ctgagatgaa accagacacc gccatgcttg atgggctacg agacgacgcc     540
acttcgccgc ctaacttcaa gaactacccg cctaatcacc ccctgagtgg ctccaaacac     600
ctatgctcta tatgcggcga cagggcgtct gggaagcact atggggtgta cagttgcgaa     660
ggatgcaagg gtttcttcaa gcggaccgtc cggaaggacc tgtcgtacgc ttgccgggag     720
gagcggaact gcatcataga caagcgacaa aggaaccgat gccagtactg ccgctatcaa     780
aagtgtttgg cttgcggtat gaagcgagag gcggtgcaag aggagcgcca gaggaatgct     840
cgcggcgcgg aggatgcgca cccgagtagc tcggtgcagg taagcgatga gctgtcaatc     900
gagcgcctaa cggagatgga gtctttggtg gcagatccca gcgaggagtt ccagttcctc     960
cgcgtggggc ctgacagcaa cgtgcctcca cgttaccgcg cgcccgtctc ctccctctgc    1020
caaataggca acaagcaaat agcggcgttg gtggtatggg cgcgcgacat ccctcatttc    1080
gggcagctgg agctggacga tcaagtggta ctcatcaagg cctcctggaa tgagctgcta    1140
ctcttcgcca tcgcctggcg ctctatggag tatttggaag atgagaggga gaacggggac    1200
ggaacgcgga gcaccactca gccacaactg atgtgtctca tgcctggcat gacgttgcac    1260
cgcaactcgg cgcagcaggc gggcgtgggc gccatcttcg accgcgtgct gtccgagctc    1320
agtctgaaga tgcgcacctt gcgcatggac caggccgagt acgtcgcgct caaagccatc    1380
```

-continued

```
gtgctgctca accctgatgt gaaaggactg aagaatcggc aagaagttga cgttttgcga   1440
gaaaaaatgt tctcttgcct ggacgactac tgccggcggt cgcgaagcaa cgaggaaggc   1500
cggtttgcgt ccttgctgct gcggctgcca gctctccgct ccatctcgct caagagcttc   1560
gaacacctct acttcttcca cctcgtggcc gaaggctcca tcagcggata catacgagag   1620
gcgctccgaa accacgcgcc tccgatcgac gtcaatgcca tgatgtaaag tgcgatacac   1680
gccctgccga tgtgagaaga actatggcta atagaagcga aactgaatac atctagggtg   1740
ggacttaact tgggactatc attaaagtat cacgcaaatt atgcgtagtc agaaagtcgc   1800
gtcgatcaaa cttttttata acgaattga gtttctaacg actgcaacac agcggagttt   1860
tgcttctgat agttttatt ctaatggtta agatgcttta cacgggcatt attgacattc   1920
aagtgtaagt ggaagttgac aaccttgaca tttatatcac gtttgtaatt ggttaaataa   1980
attaattaat cacaagtaag actaacatca acgtcacgat actaacgcca tttagtgata   2040
tttttcatgt caagaaactc attgttttga taaatatttt ttctaattac tccagtgaac   2100
tcatccaaat gtgacccagt ttcccgcaga gttgcccgtg taaatcatc tttagggaca   2160
tatccccgc tatctcatga aattccaagg atcagtaggg gccaattccc ccgatgtgtt   2220
gggaggcaga attttcgata atctacgact attgttagcc tacgaattag ttgaattttt   2280
tgaaattatt tttattaagt cgccactttc caaacacatc agcagggtat atgtgcaatt   2340
ttgtaacgat aactctattc atttctgata tttatcgaaa ttttatctta cataacatgc   2400
tggctggtcc agtgtttgg tagttacata tgtatctacg gtttgtttta aattatagct   2460
tttttattgt aatctgtata aaattgagtt atcttacttc acactacgat cgagtaaacc   2520
catcgtcagc tacgaaaaac taatcgtata aggcgtaaga gtaaataact aattgacaac   2580
cagcaacgag gaccacctca gtcctcgtgc ttacattgtg ccgtagctta atatgatgga   2640
agctgtcgtc gttacgacat tagataaagt gcatgaatac caaaaatgta ccatcccgta   2700
ctgatctctc atgctctcgc tgcgtgggac ccgtgtcgag tgtcgtaagg actgactaat   2760
attttagact aggcgtctat gcttcagtaa ttccttatac atattataag tcatccaaat   2820
aacgagtaag gcggcatgtt gagatcagca ttccgagagt caaagagccc ctaacgtgac   2880
tgagaagtag agacaataca ctgattttct gagatgaacg caaccgagat tgacactaaa   2940
aatctattta tggatttcaa aatggcgatg cttgattgtc tgcggcgtgg atagactgaa   3000
atgggtttgc ttaacactgg atattgtttt tattagttaa tagtcttaca ttgcaagttg   3060
gtaattcggt gctaatatcg accggtttgt taactatcta acggttccca gtgtcaggca   3120
cacatctttc ccaagcagac aacgcaagag tgtacaaaat gtacatgtta caaaataagg   3180
aacattcgtc ggataagtgt aacagttgat aggtaaagaa aatggggccg cctctttatt   3240
attacgtagc cgtaaaatta ttaacgtatt tagtttagat gttcagctaa ttaggataat   3300
tctatttgtc gagtacctag atgtccatag tgaattaata taataattag actgttacgc   3360
gtaggtaatt ataagttta ccaaatctct cttcaaagca aaactttgt cacttccgt    3420
actgagacgt cgtagcttat tctgattcac gaaatatttg gatcacattg ttacaaggcg   3480
accgtcacgt agtatatgat tatttacaaa tgacacgtat gtatcaatgc tataagtgtt   3540
ttcgttacat atgtcggtgc tttaacgtgc atttcgatgt gcagattaaa aatagcaaga   3600
aatcttgaaa ttgttttaga aaatatttga tttccttatt gaaagttatt tttaaatgta   3660
aatatttcgt aatcataata attatgtatt gtgtagttat ttcaccttta cggttgggat   3720
```

-continued

```
attatttaat ggtggcctac gaaagtgatt ataaccatcc gcgtcctcaa aaaggccagt   3780
ttatttttgt acctcataca tactaattac gtaagtaata tcaggcgaat ggttgactaa   3840
caactaacca gtattaaaaa ttaaaagact tcgtcctaat aaaatgtaat atctatgtat   3900
aaaaatgaaa atctggcgt ataataggta aaattaaact agattgttaa tgaatgtgat    3960
gtctcataaa cgtttagttt ttaatgagaa acatgtttag tcgcctacta taagacgaga   4020
cggcaagctc accgagttaa ctcgtaaaca ggaatgttga aaaagatgac acaatttata   4080
tttggtattg aaattatgac taaccatgcg ctctatcgtt tgttatggat gcatagtatt   4140
gctgttgaaa ataatggaat taggtaatta ctgcattaat gttgaaaact tgatattatt   4200
ctatggttgg gtatgaattc tatgttggaa gtgttgcagc ggttgtaaag atgatttata   4260
atgatgttca ctaaatatct gactaaatgt aagttatttt tttttgtata gacatagctt   4320
taagatgaag gtgattaaac tttatcctta tcacaataaa aaaaaaaaa aaaaa         4375
```

<210> SEQ ID NO 61
<211> LENGTH: 472
<212> TYPE: PRT
<213> ORGANISM: Choristoneura fumiferana
<220> FEATURE:
<221> NAME/KEY: misc_feature
<223> OTHER INFORMATION: Novel Sequence

<400> SEQUENCE: 61

```
Met Ser Ser Val Ala Lys Lys Asp Lys Pro Thr Met Ser Val Thr Ala
1               5                   10                  15

Leu Ile Asn Trp Ala Arg Pro Ala Pro Pro Gly Pro Pro Gln Pro Gln
            20                  25                  30

Ser Ala Ser Pro Ala Pro Ala Ala Met Leu Gln Gln Leu Pro Thr Gln
        35                  40                  45

Ser Met Gln Ser Leu Asn His Ile Pro Thr Val Asp Cys Ser Leu Asp
    50                  55                  60

Met Gln Trp Leu Asn Leu Glu Pro Gly Phe Met Ser Pro Met Ser Pro
65                  70                  75                  80

Pro Glu Met Lys Pro Asp Thr Ala Met Leu Asp Gly Leu Arg Asp Asp
                85                  90                  95

Ala Thr Ser Pro Pro Asn Phe Lys Asn Tyr Pro Pro Asn His Pro Leu
            100                 105                 110

Ser Gly Ser Lys His Leu Cys Ser Ile Cys Gly Asp Arg Ala Ser Gly
        115                 120                 125

Lys His Tyr Gly Val Tyr Ser Cys Glu Gly Cys Lys Gly Phe Phe Lys
    130                 135                 140

Arg Thr Val Arg Lys Asp Leu Ser Tyr Ala Cys Arg Glu Glu Arg Asn
145                 150                 155                 160

Cys Ile Ile Asp Lys Arg Gln Arg Asn Arg Cys Gln Tyr Cys Arg Tyr
                165                 170                 175

Gln Lys Cys Leu Ala Cys Gly Met Lys Arg Glu Ala Val Gln Glu Glu
            180                 185                 190

Arg Gln Arg Asn Ala Arg Gly Ala Glu Asp Ala His Pro Ser Ser Ser
        195                 200                 205

Val Gln Val Ser Asp Glu Leu Ser Ile Glu Arg Leu Thr Glu Met Glu
    210                 215                 220

Ser Leu Val Ala Asp Pro Ser Glu Glu Phe Gln Phe Leu Arg Val Gly
225                 230                 235                 240

Pro Asp Ser Asn Val Pro Pro Arg Tyr Arg Ala Pro Val Ser Ser Leu
```

```
                  245                 250                 255
Cys Gln Ile Gly Asn Lys Gln Ile Ala Ala Leu Val Val Trp Ala Arg
            260                 265                 270

Asp Ile Pro His Phe Gly Gln Leu Glu Leu Asp Asp Gln Val Val Leu
            275                 280                 285

Ile Lys Ala Ser Trp Asn Glu Leu Leu Phe Ala Ile Ala Trp Arg
            290                 295                 300

Ser Met Glu Tyr Leu Glu Asp Glu Arg Glu Asn Gly Asp Gly Thr Arg
305                 310                 315                 320

Ser Thr Thr Gln Pro Gln Leu Met Cys Leu Met Pro Gly Met Thr Leu
            325                 330                 335

His Arg Asn Ser Ala Gln Gln Ala Gly Val Gly Ala Ile Phe Asp Arg
            340                 345                 350

Val Leu Ser Glu Leu Ser Leu Lys Met Arg Thr Leu Arg Met Asp Gln
            355                 360                 365

Ala Glu Tyr Val Ala Leu Lys Ala Ile Val Leu Leu Asn Pro Asp Val
            370                 375                 380

Lys Gly Leu Lys Asn Arg Gln Glu Val Asp Val Leu Arg Glu Lys Met
385                 390                 395                 400

Phe Ser Cys Leu Asp Asp Tyr Cys Arg Arg Ser Arg Ser Asn Glu Glu
                405                 410                 415

Gly Arg Phe Ala Ser Leu Leu Leu Arg Leu Pro Ala Leu Arg Ser Ile
            420                 425                 430

Ser Leu Lys Ser Phe Glu His Leu Tyr Phe Phe His Leu Val Ala Glu
            435                 440                 445

Gly Ser Ile Ser Gly Tyr Ile Arg Glu Ala Leu Arg Asn His Ala Pro
450                 455                 460

Pro Ile Asp Val Asn Ala Met Met
465                 470
```

<210> SEQ ID NO 62
<211> LENGTH: 1404
<212> TYPE: DNA
<213> ORGANISM: Mus musculus
<220> FEATURE:
<221> NAME/KEY: misc_feature
<223> OTHER INFORMATION: Novel Sequence

<400> SEQUENCE: 62

```
atggacacca acatttcct gccgctcgac ttctctaccc aggtgaactc ttcgtccctc      60
aactctccaa cgggtcgagg ctccatggct gtccctcgc tgcacccctc cttgggtccg     120
ggaatcggct ctccactggg ctcgcctggg cagctgcact ctcctatcag cacccctgagc   180
tcccccatca atggcatggg tccgcccttc tctgtcatca gctcccccat gggcccgcac    240
tccatgtcgg tacccaccac acccacattg ggcttcggga ctggtagccc ccagctcaat    300
tcacccatga accctgtgag cagcactgag gatatcaagc cgccactagg cctcaatggc    360
gtcctcaagg ttcctgccca tccctcagga aatatggcct ccttcaccaa gcacatctgt    420
gctatctgtg gggaccgctc ctcaggcaaa cactatgggg tatacagttg tgagggctgc    480
aagggcttct tcaagaggac agtacgcaaa gacctgacct acacctgccg agacaacaag    540
gactgcctga tcgacaagag acagcggaac cggtgtcagt actgccgcta ccagaagtgc    600
ctggccatgg gcatgaagcg ggaagctgtg caggaggagc ggcagcgggg caaggaccgg    660
aatgagaacg aggtggagtc caccagcagt gccaacgagg acatgcctgt agagaagatt    720
```

```
ctggaagccg agcttgctgt cgagcccaag actgagacat acgtggaggc aaacatgggg      780
ctgaacccca gctcaccaaa tgaccctgtt accaacatct gtcaagcagc agacaagcag      840
ctcttcactc ttgtggagtg ggccaagagg atcccacact tttctgagct gcccctagac      900
gaccaggtca tcctgctacg ggcaggctgg aacgagctgc tgatcgcctc cttctcccac      960
cgctccatag ctgtgaaaga tgggattctc ctggccaccg gcctgcacgt acaccggaac     1020
agcgctcaca gtgctggggt gggcgccatc tttgacaggt gctaacagaa gctggtgtct     1080
aagatgcgtg acatgcagat ggacaagacg gagctgggct gcctgcgagc cattgtcctg     1140
ttcaaccctg actctaaggg gctctcaaac cctgctgagg tggaggcgtt gagggagaag     1200
gtgtatgcgt cactagaagc gtactgcaaa cacaagtacc ctgagcagcc gggcaggttt     1260
gccaagctgc tgctccgcct gcctgcactg cgttccatcg ggctcaagtg cctggagcac     1320
ctgttcttct tcaagctcat cggggacacg cccatcgaca ccttcctcat ggagatgctg     1380
gaggcaccac atcaagccac ctag                                            1404
```

<210> SEQ ID NO 63
<211> LENGTH: 467
<212> TYPE: PRT
<213> ORGANISM: Mus musculus
<220> FEATURE:
<221> NAME/KEY: misc_feature
<223> OTHER INFORMATION: Novel Sequence

<400> SEQUENCE: 63

```
Met Asp Thr Lys His Phe Leu Pro Leu Asp Phe Ser Thr Gln Val Asn
1               5                   10                  15

Ser Ser Ser Leu Asn Ser Pro Thr Gly Arg Gly Ser Met Ala Val Pro
            20                  25                  30

Ser Leu His Pro Ser Leu Gly Pro Gly Ile Gly Ser Pro Leu Gly Ser
        35                  40                  45

Pro Gly Gln Leu His Ser Pro Ile Ser Thr Leu Ser Ser Pro Ile Asn
    50                  55                  60

Gly Met Gly Pro Pro Phe Ser Val Ile Ser Ser Pro Met Gly Pro His
65                  70                  75                  80

Ser Met Ser Val Pro Thr Thr Pro Thr Leu Gly Phe Gly Thr Gly Ser
                85                  90                  95

Pro Gln Leu Asn Ser Pro Met Asn Pro Val Ser Ser Thr Glu Asp Ile
            100                 105                 110

Lys Pro Pro Leu Gly Leu Asn Gly Val Leu Lys Val Pro Ala His Pro
        115                 120                 125

Ser Gly Asn Met Ala Ser Phe Thr Lys His Ile Cys Ala Ile Cys Gly
    130                 135                 140

Asp Arg Ser Ser Gly Lys His Tyr Gly Val Tyr Ser Cys Glu Gly Cys
145                 150                 155                 160

Lys Gly Phe Phe Lys Arg Thr Val Arg Lys Asp Leu Thr Tyr Thr Cys
                165                 170                 175

Arg Asp Asn Lys Asp Cys Leu Ile Asp Lys Arg Gln Arg Asn Arg Cys
            180                 185                 190

Gln Tyr Cys Arg Tyr Gln Lys Cys Leu Ala Met Gly Met Lys Arg Glu
        195                 200                 205

Ala Val Gln Glu Glu Arg Gln Arg Gly Lys Asp Arg Asn Glu Asn Glu
    210                 215                 220

Val Glu Ser Thr Ser Ser Ala Asn Glu Asp Met Pro Val Glu Lys Ile
225                 230                 235                 240
```

```
Leu Glu Ala Glu Leu Ala Val Glu Pro Lys Thr Glu Thr Tyr Val Glu
                245                 250                 255
Ala Asn Met Gly Leu Asn Pro Ser Ser Pro Asn Asp Pro Val Thr Asn
            260                 265                 270
Ile Cys Gln Ala Ala Asp Lys Gln Leu Phe Thr Leu Val Glu Trp Ala
        275                 280                 285
Lys Arg Ile Pro His Phe Ser Glu Leu Pro Leu Asp Asp Gln Val Ile
    290                 295                 300
Leu Leu Arg Ala Gly Trp Asn Glu Leu Leu Ile Ala Ser Phe Ser His
305                 310                 315                 320
Arg Ser Ile Ala Val Lys Asp Gly Ile Leu Leu Ala Thr Gly Leu His
                325                 330                 335
Val His Arg Asn Ser Ala His Ser Ala Gly Val Gly Ala Ile Phe Asp
            340                 345                 350
Arg Val Leu Thr Glu Leu Val Ser Lys Met Arg Asp Met Gln Met Asp
        355                 360                 365
Lys Thr Glu Leu Gly Cys Leu Arg Ala Ile Val Leu Phe Asn Pro Asp
    370                 375                 380
Ser Lys Gly Leu Ser Asn Pro Ala Glu Val Glu Ala Leu Arg Glu Lys
385                 390                 395                 400
Val Tyr Ala Ser Leu Glu Ala Tyr Cys Lys His Lys Tyr Pro Glu Gln
                405                 410                 415
Pro Gly Arg Phe Ala Lys Leu Leu Leu Arg Leu Pro Ala Leu Arg Ser
            420                 425                 430
Ile Gly Leu Lys Cys Leu Glu His Leu Phe Phe Phe Lys Leu Ile Gly
        435                 440                 445
Asp Thr Pro Ile Asp Thr Phe Leu Met Glu Met Leu Glu Ala Pro His
    450                 455                 460
Gln Ala Thr
465

<210> SEQ ID NO 64
<211> LENGTH: 309
<212> TYPE: DNA
<213> ORGANISM: Simian virus 40
<220> FEATURE:
<221> NAME/KEY: misc_feature
<223> OTHER INFORMATION: Novel Sequence

<400> SEQUENCE: 64
ggtgtggaaa gtccccaggc tccccagcag gcagaagtat gcaaagcatg catctcaatt     60
agtcagcaac caggtgtgga agtccccag gctccccagc aggcagaagt atgcaaagca    120
tgcatctcaa ttagtcagca accatagtcc cgcccctaac tccgcccatc ccgcccctaa    180
ctccgcccag ttccgcccat tctccgcccc atggctgact aattttttt atttatgcag    240 aggccgaggc cgcctcggcc tctgagctat tccagaagta gtgaggaggc ttttttggag    300
gcctaggct                                                            309

<210> SEQ ID NO 65
<211> LENGTH: 24
<212> TYPE: DNA
<213> ORGANISM: Artificial Sequence
<220> FEATURE:
<223> OTHER INFORMATION: synthetic E1b minimal promoter
<221> NAME/KEY: misc_feature
<223> OTHER INFORMATION: Novel Sequence
```

<400> SEQUENCE: 65
tatataatgg atccccgggt accg 24

<210> SEQ ID NO 66
<211> LENGTH: 1653
<212> TYPE: DNA
<213> ORGANISM: Photinus pyralis
<220> FEATURE:
<221> NAME/KEY: misc_feature
<223> OTHER INFORMATION: Novel Sequence

<400> SEQUENCE: 66

| atggaagacg ccaaaaacat aaagaaaggc ccggcgccat tctatcctct agaggatgga | 60 |
| accgctggag agcaactgca taaggctatg aagagatacg ccctggttcc tggaacaatt | 120 |
| gcttttacag atgcacatat cgaggtgaac atcacgtacg cggaatactt cgaaatgtcc | 180 |
| gttcggttgg cagaagctat gaaacgatat gggctgaata caaatcacag aatcgtcgta | 240 |
| tgcagtgaaa actctcttca attctttatg ccggtgttgg gcgcgttatt tatcggagtt | 300 |
| gcagttgcgc ccgcgaacga catttataat gaacgtgaat tgctcaacag tatgaacatt | 360 |
| tcgcagccta ccgtagtgtt tgtttccaaa aagggggttgc aaaaaatttt gaacgtgcaa | 420 |
| aaaaaattac caataatcca gaaaattatt atcatggatt ctaaaacgga ttaccaggga | 480 |
| tttcagtcga tgtacacgtt cgtcacatct catctacctc ccggttttaa tgaatacgat | 540 |
| tttgtaccag agtcctttga tcgtgacaaa acaattgcac tgataatgaa ttcctctgga | 600 |
| tctactgggt tacctaaggg tgtggccctt ccgcatagaa ctgcctgcgt cagattctcg | 660 |
| catgccagag atcctatttt tggcaatcaa atcattccgg atactgcgat tttaagtgtt | 720 |
| gttccattcc atcacggttt tggaatgttt actacactcg gatatttgat atgtggattt | 780 |
| cgagtcgtct taatgtatag atttgaagaa gagctgtttt tacgatccct tcaggattac | 840 |
| aaaattcaaa gtgcgttgct agtaccaacc ctatttttcat tcttcgccaa aagcactctg | 900 |
| attgacaaat acgatttatc taatttacac gaaattgctt ctgggggcgc acctctttcg | 960 |
| aaagaagtcg gggaagcggt tgcaaaacgc ttccatcttc cagggatacg acaaggatat | 1020 |
| gggctcactg agactacatc agctattctg attacacccg agggggatga taaaccgggc | 1080 |
| gcggtcggta agttgttcc atttttttgaa gcgaaggttg tggatctgga taccgggaaa | 1140 |
| acgctgggcg ttaatcagag aggcgaatta tgtgtcagag gacctatgat tatgtccggt | 1200 |
| tatgtaaaca atccggaagc gaccaacgcc ttgattgaca aggatggatg gctacattct | 1260 |
| ggagacatag cttactggga cgaagacgaa cacttcttca tagttgaccg cttgaagtct | 1320 |
| ttaattaaat acaaaggata tcaggtggcc cccgctgaat tggaatcgat attgttacaa | 1380 |
| caccccaaca tcttcgacgc gggcgtggca ggtcttcccg acgatgacgc cggtgaactt | 1440 |
| cccgccgccg ttgttgtttt ggagcacgga aagacgatga cggaaaaaga tcgtggat | 1500 |
| tacgtcgcca gtcaagtaac aaccgcgaaa aagttgcgcg gaggagttgt gtttgtggac | 1560 |
| gaagtaccga aaggtcttac cggaaaactc gacgcaagaa aaatcagaga gatcctcata | 1620 |
| aaggccaaga agggcggaaa gtccaaattg taa | 1653 |

<210> SEQ ID NO 67
<211> LENGTH: 867
<212> TYPE: DNA
<213> ORGANISM: Choristoneura fumiferana
<220> FEATURE:
<221> NAME/KEY: misc_feature
<223> OTHER INFORMATION: Novel Sequence

<400> SEQUENCE: 67

```
aagcgagagg cggtgcaaga ggagcgccag aggaatgctc gcggcgcgga ggatgcgcac    60
ccgagtagct cggtgcaggt aagcgatgag ctgtcaatcg agcgcctaac ggagatggag   120
tctttggtgg cagatcccag cgaggagttc cagttcctcc gcgtggggcc tgacagcaac   180
gtgcctccac gttaccgcgc gcccgtctcc tccctctgcc aaataggcaa caagcaaata   240
gcggcgttgg tggtatgggc gcgcgacatc cctcatttcg ggcagctgga gctggacgat   300
caagtggtac tcatcaaggc ctcctggaat gagctgctac tcttcgccat cgcctggcgc   360
tctatggagt atttggaaga tgagagggag aacggggacg gaacgcggag caccactcag   420
ccacaactga tgtgtctcat gcctggcatg acgttcacc gcaactcggc gcagcaggcg    480
ggcgtgggcg ccatcttcga ccgcgtgctg tccgagctca gtctgaagat gcgcaccttg   540
cgcatggacc aggccgagta cgtcgcgctc aaagccatcg tgctgctcaa ccctgatgtg   600
aaaggactga agaatcggca agaagttgac gttttgcgag aaaaaatgtt ctcttgcctg   660
gacgactact gccggcggtc gcgaagcaac gaggaaggcc ggtttgcgtc cttgctgctg   720
cggctgccag ctctccgctc catctcgctc aagagcttcg aacacctcta cttcttccac   780
ctcgtggccg aaggctccat cagcggatac atacgagagg cgctccgaaa ccacgcgcct   840
ccgatcgacg tcaatgccat gatgtaa                                      867
```

<210> SEQ ID NO 68
<211> LENGTH: 619
<212> TYPE: DNA
<213> ORGANISM: Cytomegalovirus
<220> FEATURE:
<221> NAME/KEY: misc_feature
<223> OTHER INFORMATION: Novel Sequence

<400> SEQUENCE: 68

```
cgttacataa cttacggtaa atggcccgcc tggctgaccg cccaacgacc cccgcccatt    60
gacgtcaata atgacgtatg ttcccatagt aacgccaata gggactttcc attgacgtca   120
atgggtggag tatttacggt aaactgccca cttggcagta catcaagtgt atcatatgcc   180
aagtacgccc cctattgacg tcaatgacgg taaatggccc gcctggcatt atgcccagta   240
catgacctta tgggactttc ctacttggca gtacatctac gtattagtca tcgctattac   300
catggtgatg cggttttggc agtacatcaa tgggcgtgga tagcggtttg actcacgggg   360
atttccaagt ctccacccca ttgacgtcaa tgggagtttg ttttggcacc aaaatcaacg   420
ggactttcca aaatgtcgta caactccgcc ccattgacg caaatgggcg gtaggcgtgt   480
acggtgggag gtctatataa gcagagctcg tttagtgaac cgtcagatcg cctggagacg   540
ccatccacgc tgttttgacc tccatagaag acaccgggac cgatccagcc tccgcggccg   600
ggaacggtgc attggaacg                                               619
```

<210> SEQ ID NO 69
<211> LENGTH: 262
<212> TYPE: DNA
<213> ORGANISM: Rous sarcoma virus
<220> FEATURE:
<221> NAME/KEY: misc_feature
<223> OTHER INFORMATION: Novel Sequence

<400> SEQUENCE: 69

```
atgtagtctt atgcaatact cttgtagtct tgcaacatgg taacgatgag ttagcaacat    60
```

| gccttacaag gagagaaaaa gcaccgtgca tgccgatagg tggaagtaag gtggtacgat | 120 |
| cgtgccttat taggaaggca acagacgggt ctgacatgga ttggacgaac cactgaattc | 180 |
| cgcattgcag agatattgta tttaagtgcc tagctcgata caataaacgc catttgacca | 240 |
| ttcaccacat tggagtgcac ct | 262 |

<210> SEQ ID NO 70
<211> LENGTH: 1247
<212> TYPE: DNA
<213> ORGANISM: Choristoneura fumiferana
<220> FEATURE:
<221> NAME/KEY: misc_feature
<223> OTHER INFORMATION: Novel Sequence

<400> SEQUENCE: 70

| tctatttcct caggccgtga ggaactgtcg ccagcttcaa gtataaatgg gtgcagtaca | 60 |
| gatggcgagg cacgacgtca gaagaagggc cctgcgcccc gtcagcaaga ggaactgtgt | 120 |
| ctggtatgcg gggacagagc tccggatac cactacaatg cgctcacgtg tgaagggtgt | 180 |
| aaaggggttct tcagacggag tgttaccaaa aatgcggttt atatttgtaa attcggtcac | 240 |
| gcttgcgaaa tggacatgta catgcgacgg aaatgccagg agtgccgcct gaagaagtgc | 300 |
| ttagctgtag gcatgaggcc tgagtgcgta gtacccgaga ctcagtgcgc catgaagcgg | 360 |
| aaagagaaga agcacagaa ggagaaggac aaactgcctg tcagcacgac gacggtggac | 420 |
| gaccacatgc cgcccattat gcagtgtgaa cctccacctc ctgaagcagc aaggattcac | 480 |
| gaagtggtcc caaggtttct ctccgacaag ctgttggaga caaaccggca gaaaaacatc | 540 |
| ccccagttga cagccaacca gcagttcctt atcgccaggc tcatctggta ccaggacggg | 600 |
| tacgagcagc cttctgatga agatttgaag aggattacgc agacgtggca gcaagcggac | 660 |
| gatgaaaacg aagagtctga cactcccttc cgccagatca cagagatgac tatcctcacg | 720 |
| gtccaactta tcgtggagtt cgcgaaggga ttgccagggt tcgccaagat ctcgcagcct | 780 |
| gatcaaatta cgctgcttaa ggcttgctca agtgaggtaa tgatgctccg agtcgcgcga | 840 |
| cgatacgatg cggcctcaga cagtgttctg ttcgcgaaca accaagcgta cactcgcgac | 900 |
| aactaccgca aggctggcat ggcctacgtc atcgaggatc tactgcactt ctgccggtgc | 960 |
| atgtactcta tggcgttgga caacatccat tacgcgctgc tcacggctgt cgtcatcttt | 1020 |
| tctgaccggc cagggttgga gcagccgcaa ctggtggaag aaatccagcg gtactacctg | 1080 |
| aatacgctcc gcatctatat cctgaaccag ctgagcgggt cggcgcgttc gtccgtcata | 1140 |
| tacggcaaga tcctctcaat cctctctgag ctacgcacgc tcggcatgca aaactccaac | 1200 |
| atgtgcatct ccctcaagct caagaacaga aagctgccgc ttttcct | 1247 |

<210> SEQ ID NO 71
<211> LENGTH: 440
<212> TYPE: PRT
<213> ORGANISM: Choristoneura fumiferana
<220> FEATURE:
<221> NAME/KEY: misc_feature
<223> OTHER INFORMATION: Novel Sequence

<400> SEQUENCE: 71

Ser Ile Ser Ser Gly Arg Glu Glu Leu Ser Pro Ala Ser Ser Ile Asn
1               5                   10                  15

Gly Cys Ser Thr Asp Gly Glu Ala Arg Arg Gln Lys Lys Gly Pro Ala
            20                  25                  30

Pro Arg Gln Gln Glu Glu Leu Cys Leu Val Cys Gly Asp Arg Ala Ser

```
                35                  40                  45
Gly Tyr His Tyr Asn Ala Leu Thr Cys Glu Gly Cys Lys Gly Phe Phe
 50                  55                  60
Arg Arg Ser Val Thr Lys Asn Ala Val Tyr Ile Cys Lys Phe Gly His
 65                  70                  75                  80
Ala Cys Glu Met Asp Met Tyr Met Arg Arg Lys Cys Gln Glu Cys Arg
                 85                  90                  95
Leu Lys Lys Cys Leu Ala Val Gly Met Arg Pro Glu Cys Val Val Pro
            100                 105                 110
Glu Thr Gln Cys Ala Met Lys Arg Lys Glu Lys Ala Gln Lys Glu
        115                 120                 125
Lys Asp Lys Leu Pro Val Ser Thr Thr Val Asp Asp His Met Pro
130                 135                 140
Pro Ile Met Gln Cys Glu Pro Pro Pro Glu Ala Ala Arg Ile His
145                 150                 155                 160
Glu Val Val Pro Arg Phe Leu Ser Asp Lys Leu Leu Glu Thr Asn Arg
                165                 170                 175
Gln Lys Asn Ile Pro Gln Leu Thr Ala Asn Gln Gln Phe Leu Ile Ala
            180                 185                 190
Arg Leu Ile Trp Tyr Gln Asp Gly Tyr Glu Gln Pro Ser Asp Glu Asp
        195                 200                 205
Leu Lys Arg Ile Thr Gln Thr Trp Gln Gln Ala Asp Asp Glu Asn Glu
        210                 215                 220
Glu Ser Asp Thr Pro Phe Arg Gln Ile Thr Glu Met Thr Ile Leu Thr
225                 230                 235                 240
Val Gln Leu Ile Val Glu Phe Ala Lys Gly Leu Pro Gly Phe Ala Lys
                245                 250                 255
Ile Ser Gln Pro Asp Gln Ile Thr Leu Leu Lys Ala Cys Ser Ser Glu
            260                 265                 270
Val Met Met Leu Arg Val Ala Arg Arg Tyr Asp Ala Ala Ser Asp Ser
        275                 280                 285
Val Leu Phe Ala Asn Asn Gln Ala Tyr Thr Arg Asp Asn Tyr Arg Lys
        290                 295                 300
Ala Gly Met Ala Tyr Val Ile Glu Asp Leu Leu His Phe Cys Arg Cys
305                 310                 315                 320
Met Tyr Ser Met Ala Leu Asp Asn Ile His Tyr Ala Leu Leu Thr Ala
                325                 330                 335
Val Val Ile Phe Ser Asp Arg Pro Gly Leu Glu Gln Pro Gln Leu Val
            340                 345                 350
Glu Glu Ile Gln Arg Tyr Tyr Leu Asn Thr Leu Arg Ile Tyr Ile Leu
        355                 360                 365
Asn Gln Leu Ser Gly Ser Ala Arg Ser Ser Val Ile Tyr Gly Lys Ile
        370                 375                 380
Leu Ser Ile Leu Ser Glu Leu Arg Thr Leu Gly Met Gln Asn Ser Asn
385                 390                 395                 400
Met Cys Ile Ser Leu Lys Leu Lys Asn Arg Lys Leu Pro Pro Phe Leu
                405                 410                 415
Glu Glu Ile Trp Asp Val Ala Asp Met Ser His Thr Gln Pro Pro Pro
            420                 425                 430
Ile Leu Glu Ser Pro Thr Asn Leu
        435                 440

<210> SEQ ID NO 72
```

<211> LENGTH: 943
<212> TYPE: DNA
<213> ORGANISM: Renilla
<220> FEATURE:
<221> NAME/KEY: misc_feature
<223> OTHER INFORMATION: Novel Sequence

<400> SEQUENCE: 72

| | | | | |
|---|---|---|---|---|
| atgacttcga | aagtttatga | tccagaacaa | aggaaacgga | tgataactgg tccgcagtgg | 60 |
| tgggccagat | gtaaacaaat | gaatgttctt | gattcattta | ttaattatta tgattcagaa | 120 |
| aaacatgcag | aaaatgctgt | tattttttta | catggtaacg | cggcctcttc ttatttatgg | 180 |
| cgacatgttg | tgccacatat | tgagccagta | gcgcggtgta | ttataccaga ccttattggt | 240 |
| atgggcaaat | caggcaaatc | tggtaatggt | tcttataggt | tacttgatca ttacaaatat | 300 |
| cttactgcat | ggtttgaact | tcttaattta | ccaaagaaga | tcattttgt cggccatgat | 360 |
| tggggtgctt | gtttggcatt | tcattatagc | tatgagcatc | aagataagat caaagcaata | 420 |
| gttcacgctg | aaagtgtagt | agatgtgatt | gaatcatggg | atgaatggcc tgatattgaa | 480 |
| gaagatattg | cgttgatcaa | atctgaagaa | ggagaaaaaa | tggttttgga gaataacttc | 540 |
| ttcgtggaaa | ccatgttgcc | atcaaaaatc | atgagaaagt | tagaaccaga agaatttgca | 600 |
| gcatatcttg | aaccattcaa | agagaaaggt | gaagttcgtc | gtccaacatt atcatggcct | 660 |
| cgtgaaatcc | cgttagtaaa | aggtggtaaa | cctgacgttg | tacaaattgt taggaattat | 720 |
| aatgcttatc | tacgtgcaag | tgatgattta | ccaaaaatgt | ttattgaatc ggacccagga | 780 |
| ttcttttcca | atgctattgt | tgaaggtgcc | aagaagtttc | ctaatactga atttgtcaaa | 840 |
| gtaaaaggtc | ttcattttc | gcaagaagat | gcacctgatg | aaatgggaaa atatatcaaa | 900 |
| tcgttcgttg | agcgagttct | caaaaatgaa | caataattct aga | | 943 |

<210> SEQ ID NO 73
<211> LENGTH: 530
<212> TYPE: DNA
<213> ORGANISM: Saccharomyces cerevisiae

<400> SEQUENCE: 73

| | | | | |
|---|---|---|---|---|
| ccccattatc | ttagcctaaa | aaaaccttct | ctttggaact | ttcagtaata cgcttaactg | 60 |
| ctcattgcta | tattgaagta | cggattagaa | gccgccgagc | gggtgacagc cctccgaagg | 120 |
| aagactctcc | tccgtgcgtc | ctcgtcttca | ccggtcgcgt | tcctgaaacg cagatgtgcc | 180 |
| tcgcgccgca | ctgctccgaa | caataaagat | tctacaatac | tagctttat ggttatgaag | 240 |
| aggaaaaatt | ggcagtaacc | tggccccaca | aaccttcaaa | tgaacgaatc aaattaacaa | 300 |
| ccataggatg | ataatgcgat | tagttttta | gccttatttc | tggggtaatt aatcagcgaa | 360 |
| gcgatgattt | tgatctatt | aacagatata | taaatgcaaa | aactgcataa ccactttaac | 420 |
| taatactttc | aacattttcg | gtttgtatta | cttcttattc | aaatgtaata aaagtatcaa | 480 |
| caaaaaattg | ttaatatacc | tctatacttt | aacgtcaagg | aggaattaag | 530 |

<210> SEQ ID NO 74
<211> LENGTH: 3157
<212> TYPE: DNA
<213> ORGANISM: Escherichia coli

<400> SEQUENCE: 74

| | | | | |
|---|---|---|---|---|
| atgggggtt | ctcatcatca | tcatcatcat | ggtatggcta | gcatgactgg tggacagcaa | 60 |
| atgggtcggg | atctgtacga | cgatgacgat | aaggtaccta | aggatcagct tggagttgat | 120 |

-continued

```
cccgtcgttt tacaacgtcg tgactgggaa aaccctggcg ttacccaact taatcgcctt      180
gcagcacatc cccctttcgc cagctggcgt aatagcgaag aggcccgcac cgatcgccct      240
tcccaacagt tgcgcagcct gaatggcgaa tggcgctttg cctggtttcc ggcaccagaa      300
gcggtgccgg aaagctggct ggagtgcgat cttcctgagg ccgatactgt cgtcgtcccc      360
tcaaactggc agatgcacgg ttacgatgcg cccatctaca ccaacgtaac ctatcccatt      420
acggtcaatc cgccgtttgt tcccacggag aatccgacgg ttgttactcg ctcacatttt      480
aatgttgatg aaagctggct acaggaaggc cagacgcgaa ttattttga tggcgttaac      540 tcggcgtttc atctgtggtg caacgggcgc tgggtcggtt acggccagga cagtcgtttg      600
ccgtctgaat ttgacctgag cgcatttttta cgcgccggag aaaaccgcct cgcggtgatg      660
gtgctgcgtt ggagtgacgg cagttatctg gaagatcagg atatgtggcg gatgagcggc      720
attttccgtg acgtctcgtt gctgcataaa ccgactacac aaatcagcga tttccatgtt      780
gccactcgct ttaatgatga tttcagccgc gctgtactgg aggctgaagt tcagatgtgc      840
ggcgagttgc gtgactacct acgggtaaca gtttctttat ggcagggtga aacgcaggtc      900
gccagcggca ccgcgccttt cggcggtgaa attatcgatg agcgtggtgg ttatgccgat      960
cgcgtcacac tacgtctgaa cgtcgaaaac ccgaaactgt ggagcgccga atcccgaat     1020 ctctatcgtg cggtggttga actgcacacc gccgacggca cgctgattga agcagaagcc     1080
tgcgatgtcg gtttccgcga ggtgcggatt gaaaatggtc tgctgctgct gaacggcaag     1140
ccgttgctga ttcgaggcgt taaccgtcac gagcatcatc ctctgcatgg tcaggtcatg     1200
gatgagcaga cgatggtgca ggatatcctg ctgatgaagc agaacaactt taacgccgtg     1260
cgctgttcgc attatccgaa ccatccgctg tggtacacgc tgtgcgaccg ctacggcctg     1320
tatgtggtgg atgaagccaa tattgaaacc cacggcatgg tgccaatgaa tcgtctgacc     1380
gatgatccgc gctggctacc ggcgatgagc gaacgcgtaa cgcgaatggt gcagcgcgat     1440
cgtaatcacc cgagtgtgat catctggtcg ctggggaatg aatcaggcca cggcgctaat     1500
cacgacgcgc tgtatcgctg gatcaaatct gtcgatcctt cccgcccggt gcagtatgaa     1560
ggcggcggag ccgacaccac ggccaccgat attatttgcc cgatgtacgc gcgcgtggat     1620
gaagaccagc ccttcccggc tgtgccgaaa tggtccatca aaaaatggct ttcgctacct     1680
ggagagacgc gcccgctgat cctttgcgaa tacgcccacg cgatgggtaa cagtcttggc     1740
ggtttcgcta atactggca ggcgtttcgt cagtatcccc gtttacaggg cggcttcgtc     1800
tgggactggg tggatcagtc gctgattaaa tatgatgaaa acggcaaccc gtggtcggct     1860
tacggcggtg attttggcga tacgccgaac gatcgccagt tctgtatgaa cggtctggtc     1920
tttgccgacc gcacgccgca tccagcgctg acggaagcaa acaccagca gcagttttc      1980 cagttccgtt tatccgggca aaccatcgaa gtgaccagcg aatacctgtt ccgtcatagc     2040
gataacgagc tcctgcactg gatggtgcg ctggatggta agccgctggc aagcggtgaa      2100
gtgcctctgg atgtcgctcc acaaggtaaa cagttgattg aactgcctga actaccgcag     2160
ccggagagcg ccgggcaact ctggctcaca gtacgcgtag tgcaaccgaa cgcgaccgca     2220
tggtcagaag ccgggcacat cagcgcctgg cagcagtggc gtctggcgga aaacctcagt     2280
gtgacgctcc ccgccgcgtc ccacgccatc ccgcatctga ccaccagcga atggattttt     2340
tgcatcgagc tgggtaataa gcgttggcaa tttaaccgcc agtcaggctt tctttcacag     2400
atgtggattg gcgataaaaa acaactgctg acgccgctgc gcgatcagtt cacccgtgca     2460
ccgctggata cgacattgg cgtaagtgaa gcgacccgca ttgaccctaa cgcctgggtc     2520
```

```
gaacgctgga aggcggcggg ccattaccag gccgaagcag cgttgttgca gtgcacggca    2580
gatacacttg ctgatgcggt gctgattacg accgctcacg cgtggcagca tcagggggaaa   2640 accttattta tcagccggaa aacctaccgg attgatggta gtggtcaaat ggcgattacc    2700
gttgatgttg aagtggcgag cgatacaccg catccggcgc ggattggcct gaactgccag    2760
ctggcgcagg tagcagagcg ggtaaactgg ctcggattag ggccgcaaga aaactatccc    2820
gaccgcctta ctgccgcctg ttttgaccgc tgggatctgc cattgtcaga catgtatacc    2880
ccgtacgtct tcccgagcga aaacggtctg cgctgcggga cgcgcgaatt gaattatggc    2940
ccacaccagt ggcgcggcga cttccagttc aacatcagcc gctacagtca acagcaactg    3000
atggaaacca gccatcgcca tctgctgcac gcggaagaag gcacatggct gaatatcgac    3060
ggtttccata tggggattgg tggcgacgac tcctggagcc cgtcagtatc ggcggaatta    3120
cagctgagcg ccggtcgcta ccattaccag ttggtct                             3157

<210> SEQ ID NO 75
<211> LENGTH: 185
<212> TYPE: DNA
<213> ORGANISM: Escherichia coli

<400> SEQUENCE: 75
gtccaggtcc atatctaatc ttacctcgac tgctgtatat aaaaccagtg gttatatgta      60
cagtactgct gtatataaaa ccagtggtta tatgtacagt acgtcgactg ctgtatataa    120
aaccagtggt tatatgtaca gtactgctgt atataaaacc agtggttata tgtacagtac    180
gtcga                                                                185
```